US007825232B2

(12) United States Patent
Otte et al.

(10) Patent No.: US 7,825,232 B2
(45) Date of Patent: *Nov. 2, 2010

(54) SEQUENCE FOR IMPROVING EXPRESSION OF NUCLEIC ACID

(75) Inventors: Arie Pieter Otte, Amersfoort (NL); Theodorus Hendrikus Jacobus Kwaks, Amsterdam (NL); Richard George Antonius Bernardus Sewalt, Arnhem (NL); Henricus Johannes Maria Van Blokland, Wijdewormer (NL)

(73) Assignee: Chromagenics B.V., Leiden (NL)

( * ) Notice: Subject to any disclaimer, the term of this patent is extended or adjusted under 35 U.S.C. 154(b) by 683 days.

This patent is subject to a terminal disclaimer.

(21) Appl. No.: 11/632,012

(22) PCT Filed: Jul. 7, 2005

(86) PCT No.: PCT/EP2005/053251

§ 371 (c)(1), (2), (4) Date: Jan. 8, 2007

(87) PCT Pub. No.: WO2006/005718

PCT Pub. Date: Jan. 19, 2006

(65) Prior Publication Data

US 2007/0212755 A1     Sep. 13, 2007

(30) Foreign Application Priority Data

Jul. 8, 2004 (WO) ............... PCT/EP2004/051405

(51) Int. Cl.
C07H 21/04 (2006.01)
C07H 21/02 (2006.01)

(52) U.S. Cl. .................... 536/23.5; 536/23.1
(58) Field of Classification Search ............... 536/23.1, 536/23.5
See application file for complete search history.

(56) References Cited

U.S. PATENT DOCUMENTS

2006/0003416 A1    1/2006   Otte et al.

FOREIGN PATENT DOCUMENTS

WO    WO 03/004704    1/2003
WO    WO 03/106684    12/2003
WO    WO 2004/056986   7/2004

OTHER PUBLICATIONS

Printout from search results that disclose Result 6 Acession No. AC084700 submitted to GenBank in 2000 by Birren et al and alignment. Printout comprises pp. 1-12.*
Lee et al. Cytotechnology 28:73-80,1998.*
PCT International Search Report, PCT/EP2005/053251, dated May 30, 2006.
U.S. Appl. No. 10/190,312, filed Jul. 5, 2002, DNA Sequences Comprising Gene Transcription Regulatory Qualities and Methods for Detecting and Using Such DNA Sequences.
U.S. Appl. No. 11/012,546, filed Dec. 14, 2004, Means and Methods for Regulating Gene Expression.
U.S. Appl. No. 11/013,031, filed Dec. 14, 2004, A Method for Simultaneous Production of Multiple Proteins; Vectors and Cells for Use Therein.
U.S. Appl. No. 11/156,910, filed Jun. 20, 2005, Means and Methods for Producing a Protein Through Chromatin Openers That Are Capable of Rendering Chromatin More Accessible to Transcription Factors.
U.S. Appl. No. 11/157,193, filed Jun. 20, 2005, A Method for Improving Protein Production.
U.S. Appl. No. 11/269,525, filed Nov. 7, 2005, Selection of Host Cells Expressing Protein At High Levels.
U.S. Appl. No. 11/359,953, filed Feb. 21, 2006, Selection of Host Cells Expressing Protein At High Levels.
U.S. Appl. No. 11/416,490, filed May 2, 2006, Selection of Host Cells Expressing Protein At High Levels.
U.S. Appl. No. 11/580,494, filed Oct. 13, 2006, Nucleic Acid Sequences Having Gene Transcription Regulatory Qualities.
U.S. Appl. No. 11/580,604, filed Oct. 13, 2006, Nucleic Acid Sequences Having Gene Transcription Regulatory Qualities.
U.S. Appl. No. 11/580,605, filed Oct. 13, 2006, Nucleic Acid Sequences Having Gene Transcription Regulatory Qualities.
U.S. Appl. No. 11/580,619, filed Oct. 13, 2006, Nucleic Acid Sequences Having Gene Transcription Regulatory Qualities.
U.S. Appl. No. 11/580,620, filed Oct. 13, 2006, Nucleic Acid Sequences Having Gene Transcription Regulatory Qualities.
U.S. Appl. No. 11/580,644, filed Oct. 13, 2006, Nucleic Acid Sequences Having Gene Transcription Regulatory Qualities.
U.S. Appl. No. 11/580,760, filed Oct. 13, 2006, Nucleic Acid Sequences Having Gene Transcription Regulatory Qualities.

* cited by examiner

Primary Examiner—Thaian N Ton
Assistant Examiner—Marcia S Noble
(74) Attorney, Agent, or Firm—TraskBritt

(57) ABSTRACT

The invention provides a novel anti-repressor element, which is useful for improving expression of nucleic acid in host cells. Methods using the novel anti-repressor element for producing a protein of interest are also provided. The invention also provides new configurations of expression cassettes comprising anti-repressor elements.

19 Claims, 11 Drawing Sheets

A

B

A

B

A

B

A

B

A

B

SEQUENCE FOR IMPROVING EXPRESSION OF NUCLEIC ACID

The invention relates to the field of molecular biology and biotechnology. More specifically the present invention relates to means and methods for improving the production of one or more nucleic acids that may encode proteins in a host cell.

Proteins can be produced in various host cells for a wide range of applications in biology and biotechnology, for instance as biopharmaceuticals. Methods for such production are well established, and generally entail the expression in a host cell of a nucleic acid (also referred to as 'transgene') encoding the protein of interest.

One problem associated with the expression of transgenes is that it is unpredictable, stemming from the high likelihood that the transgene will become inactive due to gene silencing (McBurney et al., 2002), and therefore many host cell clones have to be tested for high expression of the transgene. Furthermore, once such a clone has been established, the expression of the transgene is often not stable and silencing of transgene expression during prolonged host cell cultivation is a commonly observed phenomenon. In vertebrate cells it can be caused by formation of heterochromatin at the transgene locus, which prevents transcription of the transgene (Whitelaw et al, 2001). Transgene silencing is stochastic; it can occur shortly after integration of the transgene into the genome, or only after a number of cell divisions. This results in heterogeneous cell populations after prolonged cultivation, in which some cells continue to express high levels of recombinant protein while others express low or undetectable levels of the protein (Martin & Whitelaw, 1996, McBurney et al., 2002). A cell line that is used for heterologous protein production is derived from a single cell, yet is often scaled up to, and maintained for long periods at, cell densities in excess of ten million cells per ml in cultivators of 1,000 liters or more. These large cell populations ($10^{14}$-$10^{16}$ cells) are prone to serious declines in productivity due to transgene silencing (Migliaccio et al., 2000, Strutzenberger et al., 1999).

One possibility to overcome the problems described above is to employ so-called STAR sequences in the expression system. A variety of such STAR sequences have been described in WO 03/004704. These sequences can be used to improve predictability, yield and/or stability of protein production using expression constructs in several types of host cells (WO 03/004704; Kwaks et al, 2003).

International publication WO 03/106674 describes the use of STAR sequences for expressing nucleic acid encoding recombinant proteins in several cell lines.

International publication WO 03/106684 describes the use of STAR sequences for expressing nucleic acid encoding multimeric proteins, such as antibodies.

The present invention aims at providing alternative means and methods for improving protein production.

SUMMARY OF THE INVENTION

In one aspect, the invention provides a recombinant nucleic acid molecule comprising a nucleic acid sequence having anti-repressor activity selected from the group consisting of: a) SEQ. ID. NO. 66, b) fragments of SEQ. ID. NO. 66 wherein said fragments have anti-repressor activity, c) sequences that are at least 70% identical in nucleotide sequence to a) or b) wherein said sequences have anti-repressor activity; and d) the complement to any one of a) to c); said recombinant nucleic acid molecule further comprising an expression cassette, said expression cassette comprising a heterologous promoter linked to a nucleic acid of interest, and wherein said nucleic acid of interest preferably encodes all or part of a protein of interest. In a preferred embodiment, said nucleic acid sequence having anti-repressor activity is situated upstream of said promoter in said expression cassette, and in particularly preferred embodiments thereof, said sequence having anti-repressor activity and said promoter are separated by less than 2 kb. In certain embodiments, said nucleic acid encoding a protein of interest is present in a multicistronic gene further encoding a selectable marker gene. In certain embodiments, said molecule further comprises at least one other sequence having anti-repressor activity, said at least one other sequence being chosen from a) any of SEQ. ID. NOs. 1-65, b) fragments of any of SEQ. ID. NOs. 1-65, wherein said fragments have anti-repressor activity, c) sequences that are at least 70% identical in nucleotide sequence to a) or b) wherein said sequences have anti-repressor activity, and d) the complement to any one of a) to c). The invention also provides a recombinant nucleic acid molecule comprising an expression cassette comprising: 5'—anti-repressor sequence A—promoter—nucleic acid encoding all or part of a protein of interest—anti-repressor sequence B—3' wherein anti-repressor sequences A and B may be the same or different and are chosen from the group consisting of (i) any of SEQ. ID. NOs. 1-65, (ii) fragments of any of SEQ. ID. NOs. 1-65, wherein said fragments have anti-repressor activity, (iii) sequences that are at least 70% identical in nucleotide sequence to a) or b) wherein said sequences have anti-repressor activity, and (iv) the complement to any one of (i) to (iii), characterized in that said expression cassette further comprises between said anti-repressor sequences A and B a sequence having anti-repressor activity chosen from the group consisting of a) SEQ. ID. NO. 66, b) fragments of SEQ. ID. NO. 66 wherein said fragment has anti-repressor activity, c) sequences that are at least 70% identical in nucleotide sequence to a) or b) wherein said sequences have anti-repressor activity; and d) the complement to any one of a) to c).

The invention further provides a cell comprising a molecule according to the invention. Preferably said cell is a mammalian cell, and in certain embodiments said cell is a CHO cell.

The invention further provides a method for producing a protein of interest, comprising culturing a cell comprising a recombinant nucleic acid molecule encoding the protein of interest to express said nucleic acid encoding the protein of interest in said cell, characterized in that said recombinant nucleic acid molecule comprises a nucleic acid sequence having anti-repressor activity selected from the group consisting of: a) SEQ. ID. NO. 66, b) fragments of SEQ. ID. NO. 66 wherein said fragments have anti-repressor activity, c) sequences that are at least 70% identical in nucleotide sequence to a) or b) wherein said sequences have anti-repressor activity; and d) the complement to any one of a) to c). In a preferred embodiment, the method further comprises isolating said protein of interest. In preferred embodiments, said nucleic acid sequence having anti-repressor activity is situated upstream of a promoter that controls expression of the protein of interest. In a preferred embodiment thereof, said sequence having anti-repressor activity and said promoter are separated by less than 2 kb. In certain embodiments, said nucleic acid encoding a protein of interest is present in a multicistronic gene further encoding a selectable marker gene. In certain embodiments, said cell is a mammalian cell, e.g. a CHO cell.

The invention also provides for the use of a nucleic acid sequence having anti-repressor activity selected from the group consisting of: a) SEQ. ID. NO. 66, b) fragments of SEQ. ID. NO. 66 wherein said fragment has anti-repressor activity, c) sequences that are at least 70% identical in nucleotide sequence to a) or b) wherein said sequences have anti-repressor activity; and d) the complement to any one of a) to c), for increasing expression of a nucleic acid of interest.

In yet another aspect, the invention provides a method for generating a host cell expressing two polypeptides of interest, the method comprising: a) introducing into a host cell one or more nucleic acid molecules, the nucleic acid molecule or molecules together comprising: (i) a promoter functionally linked to a sequence encoding a first polypeptide of interest and a first selectable marker gene, and (ii) a promoter functionally linked to a sequence encoding a second polypeptide of interest and a second selectable marker gene, and (iii) at least one sequence having anti-repressor activity, chosen from the group consisting of (a) any one of SEQ. ID. NOs. 1-66, (b) fragments of any one of SEQ. ID. NOs. 1-66, said fragments having anti-repressor activity, (c) sequences that are at least 70% identical to (a) or (b) and having anti-repressor activity, and (d) the complement of any one of (a)-(c); b) selecting a host cell by selecting essentially simultaneously for expression of said first and second selectable marker genes. The invention also provides a method for expressing two polypeptides of interest, the method comprising: culturing a host cell obtained by the method according to this aspect of the invention to express said first and second polypeptides, and optionally isolating said polypeptides. In one embodiment, said sequence having anti-repressor activity is selected from the group consisting of a) SEQ. ID. NO. 66, b) fragments of SEQ. ID. NO. 66 wherein said fragment has anti-repressor activity, c) sequences that are at least 70% identical in nucleotide sequence to a) or b) wherein said sequences have anti-repressor activity; and d) the complement to any one of a) to c). In certain embodiments, said two polypeptides are part of a multimeric protein.

DETAILED DESCRIPTION OF THE INVENTION

Anti-Repressor Sequences

Sequences having anti-repressor activity as used herein are sequences that are capable of at least in part counteracting the repressive effect of HP1 or HPC2 proteins when these proteins are tethered to DNA. Sequences having anti-repressor activity (sometimes also referred to as anti-repressor sequences or anti-repressor elements herein) suitable for the present invention, have been disclosed in WO 03/004704, incorporated herein by reference, and were coined "STAR" sequences therein (wherever a sequence is referred to as a STAR sequence herein, this sequence has anti-repressor activity according to the invention). As a non-limiting example, the sequences of 65 anti-repressor elements, named STAR1-65 (see WO 03/004704), are presented herein as SEQ. ID. NOs. 1-65, respectively.

According to the invention, a functional fragment or derivative of a given anti-repressor element is considered equivalent to said anti-repressor element, when it still has anti-repressor activity. The presence of such anti-repressor activity can easily be checked by the person skilled in the art, for instance by the assay described below. Functional fragments or derivatives can easily be obtained by a person skilled in the art of molecular biology, by starting with a given anti-repressor sequence, and making deletions, additions, substitutions, inversions and the like (see e.g. WO 03/004704). A functional fragment or derivative also comprises orthologs from other species, which can be found using the known anti-repressor sequences by methods known by the person skilled in the art (see e.g. WO 03/004704). Hence, the present invention encompasses fragments of the anti-repressor sequences, wherein said fragments still have anti-repressor activity. For fragments of a given sequence, percent identity refers to that portion of the reference native sequence that is found in the fragment. The invention also encompasses sequences that are at least 70% identical in nucleotide sequence to said sequences having anti-repressor activity or to functional fragments thereof having anti-repressor activity, as long as these sequences that are at least 70% identical still have the anti-repressor activity according to the invention. Preferably, said sequences are at least 80% identical, more preferably at least 90% identical and still more preferably at least 95% identical to the reference native sequence or functional fragment thereof.

Sequences having anti-repressor activity according to the invention can be obtained by various methods, including but not limited to the cloning from the human genome or from the genome of another organism, or by for instance amplifying known anti-repressor sequences directly from such a genome by using the knowledge of the sequences, e.g. by PCR, or can in part or wholly be chemically synthesized.

Sequences having anti-repressor activity, and functional fragments or derivatives thereof, are structurally defined herein by their sequence and in addition are functionally defined as sequences having anti-repressor activity, which can be determined with the assay described below.

Any sequence having anti-repressor activity according to the present invention should at least be capable of surviving the following functional assay (see WO 03/004704, example 1, incorporated herein by reference). Human U-2 OS cells (ATCC HTB-96) are stably transfected with the pTet-Off plasmid (Clontech K1620-A) and with nucleic acid encoding a LexA-repressor fusion protein containing the LexA DNA binding domain and the coding region of either HP1 or HPC2 (Drosophila Polycomb group proteins that repress gene expression when tethered to DNA; the assay works with either fusion protein) under control of the Tet-Off transcriptional regulatory system (Gossen and Bujard, 1992). These cells are referred to below as the reporter cells for the anti-repressor activity assay. A reporter plasmid, which provides hygromycin resistance, contains a polylinker sequence positioned between four LexA operator sites and the SV40 promoter that controls the zeocin resistance gene. The sequence to be tested for anti-repressor activity can be cloned in said polylinker. Construction of a suitable reporter plasmid, such as pSelect, is described in example 1 and FIG. 1 of WO 00/004704. The reporter plasmid is transfected into the reporter cells, and the cells are cultured under hygromycin selection (25 μg/ml; selection for presence of the reporter plasmid) and tetracycline repression (doxycycline, 10 ng/ml; prevents expression of the LexA-repressor fusion protein). After 1 week of growth under these conditions, the doxycycline concentration is reduced to 0.1 ng/ml (or lower) to induce the LexA-repressor gene, and after 2 days zeocin is added to 250 μg/ml. The cells are cultured for 5 weeks, until the control cultures (transfected with empty reporter plasmid, i.e. lacking a cloned anti-repressor sequence in the polylinker) are killed by the zeocin (in this control plasmid, the SV40 promoter is repressed by the LexA-repressor fusion protein that is tethered to the LexA operating sites, resulting in insufficient zeocin expression in such cells to survive zeocin selection). A sequence has anti-repressor activity according to the present invention if, when said sequence is cloned in the polylinker of the reporter plasmid, the reporter cells survive the 5 weeks selection under zeocin. Cells from such colonies can still be propagated onto new medium containing zeocin after the 5 weeks zeocin selection, whereas cells transfected with reporter plasmids lacking anti-repressor sequences cannot be propagated onto new medium containing zeocin. Any sequence not capable of conferring such growth after 5 weeks on zeocin in this assay, does not qualify as a sequence having anti-repressor acivity, or functional fragment or functional derivative thereof according to the present invention. As an example, known boundary sequences such as those tested by Van der Vlag et al (2000), including Drosophila scs (Kellum and Schedl, 1991), 5'-HS4 of the chicken β-globin locus (Chung et al, 1993, 1997) or Matrix Attachment Regions (MARs) (Phi-Van et al., 1990), do not survive this assay.

In addition, it is preferred that the anti-repressor sequence or functional fragment or derivative thereof confers a higher proportion of reporter over-expressing clones when flanking a reporter gene (e.g. luciferase, GFP) which is integrated into the genome of U-2 OS or CHO cells, compared to when said reporter gene is not flanked by anti-repressor sequences, or flanked by weaker repression blocking sequences such as Drosophila scs. This can be verified using for instance the pSDH vector, or similar vectors, as described in example 1 and FIG. 2 of WO 03/004704.

Anti-repressor elements of the invention can have at least one of three consequences for production of protein: (1) they increase the predictability of identifying host cell lines that express a protein at industrially acceptable levels; (2) they result in host cell lines with increased protein yields; and/or (3) they result in host cell lines that exhibit more stable protein production during prolonged cultivation. Each of these attributes is discussed in more detail below: (1) Increased predictability: Integration of transgene expression cassettes can occur at random positions throughout the host cell genome. However, much of the genome is transcriptionally silent heterochromatin. When the expression cassettes include anti-repressor elements flanking the transgene, the position of integration has a reduced effect on expression. The anti-repressor elements impair the ability of adjacent heterochromatin to silence the transgene. Consequently, the proportion of transgene-containing host cells with acceptable expression levels is increased. Indeed, incorporation of anti-repressor sequences results in the establishment of up to 10 times more colonies, compared to the same transgene lacking anti-repressor sequences, when the same amount of DNA is transfected.

(2) Yield: The levels of protein expression in primary populations of recombinant host cells, directly after transgene integration, have been surveyed. The expression level of individuals in the populations varies. However, when the transgenes are protected by anti-repressor elements, the variability is reduced. This reduced variability is most conspicuous in that fewer clones are recovered that have low levels of expression. Furthermore, the populations with anti-repressor elements commonly have individuals with strikingly high expression. These high-yielding individuals are favourable for production of proteins, either for harvesting purposes or for purposes of changing the phenotype of the cell or an organism comprising such cells.

(3) Increased Stability: anti-repressor elements increase the stability of transgenes in recombinant host cell lines by ensuring that the transgenes are not transcriptionally silenced during prolonged cultivation. Comparative trials show that, under conditions in which transgenes that are not protected by anti-repressor elements are progressively silenced (5-25 passages in cultivation), anti-repressor element-protected transgenes continue to be expressed at high levels. This is an advantage during industrial production of proteinaceous molecules, during which cell cultivation continues for prolonged periods, from a few weeks to many months. Similarly, stability of expression over prolonged periods may be advantageous in plants or animals with altered phenotypes as a consequence of recombinant expression of anti-repressor protected transgenes.

STAR67

The present invention provides a novel sequence having anti-repressor acitivity, which was coined STAR67 (SEQ. ID. NO. 66). This anti-repressor sequence already strongly increases expression when it is placed only upstream of a promoter driving expression of a gene of interest, as is evident from the examples provided herein, whereas hitherto known potent anti-repressor sequences such as STAR6 or STAR7 appear to provide much less advantage in this configuration (they function especially well when flanking a transgene, i.e. when present both upstream and downstream of the transgene). Hence, STAR67 provides an alternative to already known anti-repressor sequences, and when placed upstream of a promoter appears to have increased benefit when compared to such known anti-repressor sequences. STAR67 is not an enhancer-blocker, in contrast to other anti-repressor sequences tested for this property (Kwaks et al, 2003), providing another difference between STAR67 and other anti-repressor sequences disclosed before. Also, STAR67 may operate in a bi-directional manner, as shown in example 7. According to the invention the presence of STAR67 sequence in an expression cassette provides improved predictability and/or yield and/or stability of expression. It is demonstrated herein that STAR67 is functional in combination with various promoters, and in different cell lines.

Expression Cassette

A nucleic acid molecule according to the invention, comprising STAR67, may be in any format, e.g. as DNA fragment, optionally present on a cloning vector such as a plasmid, preferably an expression vector, and can be used for instance for cloning purposes using standard recombinant DNA technology. In preferred embodiments of the invention, nucleic acid comprises an expression cassette, which is useful to express sequences of interest, for instance in host cells.

An 'expression cassette' as used herein is a nucleic acid sequence comprising at least a promoter functionally linked to a sequence of which expression is desired, which sequence of which expression is desired preferably is an open reading frame encoding all or part of a protein of interest. The promoter is preferably a heterologous promoter with respect to said nucleic acid of interest, whereby a heterologous promoter is defined as a promoter which is not the natural promoter of said sequence of interest. In other words, some form of human intervention, e.g. molecular cloning, has been used at any point in time to make the functional combination of a heterologous promoter with a nucleic acid of interest, and it is readily understood in this context that a heterologous promoter can be derived from the same or from a different organism as the sequence of interest. Preferably, an expression cassette further contains transcription termination and polyadenylation sequences. Other regulatory sequences such as enhancers may also be included. The expression units according to the invention further comprise at least one anti-repressor sequence, such as STAR67. In certain preferred embodiments said anti-repressor sequence, preferably STAR67, is placed upstream of said promoter, preferably such that less than 2 kb are present between the 3' end of the anti-repressor sequence and the start of the promoter sequence. In preferred embodiments, less than 1 kb, more preferably less than 500 nucleotides (nt), still more preferably less than about 200, 100, 50, or 30 nt are present between the 3' end of the anti-repressor sequence and the start of the promoter sequence. In certain preferred embodiments, the anti-repressor sequence is cloned directly upstream of the promoter, resulting in only about 0-20 nt between the 3' end of the anti-repressor sequence and the start of the promoter sequence.

To obtain expression of nucleic acid sequences encoding recombinant protein, it is well known to those skilled in the art that sequences capable of driving such expression, can be functionally linked to the nucleic acid sequences encoding the protein, resulting in recombinant nucleic acid molecules encoding a recombinant protein in expressible format. In general, the promoter sequence is placed upstream of the sequences encoding the protein of interest. Useful expression vectors are available in the art, e.g. the pcDNA and pEF vector series of Invitrogen, pMSCV and pTK-Hyg from BD Sciences, pCMV-Script from Stratagene, etc.

Where the sequence encoding the polypeptide of interest is properly inserted with reference to sequences governing the transcription and translation of the encoded polypeptide, the resulting expression cassette is useful to produce the protein of interest, referred to as expression. Sequences driving expression may include promoters, enhancers and the like, and combinations thereof. These should be capable of functioning in the host cell, thereby driving expression of the nucleic acid sequences that are functionally linked to them. The person skilled in the art is aware that various promoters can be used to obtain expression of a gene of interest in host cells. Promoters can be constitutive or regulated, and can be obtained from various sources, including viruses, prokaryotic, or eukaryotic sources, or artificially designed. Expression of nucleic acids of interest may be from the natural promoter or derivative thereof or from an entirely heterologous promoter (Kaufman, 2000). Some well-known and much used promoters for expression in eukaryotic cells comprise promoters derived from viruses, such as adenovirus, e.g. the E1A promoter, promoters derived from cytomegalovirus (CMV), such as the CMV immediate early (IE) promoter (referred to herein as the CMV promoter) (obtainable for instance from pcDNA, Invitrogen), promoters derived from Simian Virus 40 (SV40) (Das et al, 1985), and the like. Suitable promoters can also be derived from eukaryotic cells, such as methallothionein (MT) promoters, elongation factor 1α (EF-1α) promoter (Gill et al., 2001), ubiquitin C or UB6 promoter (Gill et al., 2001; Schorpp et al, 1996), actin promoter, an immunoglobulin promoter, heat shock promoters, and the like. Some preferred promoters for obtaining expression in eukaryotic cells, which are suitable promoters in the present invention, are the CMV-promoter, a mammalian EF1-alpha promoter, a mammalian ubiquitin promoter such as a ubiquitin C promoter, or a SV40 promoter (e.g. obtainable from pIRES, cat. no. 631605, BD Sciences). Testing for promoter function and strength of a promoter is a matter of routine for a person skilled in the art, and in general may for instance encompass cloning a test gene such as lacZ, luciferase, GFP, etc. behind the promoter sequence, and test for expression of the test gene. Of course, promoters may be altered by deletion, addition, mutation of sequences therein, and tested for functionality, to find new, attenuated, or improved promoter sequences.

An expression cassette according to the invention may be monocistronic, bicistronic or multicistronic. The term "bicistronic gene," is defined as a gene capable of providing a RNA molecule that encodes two proteins/polypeptides. The term "monocistronic gene" is defined as a gene capable of providing a RNA molecule that encodes one protein/polypeptide. The term "multicistronic" is defined as a gene capable of providing a RNA molecule that encodes two or more proteins/polypeptides, and a bicistronic gene is therefore encompassed within the definition of a multicistronic gene. A "gene" as used in the present invention can comprise chromosomal DNA, cDNA, artificial DNA, combinations thereof, and the like, and could also be in the form of other nucleic acid, e.g. RNA. In certain embodiments, a protein expression unit comprises a multicistronic gene. Units comprising several cistrons can be transcribed as a single mRNA. Translation of the second and further coding regions present on that RNA can be achieved in various ways, including the use of translation reinitiation sites or internal ribosome entry sites, the latter of which is preferred. One advantage of bi- or multicistronic units can be an easy selection of clones expressing a protein of interest, by placing the nucleic acid encoding a selectable marker protein downstream of nucleic acid encoding a protein or polypeptide of interest.

For the production of multimeric proteins, two or more expression cassettes can be used. This embodiment has proven to give good results, e.g. for the expression of the heavy and light chain of antibodies. According to the invention, at least one of the expression cassettes, but preferably each of them, should comprise a STAR sequence. In another embodiment, the different subunits or parts of a multimeric protein are present on a single expression cassette.

Instead of or in addition to the presence of an anti-repressor sequence placed upstream of a promoter in an expression cassette, it has proven highly beneficial to provide an anti-repressor sequence on both sides of an expression cassette, such that expression cassette comprising the transgene is flanked by two anti-repressor sequences, which in certain embodiments are essentially identical to each other. Of course, this can also be done with STAR67, to obtain an expression cassette flanked by two STAR67 sequences. Alternative positions of a single STAR67 sequence in an expression cassette, e.g. behind the transgene, preferably behind transcriptional termination and polyadenylation signal, with the 3' end of the STAR67 sequence facing the transgene, are also possible.

An expression cassette according to the invention may optionally comprise a selection marker gene. The term "selection marker or selectable marker" is typically used to refer to a gene and/or protein whose presence can be detected directly or indirectly in a cell, for example a gene and/or a protein that inactivates a selection agent and protects the host cell from the agent's lethal or growth-inhibitory effects (e.g. an antibiotic resistance gene and/or protein). Another possibility is that said selection marker induces fluorescence or a color deposit (e.g. green fluorescent protein and derivatives, luciferase, lacZ, alkaline phosphatase, etc.). In certain embodiments, a selection marker used for the invention is zeocin, and for selecting a second expression cassette puromycin is used. The person skilled in the art will know that other selection markers are available and can be used, e.g. neomycin, blasticidin, puromycin, bleomycin, hygromycin, dhfr, etc.

The term "selection" is typically defined as the process of using a selection marker/selectable marker and a selection agent to identify host cells with specific genetic properties (e.g. that the host cell contains a transgene integrated into its genome). It is clear to a person skilled in the art that numerous combinations of selection markers are possible. An example of a possible antibiotic is provided above. The one antibiotic that is particularly advantageous is zeocin, because the zeocin-resistance protein (zeocin-R) acts by binding the drug and rendering it harmless. Therefore it is easy to titrate the amount of drug that kills cells with low levels of zeocin-R expression, while allowing the high-expressors to survive. All other antibiotic-resistance proteins in common use are enzymes, and thus act catalytically (not 1:1 with the drug). When a two-step selection is performed it is therefore advantageous to use an antibiotic resistance protein with this 1:1 binding mode of action. Hence, the antibiotic zeocin is a preferred selection marker. For convenience the zeocin antibiotic can in a two-step selection method combined with for instance puromycin, blasticidin or hygromycin, which may for instance be present in a monocistronic gene.

It is also possible to combine an antibiotic selection marker with a selection marker which provides induction of fluorescence or which provide a colour deposit. Different promoters can be used as long as they are functional in the used cell.

In certain embodiments an expression cassette is provided with a (weak) Internal Ribosome Binding Site (IRES) as an example of a protein translation initiation site with a reduced translation efficiency, e.g. between the open reading frame of the protein of interest and the selection marker open reading frame. Translation of proteins from IRES elements is less efficient than cap-dependent translation: the amount of protein from IRES-dependent open reading frames (ORFs) ranges from less than 20% to 50% of the amount from the first ORF (Mizuguchi et al., 2000). Furthermore, mutation of IRES elements can attenuate their activity, and lower the expression from the IRES-dependent ORFs to below 10% of the first ORF (Lopez de Quinto & Martinez-Salas, 1998, Rees et al., 1996). When the IRES-dependent ORF encodes a selectable marker protein, its low relative level of translation means that high absolute levels of transcription must occur in order for the recombinant host cell to be selected. Therefore, selected recombinant host cell isolates will by necessity express high amounts of the transgene mRNA. Since the recombinant protein is translated from the cap-dependent ORF, it can be produced in abundance resulting in high product yields.

Conventional expression systems are DNA molecules in the form of a recombinant plasmid or a recombinant viral genome. The plasmid or the viral genome is introduced into (eukaryotic host) cells and preferably integrated into their genomes by methods known in the art. In preferred embodiments, the present invention also uses these types of DNA molecules to deliver its improved transgene expression system. A preferred embodiment of the invention is the use of plasmid DNA for delivery of the expression system. A plasmid contains a number of components: conventional components, known in the art, are an origin of replication and a selectable marker for propagation of the plasmid in bacterial cells; a selectable marker that functions in eukaryotic cells to identify and isolate host cells that carry an integrated transgene expression system; nucleic acid encoding the protein of interest, whose high-level transcription is brought about by a promoter that is functional in eukaryotic cells (e.g. the human cytomegalovirus major immediate early promoter/enhancer, pCMV (Boshart et al., 1985); and transcriptional terminators (e.g. the SV40 polyadenylation site (Kaufman & Sharp, 1982) for the transgene of interest and the selectable marker. The vector used can be any vector that is suitable for cloning DNA and that can be used for transcription of a nucleic acid of interest. When host cells are used it is preferred that the vector is an integrating vector. Alternatively, the vector may be an episomally replicating vector.

Some non-limiting, schematic representations of possible configurations of expression cassettes are provided in FIG. 1. This is the configuration of the DNA elements of the expression cassettes in the plasmid as well as after integration into the genome. Construct A contains an expression unit that encompasses an open reading frame encoding a protein (Gene). This is upstream of the attenuated EMCV IRES (Martinez-Salas et al 1999; Mizuguchi et al 2000; Rees et al 1996), and of the open reading frame encoding the zeocin resistance selectable marker protein (zeo). The gene cassette has the SV40 transcriptional terminator at their 3' ends (t). This bicistronic transgene is transcribed at high levels from the CMV promoter. Construct B is derived from construct A, but STAR67 is now cloned upstream of the CMV promoter. Construct C is derived from construct B, but now two anti-repressor elements (in this case STAR7) are cloned to flank the entire cassette.

Combination of Anti-Repressor Sequences in Expression Cassette

It is shown herein that the combination of a first anti-repressor element upstream of a promoter and flanking the expression cassette by two other anti-repressor sequences provides superior results. In particular, when an SV40 promoter is used in CHO cells, expression is already very high in the absence of anti-repressor sequences, but is considerably enhanced when STAR67 is placed upstream of said promoter, and the whole expression cassette is flanked by two anti-repressor elements, such as STAR6, STAR7, or STAR 40.

It is therefore an object of the present invention to provide a recombinant nucleic acid molecule comprising an expression cassette comprising (from 5' to 3'): anti-repressor sequence A—promoter—nucleic acid encoding a protein of interest—anti-repressor sequence B, characterized in that said expression cassette further comprises a anti-repressor sequence C between said anti-repressor sequences A and B. In a preferred embodiment, said anti-repressor sequence C is present upstream of said promoter, in a configuration as described above under the heading 'expression cassette'. The expression cassette between the anti-repressor sequences A and B may further comprise the elements as described above for expression cassettes, e.g. transcription terminator sequence, polyadenylation signal, selection marker gene, enhancer, etc., and may be monocistronic, bicistronic or multicistronic as described above.

Two or all three of anti-repressor sequences A, B and C may be the same, or all three may be different. Anti-repressor sequences A and B may the same or different as anti-repressor sequence C. In certain embodiments, anti-repressor sequence A and B are (essentially) identical to each other. In one embodiment, anti-repressor sequence C is STAR67, or a functional fragment or derivative thereof. Anti-repressor sequences A and B can be any anti-repressor sequence, and in certain embodiments comprise one of SEQ. ID. NOs. 1-65, or functional fragments or derivatives thereof. In certain embodiments, the expression cassette contains a multicistronic gene, and in preferred embodiments thereof said multicistronic gene comprises a sequence encoding a protein of interest and a selection marker gene. Alternatively, a selection marker gene is present under control of a separate promoter.

In certain embodiments, a fourth anti-repressor sequence D may be present between STAR sequences A and B. In such an embodiment, said anti-repressor sequence D is preferably positioned downstream of the nucleic acid encoding the protein of interest. Again, this anti-repressor sequence D may be the same or different from the other anti-repressor sequences in the recombinant nucleic acid molecule, it can be any anti-repressor sequence, and in certain embodiments is chosen from any one of SEQ. ID. NOs. 1-66, or functional fragments or derivatives thereof.

As at least some anti-repressor sequences can be directional (WO 00/004704), the anti-repressor sequences flanking the expression cassette (anti-repressor sequences A and B) may beneficially placed in opposite direction with respect to each other, such that the 3' end of each of these anti-repressor sequences is facing inwards to the expression cassette (and to each other). Hence, in preferred embodiments, the 5' side of an anti-repressor element faces the DNA/chromatin of which the influence on the transgene is to be diminished by said anti-repressor element. For an anti-repressor sequence upstream of a promoter in an expression cassette, the 3' end faces the promoter. The sequences of the anti-repressor elements (SEQ. ID. NOs. 1-66) in the sequence listing are given in 5' to 3' direction, unless otherwise indicated.

Cells According to the Invention

Nucleic acid molecules comprising STAR sequences and/or expression cassettes according to the present invention can be used for improving expression of nucleic acid, preferably in host cells. The terms "cell"/"host cell" and "cell line"/"host cell line" are respectively typically defined as a cell and homogeneous populations thereof that can be maintained in cell culture by methods known in the art, and that have the ability to express heterologous or homologous proteins. A host cell according to the present invention preferably is a eukaryotic cell, more preferably a mammalian cell, such as a rodent cell or a human cell or fusion between different cells. In certain non-limiting embodiments, said host cell is a U-2 OS osteosarcoma, CHO (Chinese hamster ovary), HEK 293, HuNS-1 myeloma, WERI-Rb-1 retinoblastoma, BHK, Vero, non-secreting mouse myeloma Sp2/0-Ag 14, non-secreting mouse myeloma NS0, NCI-H295R adrenal gland carcinomal or a PER.C6® cell.

In certain embodiments of the invention, a host cell is a cell expressing at least E1A, and preferably also E1B, of an adenovirus. As non-limiting examples, such a cell can be derived from for instance human cells, for instance from a kidney (example: HEK 293 cells, see Graham et al, 1977), lung (e.g. A549, see e.g. WO 98/39411) or retina (example: HER cells marketed under the trade mark PER.C6®, see U.S. Pat. No. 5,994,128), or from amniocytes (e.g. N52.E6, described in U.S. Pat. No. 6,558,948), and similarly from other cells. Methods for obtaining such cells are described for instance in U.S. Pat. No. 5,994,128 and U.S. Pat. No. 6,558,948. PER.C6® cells for the purpose of the present application means cells from an upstream or downstream passage or a descendent of an upstream or downstream passage of cells as deposited under ECACC no. 96022940. It has been previously shown that such cells are capable of expression of proteins at high levels (e.g. WO 00/63403, and Jones et al, 2003).

Such host cells expressing the desired protein according to the invention can be obtained by introduction of a nucleic acid molecule, preferably in the form of an expression cassette according to the invention, into the cells. In an alternative embodiment, the STAR67 sequence is targeted for integration into a chromosomal region to improve the expression of a gene of interest that is already integrated into the genome, e.g. a naturally occurring gene, optionally under control of a heterologous promoter that was targeted upstream of said gene to regulate expression of said gene.

Preferably the host cells are from a stable clone that can be selected and propagated according to standard procedures known to the person skilled in the art. A culture of such a clone is capable of producing recombinant protein of interest. Cells according to the invention preferably are able to grow in suspension culture in serum-free medium.

A protein of interest according to the invention can be any protein, and may be a monomeric protein or a multimeric protein. A multimeric protein comprises at least two polypeptide chains. Non-limiting examples of a protein of interest according to the invention are enzymes, hormones, immunoglobulin chains, therapeutic proteins like anti-cancer proteins, blood coagulation proteins such as Factor VIII, multifunctional proteins, such as erythropoietin, diagnostic proteins, or proteins or fragments thereof useful for vaccination purposes, all known to the person skilled in the art.

In certain embodiments, an expression cassette of the invention encodes an immunoglobulin heavy or light chain or an antigen binding part, derivative and/or analogue thereof. In a preferred embodiment a protein expression unit according to the invention is provided, wherein said protein of interest is an immunoglobulin heavy chain. In yet another preferred embodiment a protein expression unit according to the invention is provided, wherein said protein of interest is an immunoglobulin light chain. When these two protein expression units are present within the same (host) cell a multimeric protein and more specifically an antibody is assembled. Hence, in certain embodiments, the protein of interest is an immunoglobulin, such as an antibody, which is a multimeric protein. Preferably, such an antibody is a human or humanized antibody. In certain embodiments thereof, it is an IgG, IgA, or IgM antibody. An immunoglobulin may be encoded by the heavy and light chains on different expression cassettes, or on a single expression cassette, wherein the gene encoding each individual chain may each be under control of a separate promoter in monocistronic transcription units, or alternatively both chains may be encoded on a multicistronic gene.

The protein of interest may be from any source, and in certain embodiments is a mammalian protein, an artificial protein (e.g. a fusion protein or mutated protein), and preferably is a human protein.

Obviously, the anti-repressor sequences and configurations of the expression cassettes of the present invention may also be used when the ultimate goal is not the production of a protein, but the RNA itself, for instance for producing increased quantities of RNA from an expression cassette, which may be used for purposes of regulating other genes (e.g. RNAi, antisense RNA), gene therapy, in vitro protein production, etc.

Method for Producing Protein of Interest

In one aspect, the invention provides a method for expressing a sequence of interest, preferably encoding a protein of interest, by providing a host cell with a nucleic acid molecule or expression cassette according to the invention, culturing the cell and expressing the sequence of interest.

The term "expression" is typically used to refer to the production of a specific RNA product or products, or a specific protein or proteins, in a cell. In the case of RNA products, it refers to the process of transcription. In the case of protein products, it refers to the processes of transcription, translation and optionally post-translational modifications (e.g. glycosylation, disulfide bond formation, etc.). In the case of secreted proteins, it refers to the processes of transcription, translation, and optionally post-translational modification, followed by secretion.

Introduction of the nucleic acid that is to be expressed in a cell, can be done by one of several methods, which as such are known to the person skilled in the art, also dependent on the format of the nucleic acid to be introduced. Said methods include but are not limited to transfection, infection, injection, transformation, and the like.

Culturing a cell is done to enable it to metabolize, and/or grow and/or divide and/or produce recombinant proteins of interest. This can be accomplished by methods well known to persons skilled in the art, and includes but is not limited to providing nutrients for the cell. The methods comprise growth adhering to surfaces, growth in suspension, or combinations thereof. Culturing can be done for instance in dishes, roller bottles or in bioreactors, using batch, fed-batch, continuous systems such as perfusion systems, and the like. In order to achieve large scale (continuous) production of recombinant proteins through cell culture it is preferred in the art to have cells capable of growing in suspension, and it is preferred to have cells capable of being cultured in the absence of animal- or human-derived serum or animal- or human-derived serum components.

The conditions for growing or multiplying cells (see e.g. Tissue Culture, Academic Press, Kruse and Paterson, editors (1973)) and the conditions for expression of the recombinant product are known to the person skilled in the art. In general, principles, protocols, and practical techniques for maximizing the productivity of mammalian cell cultures can be found in Mammalian Cell Biotechnology: a Practical Approach (M. Butler, ed., IRL Press, 1991).

In a preferred embodiment, the expressed protein is collected (isolated), either from the cells or from the culture medium or from both. It may then be further purified using known methods, e.g. filtration, column chromatography, etc, by methods generally known to the person skilled in the art.

Novel Selection Method

The present invention discloses a novel method for generating host cells expressing two polypeptides of interest, which method gives a surprisingly good result, in that almost no or no colonies appear without the use of an anti-repressor sequence, while the presence of an anti-repressor sequence does lead to clones surviving the selection, and these clones in general express the two polypeptides of interest at high levels (example 7, FIG. 11). The invention therefore provides a method for generating a host cell expressing two polypeptides of interest, the method comprising: a) introducing into a host cell one or more nucleic acid molecules, the nucleic acid molecule or molecules together comprising: (i) a promoter functionally linked to a sequence encoding a first polypeptide of interest and a first selectable marker gene, and (ii) a promoter functionally linked to a sequence encoding a second polypeptide of interest and a second selectable marker, and (iii) at least one anti-repressor sequence, chosen from the group consisting of (a) any one of SEQ. ID. NO. 1-66, (b) fragments of any one of SEQ. ID. NOs. 1-66, said fragments having anti-repressor activity, (c) sequences that are at least 70% identical to (a) or (b) and having anti-repressor activity, and (d) the complement of any one of (a)-(c); b) selecting a host cell by essentially simultaneously selecting for expression of said first and second selectable marker genes. The selected host cells can be conveniently used for the expression of said two polypeptides, by culturing said selected host cells. In one embodiment, two nucleic acid molecules, one containing (i) and the other containing (ii), are used for introduction into the host cell. In this embodiment, each nucleic acid molecule preferably contains at least one said anti-repressor sequence. In another embodiment, a single nucleic acid molecule containing both (i) and (ii) is used, which must then contain at least one said anti-repressor sequence. One advantage of having the coding sequences for both polypeptides on a single nucleic acid molecule is that only one nucleic acid preparation is required before the nucleic acid is introduced into the cells. Furthermore, in such an embodiment a single integration event is sufficient for the coding sequences of both polypeptides, thereby eliminating the possibility that the nucleic acid encoding the first polypeptide is integrated on a different location or with a different copy number than that encoding the second polypeptide. In preferred embodiments, said two polypeptides may form part of a multimeric protein, such as an immunoglobulin. The method is therefore particularly suited for the expression of antibodies. The two promoters may be the same or different, and could be any promoters as described supra. When the embodiment where a single nucleic acid molecule contains both (i) and (ii) is used, the direction of the two transcription units on the single nucleic acid molecule may for instance be both the same, or in opposite directions facing each other, or in opposite directions each pointing outward. In the latter case, the anti-repressor sequence may be placed between the two promoters (e.g. see FIG. 11B). One suitable anti-repressor sequence for this aspect of the invention is SEQ. ID. NO. 66 (see example 7), but the other anti-repressor sequences may function as well. This can be easily tested by the person skilled in the art, using the disclosure herein, and hence also the use of other anti-repressor sequences according to this aspect of the invention is encompassed by the scope of the invention. Furthermore, anti-repressor sequences may be added to flank one or both transcription units. The marker genes must each be different, and may for instance be selected from the marker genes as described supra. In certain embodiments, one selectable marker is zeocin, and the other selectable marker is for instance puromycin. However, it will be clear that other combinations may be used, and are within the scope of this aspect of the invention. Expression of the markers should preferably be dependent from the expression of the polypeptides of interest. This can be established by linking the expression of the marker genes to that of the polypeptides of interest for instance by using multicistronic genes, e.g. with IRES sequences, as discussed supra. "Essentially simultaneous" selection means that at least part of the time, preferably at least one day, more preferably at least two days, still more preferably at least 5 days, both selection agents are present, which can be brought about by having both selection agents added to the culture medium at the same time or adding culture medium comprising both selection agents (e.g. example 7). It will be clear that adding the second selection agent only after a few hours or days to medium wherein the first selection agent is already present, will still result in essentially simultaneous selection within the meaning of the invention. This situation is distinguished from the situation where cells are first selected with the first selection agent, and once colonies are formed the cells are selected on new medium whereto the second selection agent and not the first selection agent has been added (consecutive selection, e.g. example 5 and WO 03/106684). By selecting for both selectable markers essentially simultaneously, it is disclosed herein surprisingly that a fast and strong selection is provided, whereby many low-producing clones are eliminated, resulting in a strongly decreased workload for finding a clone with desirable expression characteristics. This is particularly advantageous for the biotechnological industry, where many, usually hundreds or even thousands, of colonies have to be screened before a desired clone having high expression levels is identified.

In addition, the system provides the possibility to test parts of anti-repressor elements, at least of STAR67 but also of other anti-repressor sequences when they function in this setting, for functionality. This easy screen, which provides an almost or even complete black and white difference in many cases, therefore will contribute to identifying functional parts or derivatives from anti-repressor sequences, and/or aid in characterizing novel anti-repressor sequences. The screen could even be used to find novel anti-repressor and/or expression-enhancing sequences (since this type of screen is not literally selecting for anti-repressor activity, but rather for expression-enhancing activity, it is also possible that sequences having the latter but not the former activity will be found). It is therefore another aspect of the present invention to provide a method for identifying an anti-repressor and/or expression-enhancing sequences, or a functional fragment or derivative thereof, comprising: a) introducing into a host cell one or more nucleic acid molecules, the nucleic acid molecule or molecules together comprising: (i) a promoter functionally linked to a first selectable marker gene, and (ii) a promoter functionally linked to a second selectable marker, and (iii) at least one sequence to be tested for anti-repressor and/or expression-enhancing activity; b) selecting a host cell by selecting essentially simultaneously for expression of said first and second selectable marker genes. Host cells that survive this screen are likely to contain a functional anti-repressor and/or expression-enhancing element. This can then easily be analysed further, e.g. by determining its sequence and/or by subjecting it to other functional tests for anti-repressor activity as described supra. In one embodiment, both (i) and (ii) are on one nucleic acid molecule, e.g. with diverging promoters (the first and second selectable marker genes facing outward), between which the to be tested sequence can be cloned for analysis. Preferably, said selectable marker genes are not highly expressed, e.g. by using relatively weak promoters directly driving the selectable marker genes, which relatively weak promoters are known to and/or can be identified with routine assays by the person skilled in the art, or for instance by using a strong promoter for transcription and an IRES, preferably a relatively weak IRES as described supra, for translation of the marker gene. The marker genes may also conveniently be placed downstream of nucleic acid sequences encoding a polypeptide and linked to the expression thereof in a multicistronic gene, e.g. by an IRES (e.g. example 7, FIG. 11 for possible configuration). Such polypeptides could again be polypeptides of interest, so that directly useful clones for expression of said polypeptides of interest are obtained, but could for screening purposes also be markers of which expression can easily be quantified, e.g. GFP or a derivative thereof, SEAP, lacZ, luciferase, etc. In such a combination, the expression of the polypeptides could directly be quantified to pick out anti-repressor and/or expression-enhancing elements or fragments thereof that provide sufficient colonies during the simultaneous selection, and also provide high transcription levels. When 'random' nucleic acid (i.e. nucleic acid not yet known to have anti-repressor or expression-enhancing activity), e.g. in the form of genome fragments, is used as the sequence to be tested for anti-repressor and/or expression-enhancing activity, novel anti-repressor and/or expression-enhancing sequences can be found. When known anti-repressor sequences are tested, this assay can be used to characterize them further. When fragments of known anti-repressor sequences are tested, the assay will provide functional fragments of such known anti-repressor sequences.

The practice of this invention will employ, unless otherwise indicated, conventional techniques of immunology, molecular biology, microbiology, cell biology, and recombinant DNA, which are within the skill of the art. See e.g. Sambrook, Fritsch and Maniatis, Molecular Cloning: A Laboratory Manual, 2$^{nd}$ edition, 1989; Current Protocols in Molecular Biology, Ausubel F M, et al, eds, 1987; the series Methods in Enzymology (Academic Press, Inc.); PCR2: A Practical Approach, MacPherson M J, Hams B D, Taylor G R, eds, 1995; Antibodies: A Laboratory Manual, Harlow and Lane, eds, 1988.

The invention is further explained in the following examples. The examples do not limit the invention in any way. They merely serve to clarify the invention.

EXAMPLES

Example 1

Construction of STAR67 Vectors

A novel anti-repressor sequence was isolated using a genetic screen as described in WO 03/004704, and this novel sequence was coined STAR67 (SEQ. ID. NO. 66). The effects of STAR67 on expression of transgenes in mammalian cell lines were tested. Here we describe the construction of the various constructs.

Materials and Methods

Three plasmids were created (FIG. 1):
A) CMV-d2EGFP-ires-Zeo (CMV Control),
B) STAR67-CMV-d2EGFP-ires-Zeo (CMV-STAR67),
C) STAR7-STAR67-CMV-d2EGFP-ires-Zeo-STAR7 (CMV-STAR67 7/7)

The construction of construct A is described below. Plasmid pd2EGFP (Clontech 6010-1) was modified by insertion of a linker at the BsiWI site to yield pd2EGFP-link. The linker, made by annealing oligonucleotides GTACGGATAT-CAGATCTTTAATTAAG (SEQ. ID. NO. 67) and GTACCT-TAATTAAAGATCTGATAT (SEQ. ID. NO. 68), introduced sites for the PacI, BglII, and EcoRV restriction endonucleases. This created the multiple cloning site MCSII for insertion of STAR elements. Then primers GATCA-GATCTGGCGCGCCATTTAAATCGTCTCGCGCGTTT-CGGTGATGACGG (SEQ. ID. NO. 69) and (AGGCG-GATCCGAATGTATTTAGAAAAATAAACAAATAGGGG (SEQ. ID. NO. 70) were used to amplify a region of 0.37 kb from pd2EGFP, which was inserted into the BglII site of pIRES (Clontech 6028-1) to yield pIRES-stuf. This introduced sites for the AscI and SwaI restriction endonucleases at MCSI, and acts as a "stuffer fragment" to avoid potential interference between STAR elements and adjacent promoters. pIRES-stuf was digested with BglII and FspI to liberate a DNA fragment composed of the stuffer fragment, the CMV promoter, the IRES element (flanked by multiple cloning sites MCS A and MCS B), and the SV40 polyadenylation signal. This fragment was ligated with the vector backbone of pd2EGFP-link produced by digestion with BamHI and StuI, to yield pIRES-link.

The open reading frame of the zeocin-resistance gene was inserted into BamHI/NotI sites downstream of the pIRES as follows: the zeocin-resistance ORF was amplified by PCR with primers GATCGGATCCTTCGAAATGGCCAAGT-TGACCAGTGC (SEQ. ID. NO. 71) and AGGCGCGGCCG-CAATTCTCAGTCCTGCTCCTC (SEQ. ID. NO. 72) from plasmid pCMV/zeo (Invitrogen, cat. no. V50120), digested with BamHI and NotI, and ligated with BamHI/NotI-digested pIRES-link to yield pIRES-link-zeo. The d2EGFP reporter ORF was introduced into pIRES-link-zeo by amplification of pd2EGFP (Clontech 6010-1) with primers GATCGAAT-TCTCGCGAATGGTGAGCAAGCAGATCCTGAAG (SEQ. ID. NO. 73) and AGGCGAATTCACCGGTGTT-TAAACTTACACCCACTCGTGCAGGCTGCCCAGG (SEQ. ID. NO. 74), and insertion of the EcoRI-digested d2EGFP cassette into the EcoRI site in the pIRES-link-zeo plasmid. This created construct A, CMV-d2EGFP-IRES-Zeo (CMV Control).

STAR67 was cloned upstream of the CMV promoter, in the AscI site (about 15 nt remaining between STAR67 and the promoter). This created construct B, STAR67-CMV-d2EGFP-ires-Zeo (CMV-STAR67).

STAR67 was also tested in the context of a cassette that contains also the STAR7 (SEQ. ID. NO. 7), cloned directionally in the 5' SalI and XbaI sites and 3' BglII and PacI sites to flank the entire cassette with STAR7. This is construct C (CMV-STAR67 7/7).

Example 2

STAR67 Enhances the Expression Level from CMV, EF1α and UB6 Promoters in Stably Transfected CHO Cells We tested whether the presence of STAR67 adjacent to the CMV, EF1α and UB6 promoters influences the expression level of these promoters in CHO cells. The constructs A and B (FIG. 1) described in Example 1 are used for this purpose, modified for the respective promoters:
1 CMV-d2EGFP-ires-Zeo (CMV Control)
2 STAR67-CMV-d2EGFP-ires-Zeo (CMV-STAR67)
3 EF1α-d2EGFP-ires-Zeo (EF1α Control)
4 STAR67-EF1α-d2EGFP-ires-Zeo (EF1α-STAR67)
5 UB6-d2EGFP-ires-Zeo (UB6 Control)
6 STAR67-UB6-d2EGFP-ires-Zeo (UB6-STAR67).

Materials and Methods

The UB6 and EF1α promoters were exchanged for the CMV promoter in the plasmids described in FIG. 1. The UB6 promoter was cloned as follows. A DNA 0.37 kb stuffer from the pd2EGFP plasmid was amplified by PCR, as described in example 1, using primers identified by SEQ. ID. NOs. 69 and 70. The resulting DNA stuffer was cloned in the BglII site of pUB6/V5-His [Invitrogen V250-20], creating pUB6-stuf. From pUB6-stuf an AscI-SacI fragment was cloned into CMV-d2EGFP-IRES-Zeo, from which the CMV promoter was removed.

The EF1α promoter was amplified by PCR with pEF1α/V5-His [Invitrogen V920-20] as template, using primers GATCGGCGCGCCATTTAAATCCGAAAAGTGCCACC-TGACG (SEQ. ID. NO. 79) and AGGCGGGACCCCCT-CACGACACCTGAAATGGAAG (SEQ. ID. NO. 80). The PCR fragment was cloned in the AscI and PpuMI sites of CMV-d2EGFP-IRES-Zeo, from which the CMV promoter was removed.

The Chinese Hamster Ovary cell line CHO-K1 (ATCC CCL-61) was cultured in HAMS-F12 medium+10% Fetal Calf Serum containing 2 mM glutamine, 100 U/ml penicillin, and 100 micrograms/ml streptomycin at 37° C./5% $CO_2$. Cells were transfected with the plasmids using SuperFect (QIAGEN) as described by the manufacturer. Briefly, cells were seeded to culture vessels and grown overnight to 70-90% confluence. SuperFect reagent was combined with plasmid DNA at a ratio of 6 microliters per microgram (e.g. for a 10 cm Petri dish, 20 micrograms DNA and 120 microliters SuperFect) and added to the cells. After overnight incubation the transfection mixture was replaced with fresh medium, and the transfected cells were incubated further. After overnight cultivation, cells were trypsinized and seeded into fresh culture vessels with fresh medium. After another overnight incubation zeocin was added to a concentration of 50 μg/ml and the cells were cultured further. After another three days the medium was replaced by fresh medium containing zeocin (100 μg/ml) and cultured further. When individual colonies became visible (approximately ten days after transfection) medium was removed and replaced with fresh medium without zeocin. Individual clones were isolated and transferred to 24-well plates in medium without zeocin. One day after isolation of the colonies zeocin was added to the medium. Expression of the d2EGFP reporter gene was assessed approximately 3 weeks after transfection. d2EGFP expression levels in the colonies were measured after periods of two weeks. After the initial two weeks after transfection when the first d2EGFP measurements were performed, the colonies were cultured in medium without zeocin or other antibiotics. This continued for the remainder of the experiment.

Results

FIG. 2 shows that transfection of the construct that contains STAR67 cloned upstream of the CMV promoter resulted in a number of CHO colonies that express significantly higher levels of d2EGFP protein, as compared to the "empty" control without STAR67, CMV Control. The average of the d2EGFP signal in the 10 colonies transfected with the CMV Control plasmid was 34, when measured 25 days after transfection. 60 days after transfection the average of the d2EGFP signal in these 10 colonies was reduced to 13, indicating that expression is not stable over time. In comparison, the average of the d2EGFP signal in the 10 colonies transfected with the STAR67-CMV plasmid was 42 when measured after 25 days and 32 measured 60 days after transfection. Hence 60 days after transfection, a STAR67-encompassing CMV construct conveyed a factor 2.5 higher CMV promoter driven expression level of the reporter protein in stably transfected clones. Importantly, 25 days after transfection, after the first measurement, selection pressure was removed by culturing the colonies in medium without zeocin. Hence, colonies containing the STAR67 construct are more stable over time in the absence of selection pressure than colonies that do not contain a STAR67 construct.

FIG. 3 shows that transfection of the construct that contains STAR67 cloned upstream of the EF1α-promoter resulted in a number of CHO colonies that express significantly higher levels of d2EGFP protein, as compared to the "empty" control without STAR67, EF1α Control. The average of the d2EGFP signal in the 10 colonies transfected with the EF1α Control plasmid was 31, when measured 25 days after transfection. 60 days after transfection the average of the d2EGFP signal in these 10 colonies was 26. In comparison, the average of the d2EGFP signal in the 10 colonies transfected with the EF1α-STAR67 plasmid was 60 when measured after 25 days and 76 measured 60 days after transfection. Hence, both after 25 and 60 days after transfection, a STAR67-encompassing EF1α construct conveyed a factor 2.9 higher EF1α promoter driven expression level of the reporter protein in stably transfected clones.

FIG. 4 shows that transfection of the construct that contains STAR67 cloned upstream of the UB6 promoter resulted in a number of CHO colonies that express significantly higher levels of d2EGFP protein, as compared to the "empty" control without STAR67, UB6 Control. The average of the d2EGFP signal in the 10 colonies transfected with the UB6 Control plasmid was 51, when measured 25 days after transfection. 60 days after transfection the average of the d2EGFP signal in these 10 colonies was 29, indicating that the expression was not stable over time. In comparison, the average of the d2EGFP signal in the 10 colonies transfected with the UB6-STAR67 plasmid was 218 when measured after 25 days and 224 measured 60 days after transfection. Hence, 25 days after transfection, a STAR67-encompassing UB6 construct conveyed a factor 4.3 higher UB6 promoter driven expression level of the reporter protein in stably transfected clones. After 60 days this factor was 7.7, due to instability of expression in the control colonies and stability in the UB6-STAR67 colonies. Importantly, 25 days after transfection, after the first measurement, selection pressure was removed by culturing the colonies in medium without zeocin. Hence, colonies containing the STAR67 construct are more stable over time in the absence of selection pressure than colonies that do not contain a STAR67 construct.

In conclusion, STAR67 increases expression from three different, unrelated promoters.

Example 3

STAR67 Enhances the Expression Level from CMV, EF1α and UB6 Promoters in Stably Transfected PER.C6 Cells We tested whether the presence of STAR67 adjacent of the CMV, EF1α and UB6 promoters influences the expression level of these promoters in another cell type than CHO cells, namely human PER.C6 cells. The same constructs as in example 1 were used.

Materials and Methods

Transfection, culturing and analysis of PER.C6 cells PER.C6® cells were cultured in DMEM medium+pyridoxine+9% Foetal Bovine Serum (Non-Heat Inactivated), 8.9 mM $MgCl_2$ 100 U/ml penicillin, and 100 micrograms/ml streptomycin at 37° C./10% $CO_2$. Cells were transfected with the plasmids using Lipofectamine 2000 (Invitrogen) as described by the manufacturer. Briefly, cells were seeded to 6-wells and grown overnight to 70-90% confluence. Lipofectamine reagent was combined with plasmid DNA at a ratio of 15 microliters per 3 microgram (e.g. for a 10 cm Petri dish, 20 micrograms DNA and 120 microliters Lipofectamine) and added after 30 minutes incubation at 25° C. to the cells. After 6-hour incubation the transfection mixture was replaced with fresh medium, and the transfected cells were incubated further. After overnight cultivation, cells were trypsinized and seeded (1:15, 1:30, 1:60, 1:120 dilutions) into fresh petri dishes (90 mm) with fresh medium with zeocin added to a concentration of 100 μg/ml and the cells were cultured further. When colonies became visible, individual clones were isolated by scraping and transferred to 24-well plates in medium with zeocin. When grown to ~70% confluence, cells were transferred to 6-well plates. Stable colonies were expanded for 2 weeks in 6-well plates before the d2EGFP signal was determined on a XL-MCL Beckman Coulter flow-cytometer. The mean of the d2EGFP signal was taken as measure for the level of d2EGFP expression. Colonies were measured for a second time after 2 weeks. Thereafter colonies were further cultured in the absence of zeocin.

Results

FIG. 5 shows that transfection of the construct that contains STAR67 cloned upstream of the CMV promoter resulted in a number of PER.C6 colonies that express significantly higher levels of d2EGFP protein, as compared to the "empty" control without STAR67, CMV Control. The average of the d2EGFP signal in the 10 colonies transfected with the CMV Control plasmid was 37, when measured 30 days after transfection. 60 days after transfection the average of the d2EGFP signal in these 10 colonies was reduced to 14, indicating that expression was not stable over time. In comparison, the average of the d2EGFP signal in the 10 colonies transfected with the STAR67-CMV plasmid was 101 when measured after 30 days and 45 measured 60 days after transfection. Hence 60 days after transfection, a STAR67-encompassing CMV construct conveyed a factor 3.2 higher CMV promoter driven expression level of the reporter protein in stably transfected clones.

FIG. 6 shows that transfection of the construct that contains STAR67 cloned upstream of the EF1α-promoter resulted in a number of PER.C6 colonies that express significantly higher levels of d2EGFP protein, as compared to the "empty" control without STAR67, EF1α Control. The average of the d2EGFP signal in the 10 colonies transfected with the EF1α Control plasmid was 5, when measured 30 days after transfection. 60 days after transfection the average of the d2EGFP signal in these 10 colonies was 6. In comparison, the average of the d2EGFP signal in the 10 colonies transfected with the EF1α-STAR67 plasmid was 25 when measured after 30 days and 20 measured 60 days after transfection. Hence, both after 30 and 60 days after transfection, a STAR67-encompassing EF1α construct conveyed a factor 4 higher EF1α promoter driven expression level of the reporter protein in stably transfected clones.

FIG. 7 shows that transfection of the construct that contains STAR67 cloned upstream of the UB6 promoter resulted in a number of PER.C6 colonies that express significantly higher levels of d2EGFP protein, as compared to the "empty" control without STAR67, UB6 Control. The average of the d2EGFP signal in the 10 colonies transfected with the UB6 Control plasmid was 4, when measured 30 days after transfection. 60 days after transfection the average of the d2EGFP signal in these 10 colonies was 2. In comparison, the average of the d2EGFP signal in the 10 colonies transfected with the UB6-STAR67 plasmid was 27 when measured after 30 days and 18 measured 60 days after transfection. Hence, both after 30 and 60 days after transfection, a STAR67-encompassing UB6 construct conveyed a factor 7 to 9 fold higher UB6 promoter driven expression level of the reporter protein in stably transfected clones.

Hence placing STAR67 upstream of the promoter resulted in significantly higher protein expression levels in comparison with STAR67-less constructs, also in PER.C6 cells. Hence STAR67 functions in different, unrelated cell types.

Example 4

Novel Configuration of STAR67 Combined with Other Anti-Repressor Elements to Enhance the SV40 Promoter in CHO Cells We tested whether the presence of STAR67 adjacent of the SV40 promoter influences the expression level of this promoter, either alone or in combination with another anti-repressor element, in this example STAR7. The constructs that were used for this purpose (see FIG. 8), are:
1 SV40-d2EGFP-ires-Zeo (SV40 Control)
2 STAR67-SV40-d2EGFP-ires-Zeo (SV40-STAR67)
3 STAR7-SV40-d2EGFP-ires-Zeo-STAR7 (SV40-STAR7/7)
4 STAR7-STAR67-SV40-d2EGFP-ires-Zeo-STAR7 (SV40-STAR67 7/7)

Materials and Methods

The SV40 promoter was amplified by PCR with pIRES as template using primers TTGGTTGGGGCGCGCCGCAG-CACCATGGCCTGAAATAACCTCTGAAAGAGG (SEQ. ID. NO. 81) and TTGGTTGGGAGCTCAAGCTTTTTG- CAAAAGCCTAGGCCTCCAAAAAAGCCTCCTC (SEQ. ID. NO. 82). The PCR fragment was cloned in the AscI and SacI sites of CMV-d2EGFP-IRES-Zeo, from which the CMV promoter was removed. CHO cells were transfected, colonies were isolated and propagated and analysed as in Example 2.

Results

FIG. 8 shows that transfection of the construct that either contains STAR67 cloned upstream of the SV40 promoter (SV40-STAR67) or STAR7 cloned to flank the entire construct (SV40-STAR 7/7) did not result in CHO colonies that express significantly higher levels of d2EGFP protein, as compared to the "empty" control without anti-repressor elements (SV40 Control). The average of the d2EGFP signal in the 18 colonies transfected with the SV40 Control plasmid was 86, when measured 40 days after transfection. In comparison, the average of the d2EGFP signal in the 18 colonies transfected with the SV40-STAR67 plasmid was 82 when measured after 40 days and the average of the d2EGFP signal in the 18 colonies transfected with the SV40-STAR 7/7 plasmid was 91 when measured after 40 days. Hence, no significant effect of these anti-repressor elements on the SV40 promoter in CHO cells was observed.

It appears that the expression levels from the SV40 promoter in these cells are already quite high, and even much higher than those observed with the CMV promoter, which was considered to be a very strong promoter. This high background expression in the absence of an anti-repressor element using the SV40 promoter in CHO cells, may explain why no significant effect of STAR67 alone, or STAR7 flanking the transgene, was observed.

However, the average of the d2EGFP signal in the 18 colonies transfected with the SV40-STAR67 7/7 plasmid was 209 when measured after 40 days colonies, which is a factor 2.4 higher than the average of the 18 control colonies (86). Hence, when the STAR67 element is used in combination with another anti-repressor element, this results in a number of stably transfected CHO colonies that show significantly higher d2EGFP expression levels.

Therefore in this novel configuration (5'—STAR sequence A—STAR sequence C—promoter—nucleic acid encoding a protein of interest—STAR sequence B—3', wherein in the present example STAR sequences A and B are STAR 7 and STAR sequence C is STAR67) STAR elements appear to function even better than in hitherto disclosed configurations.

We have done experiments in which the flanking STAR7 elements were replaced by flanking STAR6 (SEQ. ID. NO. 6) elements or by flanking STAR4 (SEQ. ID. NO. 4) elements, in combination with STAR67 upstream of the SV40 promoter (SV40-STAR67 6/6 and SV40-STAR67 4/4, respectively, using the same nomenclature as above), and observed improved expression also with these combinations. This proves that the flanking STAR7 elements can be exchanged for other STAR sequences, and still the improvement of the novel configuration of the expression cassette with the STAR sequences is observed.

Example 5

A Combination of STAR67 and STAR7 Enhance UB6-Driven Antibody Expression Levels in Stably Transfected CHO Cells In example 4 we showed that the combination of STAR67 and STAR7 enhanced the expression levels of d2EGFP protein in CHO cells. Here we tested whether the combination of STAR67 and STAR7 could be used for the production of an antibody. We chose an antibody against the EpCAM molecule (Huls et al, 1999) as test protein and used the UB6 promoter.

Materials and Methods

Plasmids

The heavy chain CDNA (HC-EpCAM) was cloned in a construct encompassing the UB6 promoter. The HC-EpCAM was coupled to the Zeocin resistance gene by an IRES sequence. The light chain cDNA (LC-EpCAM) was also cloned in a construct encompassing the UB6 promoter. The LC-EpCAM was coupled to the puromycin resistance gene by an IRES sequence. Together these two plasmids represent the UB6 (HC+LC) Control (FIG. 9)

To test the effects of STAR67 and STAR7, STAR67 was cloned in both HC+LC constructs, upstream of the UB6 promoters. STAR7 was cloned to flank the entire cassettes, both at the 5' and 3' end (FIG. 9). These two plasmids represent STAR7-STAR67-UB6 (HC+LC) STAR7.

Transfection and Culture of CHO Cells

The Chinese Hamster Ovary cell line CHO-K1 (ATCC CCL-61) was transfected and cultured as in example 2, using zeocin (100 µg/ml) and puromycin (2.5 µg/ml) for selection. One day after transfection, zeocin was added to the culture medium. When first colonies became visible (approximately 7 days after addition of zeocin) the culture medium was removed and replaced with culture medium containing puromycin. After approximately 7 days, colonies were isolated and transferred to 24 wells plates, in culture medium containing zeocin only.

Results

FIG. 9 shows that that transfection of antibody constructs that contain STAR67 cloned upstream of the UB6 promoter and two STAR7 elements cloned to flank the entire cassettes resulted in a number of CHO colonies that express significantly higher levels of EpCAM antibody (measured by ELISA using an anti-human IgG antibody) as compared to the "empty" control without STAR67 and STAR7, UB6 (HC+LC) Control. The average of the EpCAM production in the 18 colonies transfected with the UB6 (HC+LC) Control plasmid was 2.7 pg/cell/day, when measured 25 days after transfection. Selection agents zeocin and puromycin were removed after 25 days. 45 days after transfection the average of the EpCAM production in these 18 colonies was 2.7 pg/cell/day. In comparison, the average of the EpCAM production signal in the 18 colonies transfected with the STAR7-STAR67-UB6 (HC+LC)-STAR7 plasmid was 6.7 when measured after 25 days and 7.7 pg/cell/day, when measured 45 days after transfection. Hence, both after 30 and 45 days after transfection, a STAR67/STAR7-encompassing UB6 construct conveyed a factor 2.5 to 2.9 fold higher UB6 promoter driven EpCAM expression level in stably transfected CHO clones.

Hence placing STAR67 upstream of the promoter and two STAR7 elements to flank the cassettes resulted in significantly higher EpCAM antibody expression levels in CHO cells, in comparison with STAR67/STAR7-less constructs.

Example 6

STAR67 is Not an Enhancer Blocker, Whereas STAR6 and STAR7 are

All hitherto known STAR elements that were tested for that property, including STAR6 and STAR7, are enhancer blockers (WO 03/004704, Kwaks et al, 2003). Enhancer blocker activity is tested by placing a STAR element between a strong enhancer and a promoter. Here we tested whether also STAR67 is an enhancer blocker.

Materials and Methods

The d2EGFP gene was PCR-amplified using primers TTG-GTTGGTCATGAATGGTGAGCAAGGGCGAGGAGCT-GTTC (SEQ. ID. NO. 75) and ATTCTCTAGACTACACAT-TGATCCTAGCAGAAGCAC (SEQ. ID. NO. 76) and cloned into plasmid pGL3-promoter (Promega) using the NcoI and XbaI restriction sites to replace the Luciferase gene to create plasmid pGL3-promoter-GFP. A linker (created by annealing oligo's CGATATCTTGGAGATCTACTAGTGGCGCGCC-TTGGGCTAGCT (SEQ. ID. NO. 77) and GATCAGC-TAGCCCAAGGCGCGCCACTAGTAGATCTCCAAGAT-ATCGAGCT (SEQ. ID. NO. 78), was cloned in the SacI and BglII sites to create multiple cloning sites. The original BglII site was destroyed upon ligation of the linker, creating a new unique BglII site within the linker DNA. The SV40-enhancer was cut from plasmid pGL3-basic (Promega) using BsaBI and BamHI and cloned into the pGL3-linker-promoter-GFP using the EcoRV and BglII sites creating plasmid pGL3-enhancer-promoter-GFP. The STAR40 element (SEQ. ID. NO. 40) was placed upstream of the SV40 enhancer using KpnI and SacI sites to prevent action of the enhancer on upstream sequences. Finally, anti-repressor elements STAR6, STAR7 and STAR67 were placed in between the SV40 enhancer and the SV40 minimal promoter using the SpeI and AscI restriction sites.

Transfection and Culture of CHO Cells

The Chinese Hamster Ovary cell line CHO-K1 (ATCC CCL-61) is transfected as in example 2. One day after the transfection, d2EGFP levels are measured on an Epics XL flowcytometer (Beckman Coulter)

Results

FIG. 10 shows that STAR67 is not an enhancer blocker, whereas STAR6 and STAR7 act enhancer blockers in the same assay. STAR6, STAR7 and STAR67 were cloned between the SV40 enhancer and a minimal SV40-promoter upstream of the d2EGFP gene. When no STAR element was cloned between the enhancer and the promoter strong transcriptional activation occurred (arbitrarily set at 100%). When STAR6 or STAR7 was placed between the enhancer and the promoter, transcription dropped to background levels, indicating that STAR6 and STAR7 are potent enhancer blockers. In contrast, when STAR67 was cloned between the enhancer and the promoter relative transcription levels were still 80% of the control, indicating that STAR67 is not a good enhancer blocker, this in contrast with STAR6 and STAR 7, as well as other anti-repressor elements, as previously described (WO 03/004704, Kwaks et al, 2003).

Example 7

STAR67 Enhances UB6 and CMV-Driven Antibody Expression Levels in Stably Transfected CHO Cells In example 5 we showed that the combination of STAR67 and STAR7 enhanced the expression levels of EpCAM antibody in CHO cells, in the context of two distinct plasmids, which contained the heavy and light chains. In this example we tested whether STAR67 could be used for the production of EPCAM antibody when both heavy and light chains are placed on one plasmid. We used simultaneous selection for each selectable marker.

Materials and Methods

Plasmids

The heavy chain cDNA (HC-EpCAM) is under the control of the UB6 promoter and coupled to the Zeocin resistance gene by an IRES sequence. The light chain cDNA (LC-EpCAM) is under control of the CMV promoter and coupled to the puromycin resistance gene by an IRES sequence. Basically these are the constructs used in example 5. These two expression cassettes were placed on one plasmid, in such a manner that transcription of the two expression units had opposite directions. In the control plasmid the UB6 and CMV promoters were separated by a stuffer of 500 bp (EpCAM Control) (FIG. 10). In another plasmid STAR67 was placed between the UB6 and CMV promoter (EpCAM STAR67) (FIG. 10).

Transfection and Culture of CHO Cells

The Chinese Hamster Ovary cell line CHO-K1 (ATCC CCL-61) was transfected and cultured as in example 2, using zeocin (100 µg/ml) and puromycin (2.5 µg/ml) for selection. In example 5, consecutive selection for both selection markers was used. In contrast, here both selection agents were present in the culture medium simultaneously. One day after transfection, zeocin and puromycin were added to the culture medium. The selection medium was present until colonies were isolated (approximately 14 days after transfection). After colonies were isolated and transferred to 24-wells plates, the cells were cultured in the presence of zeocin and puromycin.

Results

FIG. 11 shows that that transfection of the antibody construct that contains STAR67 cloned between the UB6 and CMV promoters resulted in a number of CHO colonies that express EpCAM antibody (measured by ELISA using an anti-human IgG antibody). The average of the EpCAM production in the 19 colonies transfected with the EPCAM STAR67 plasmid was 9.8 pg/cell/day, when measured 25 days after transfection.

In contrast, surprisingly no colonies survived of the transfection with the EpCAM Control plasmid. When selection was performed with either zeocin or puromycin alone, EpCAM Control colonies survived. However, when the selection pressure was increased by placing selection pressure on both the heavy and light chain, these conditions allowed only colonies to survive that have a STAR67 present in the transfected plasmid.

The results also show that incorporation of STAR67 has a beneficial effect on two promoters, the UB6 and CMV promoters, that are placed upstream and downstream of one STAR67 element. This indicates that STAR67 may operate in a bi-directional fashion.

The difference between the EPCAM control and EpCAM STAR67 plasmid is black-white in the sense that only transfection of EpCAM STAR67 results in the establishment of colonies, when the selection pressure is high. This opens an opportunity to use this plasmid configuration for identifying the region in STAR67 that is responsible for mediating this effect. Smaller, overlapping portions of STAR67 are placed between the UB6 and CMV promoters, driving the EpCAM molecule. When a portion of STAR67 is functional, colonies will survive when both zeocin and puromycin are simultaneously used as selection agent. When a portion of STAR67 is not functional, no colonies will survive under identical selection conditions.

Hence placing STAR67 upstream of the promoter resulted in significantly higher EpCAM antibody expression levels in CHO cells, in comparison with constructs lacking such anti-repressor elements.

A similar experiment is performed with the SV40 promoter to drive expression of the heavy and light chains of the anti-EpCAM antibody. In other experiments, STAR67 is exchanged for other STAR sequences. In further experiments, the orientation of the two expression units encoding the heavy and light chains is changed such that both are in the same direction. In another experiment, the expression units for the heavy and light chains are placed on different nucleic acid molecules respectively (as in example 5), and the resulting clones are simultaneously selected for both selectable markers. In another experiment, the host cell type is varied. Combinations of these variations are made.

A) bicistronic gene containing (from 5' to 3') a transgene (encoding for example the d2EGFP gene), an IRES, and a selectable marker (zeo, conferring zeocin resistance) under control of the CMV promoter. The expression unit has the SV40 transcriptional terminator at its 3' end (t). The name of the construct is CMV-d2EGFP-ires-Zeo (CMV Control).

B) construct as in A, but now STAR 67 is cloned upstream of the CMV promoter. The name of the construct is STAR67-CMV-d2EGFP-ires-Zeo (CMV-STAR67).

C) construct as in B, but upstream and downstream STAR7 elements are cloned to flank the entire construct. The name of the construct is STAR7-STAR67-CMV-d2EGFP-ires-Zeo-STAR7 (CMV-STAR67 7/7).

Figure 1:
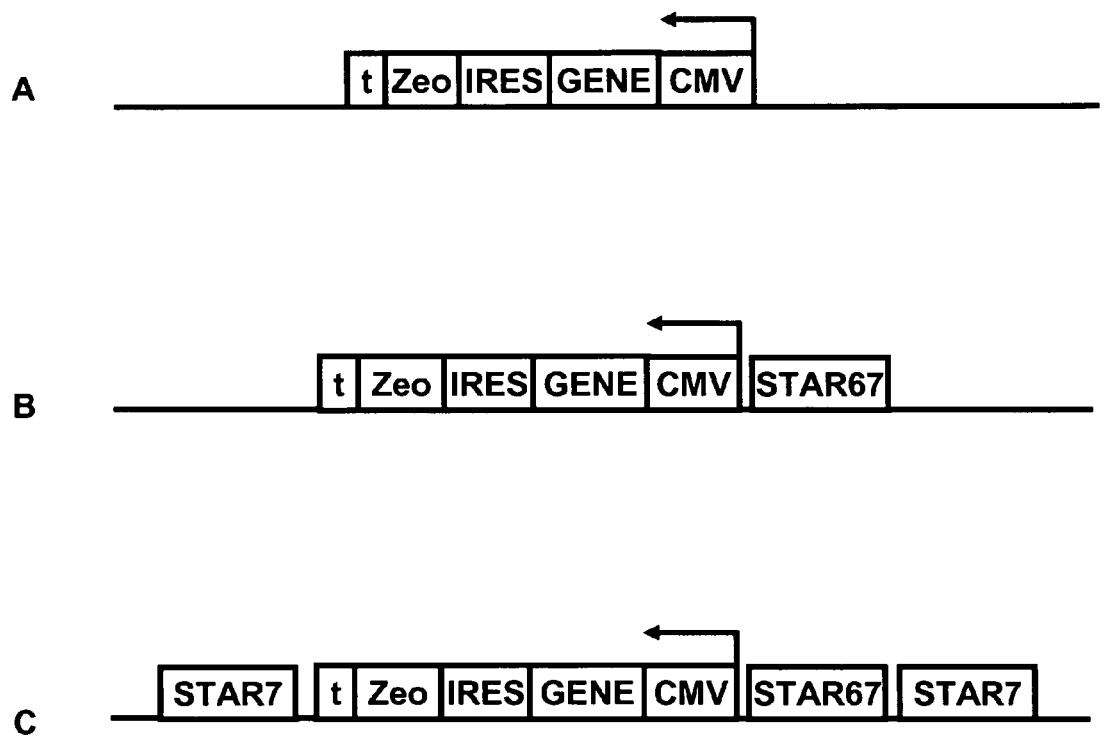
FIG. 1. Schematic diagram of the invention.
Figure 2:
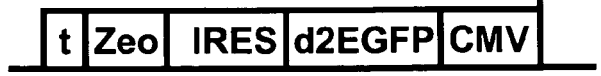
Figure 2:
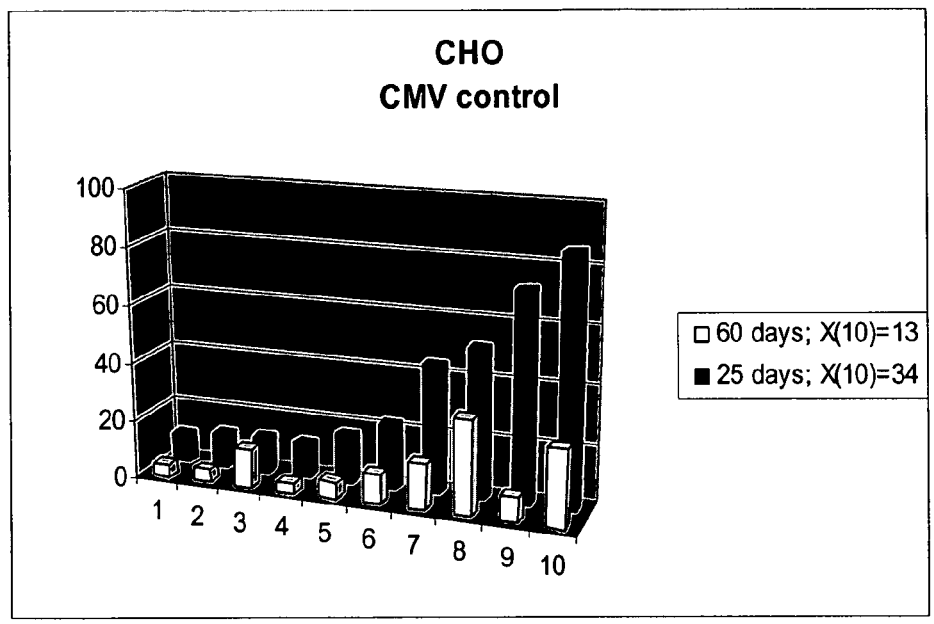
Figure 2:
Figure 2:
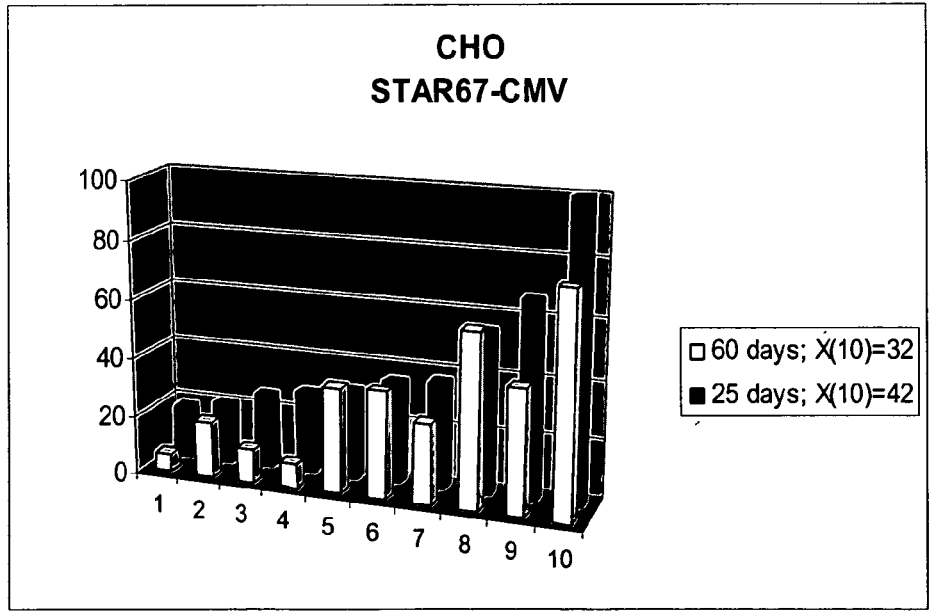

FIG. 2. STAR67 improves CMV driven d2EGFP expression in CHO cells.

The mean of the d2EGFP signal for 10 independent stable colonies is plotted for the indicated constructs in CHO cells. A) CMV Control; B) STAR67-CMV. X(10): average d2EGFP expression levels of the 10 colonies. See example 2 for details.

Figure 3:
Figure 3:
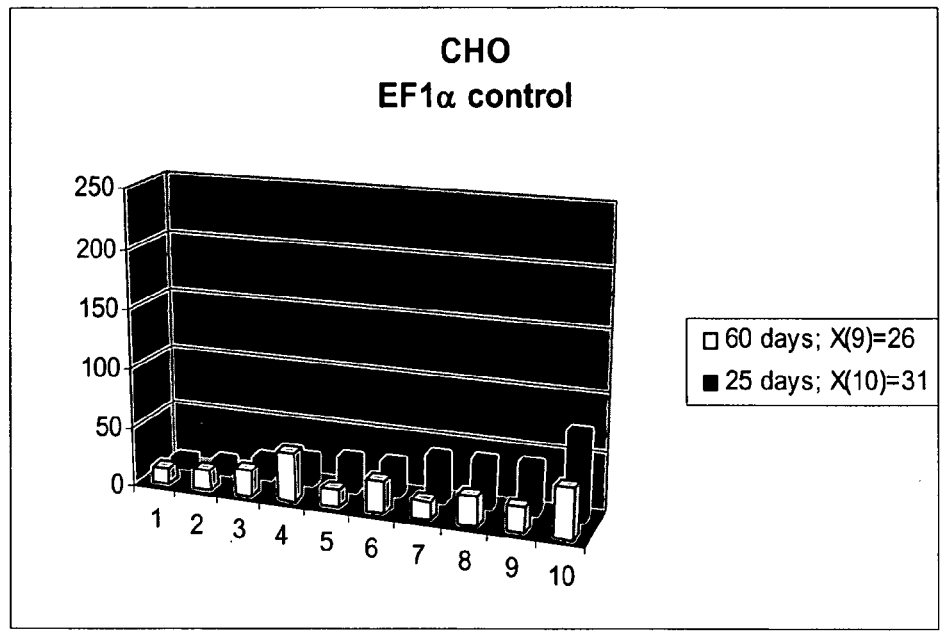
Figure 3:
Figure 3:
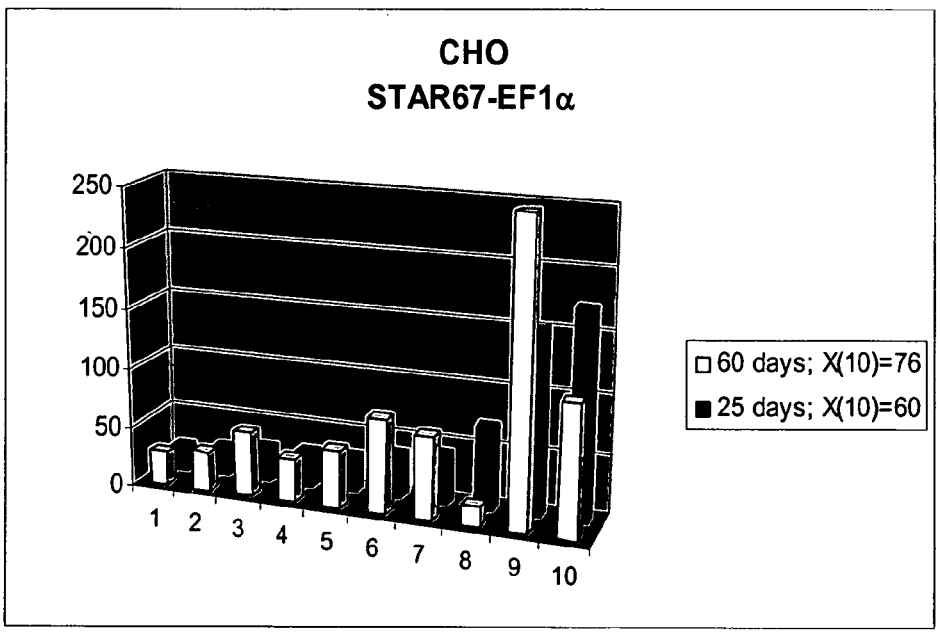

FIG. 3. STAR67 improves EF1α driven d2EGFP expression in CHO cells. Same as FIG. 2, but now with EF1α promoter. A) EF1αControl; B) STAR67-EF1α.

Figure 4:
Figure 4:
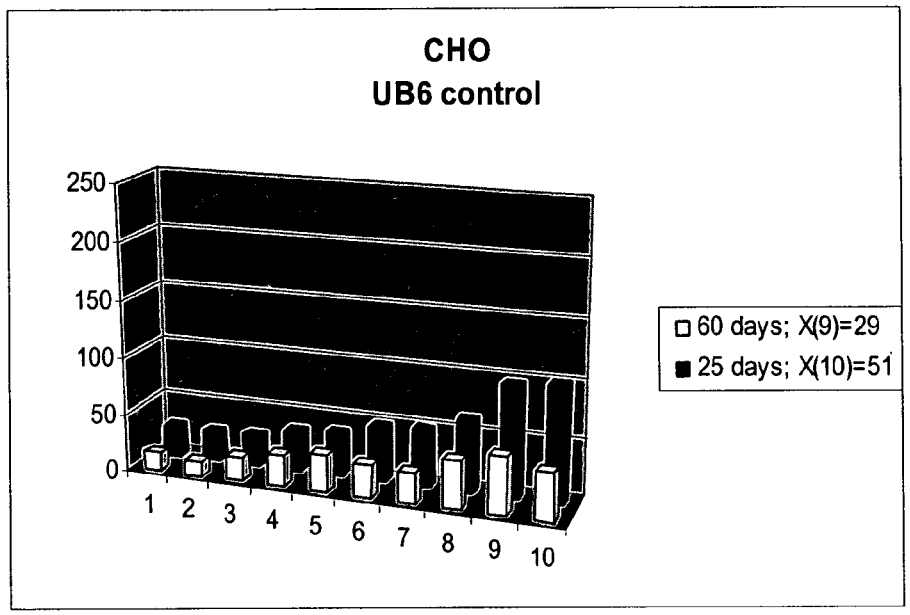
Figure 4:
Figure 4:
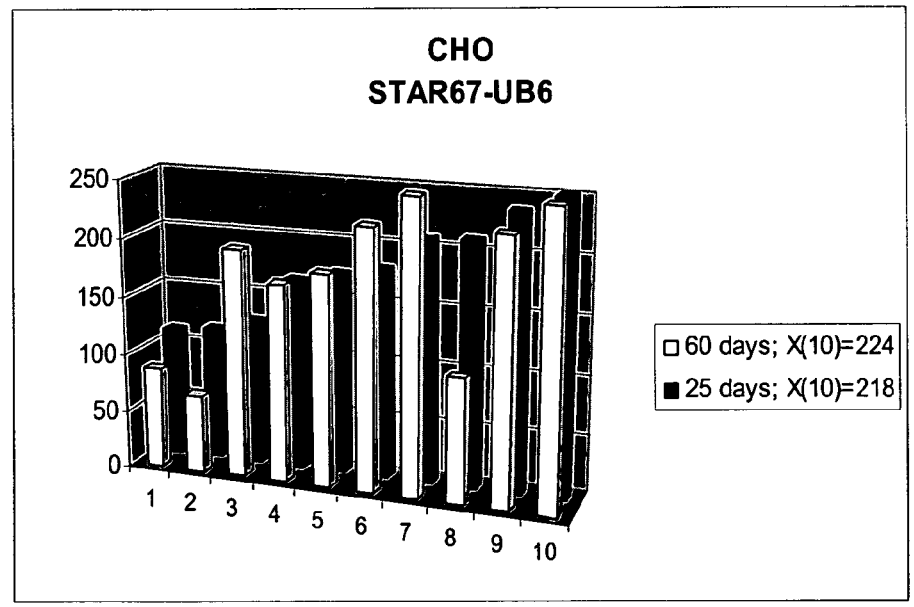

FIG. 4. STAR67 improves UB6 driven d2EGFP expression in CHO cells. Same as FIGS. 2 and 3, but now with UB6 promoter. A) UB6 Control; B) STAR67-UB6.

Figure 5:
Figure 5:
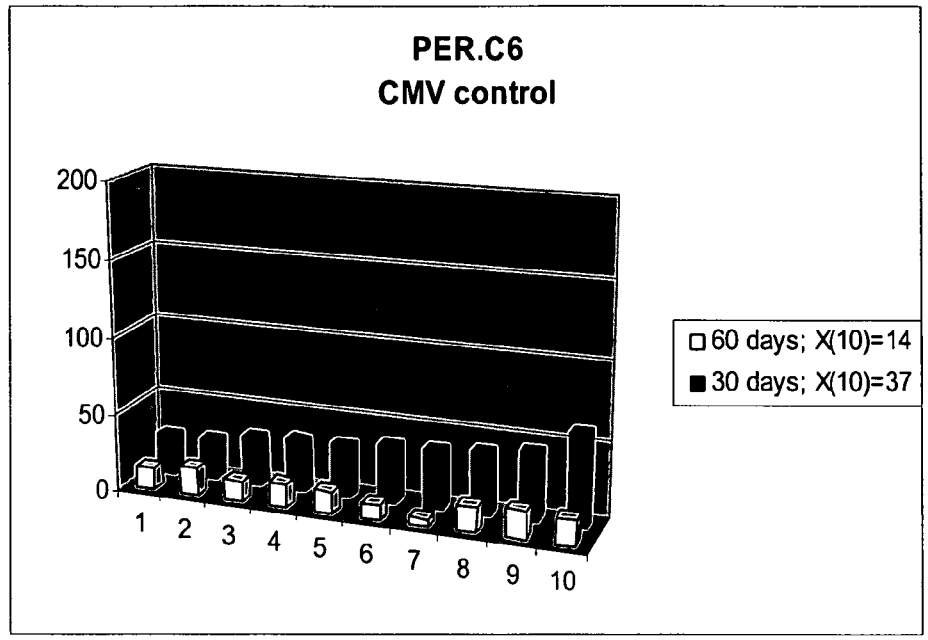
Figure 5:
Figure 5:
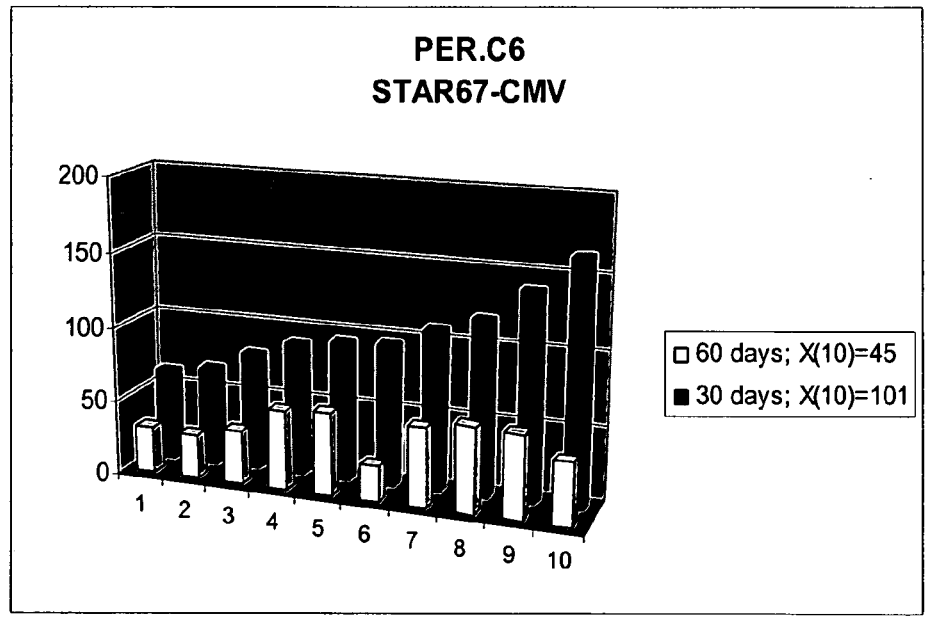

FIG. 5. STAR67 improves CMV driven d2EGFP expression in PER.C6 cells. Same as FIG. 2, but now in PER.C6 cells. A) CMV Control; B) STAR67-CMV.

Figure 6:
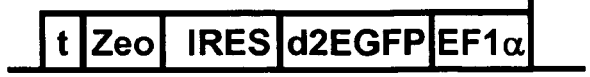
Figure 6:
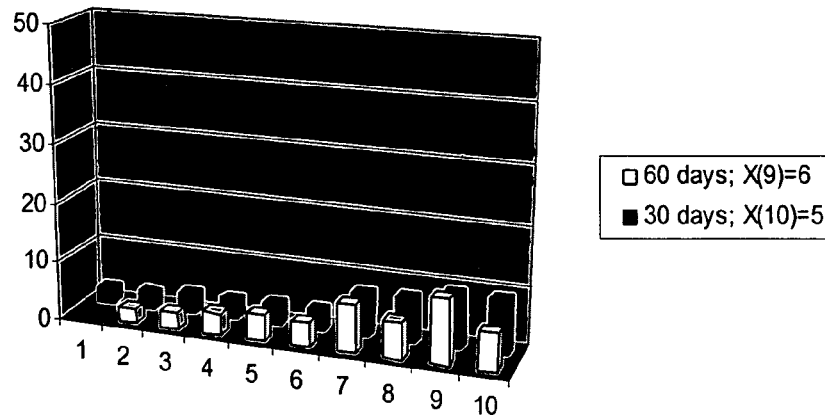
Figure 6:
Figure 6:
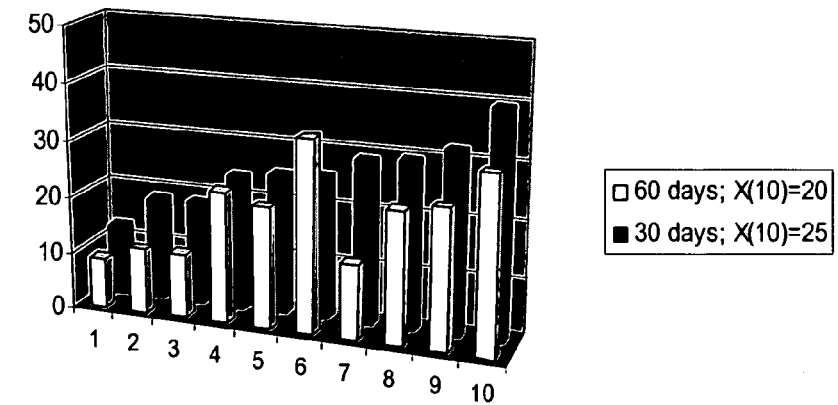

FIG. 6. STAR67 improves EF1α driven d2EGFP expression in PER.C6 cells. Same as FIG. 3, but now in PER.C6 cells. A) EF1 Control; B) STAR67-EF1α.

Figure 7:
Figure 7:
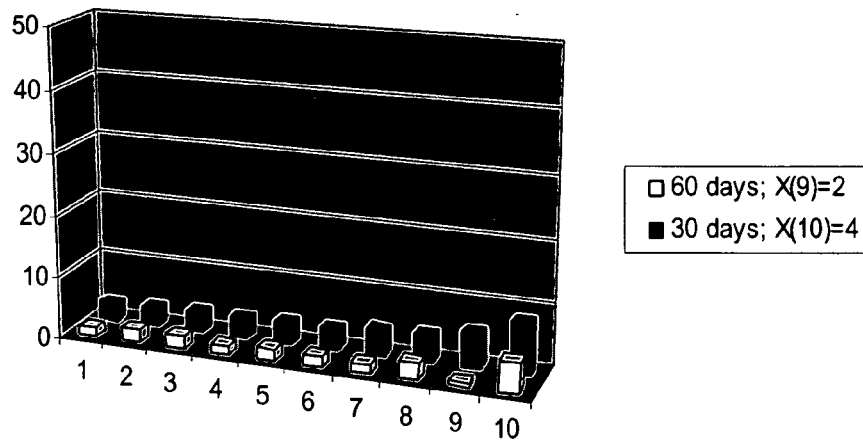
Figure 7:
Figure 7:
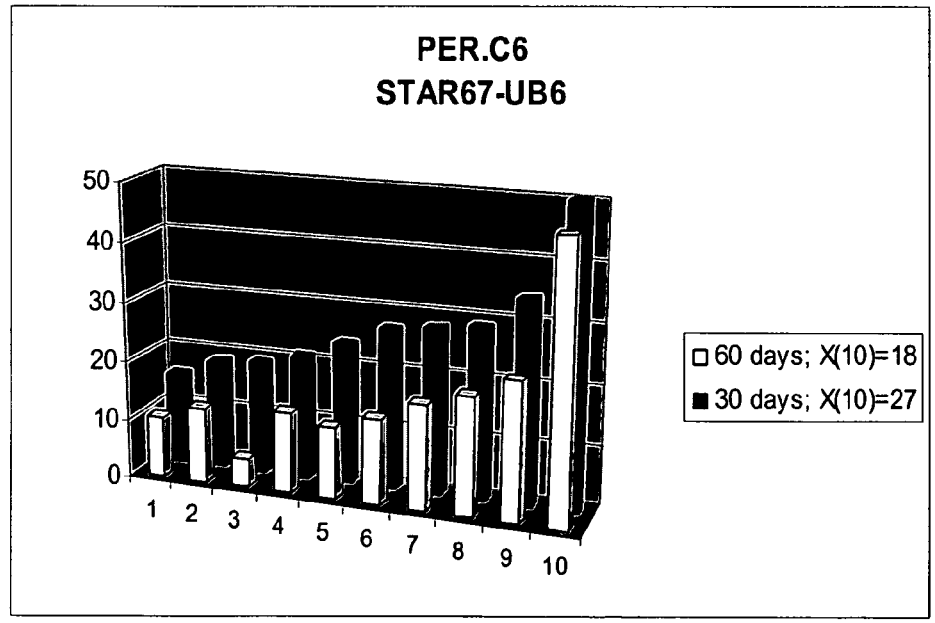

FIG. 7. STAR67 improves UB6 driven d2EGFP expression in PER.C6 cells. Same as FIG. 4, but now in PER.C6 cells. A) UB6 Control; B) STAR67-UB6.

Figure 8:
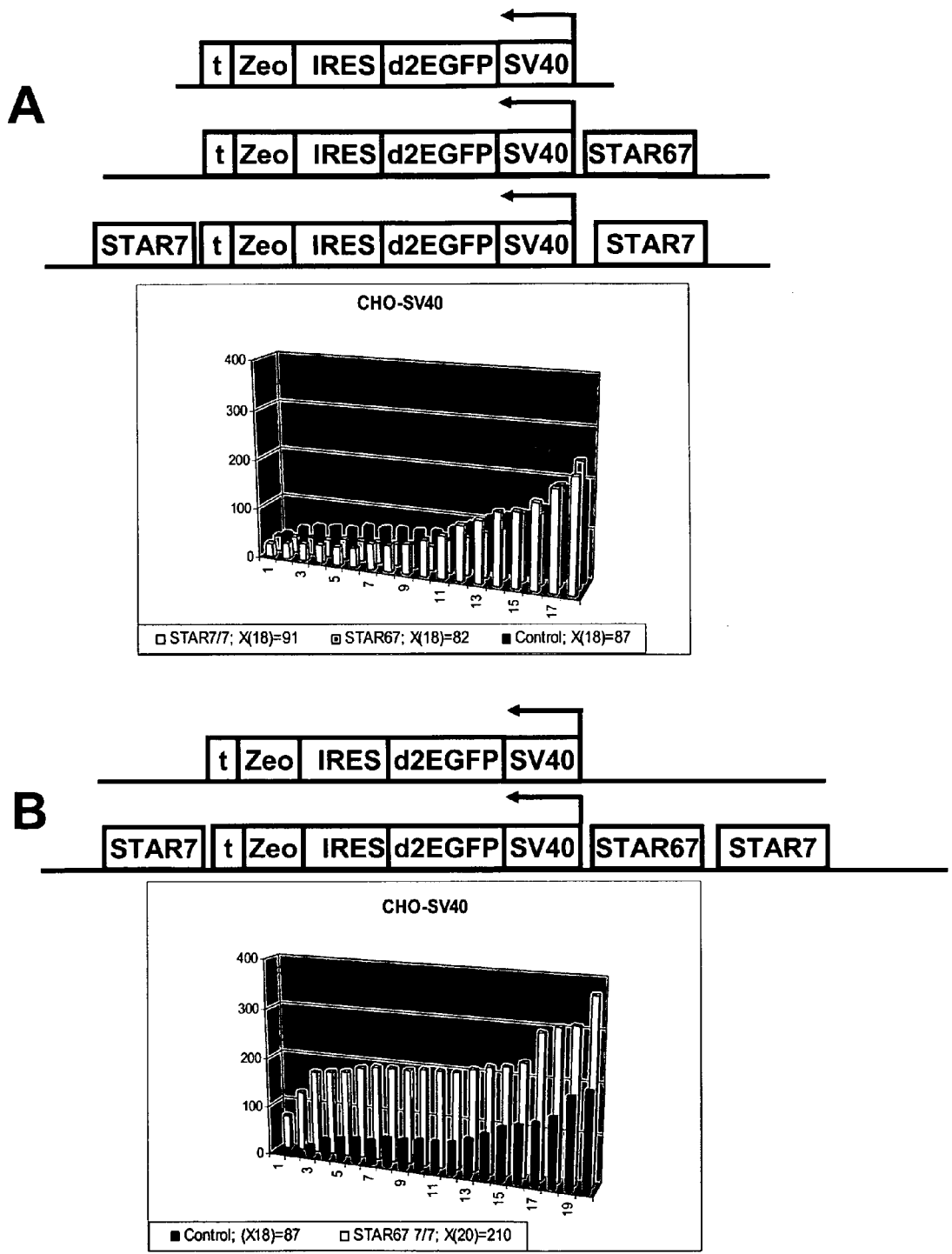

FIG. 8. STAR67 improves SV40 driven d2EGFP expression in CHO-K1 cells in combination with another STAR element. Similar as FIG. 2, but now using the SV40 promoter in CHO cells, and the indicated constructs. The mean of the d2EGFP signal is plotted for 18-20 independent stable colonies 60 days after transfection. A) SV40 Control, SV40-STAR67, SV40-STAR7/7; B) SV40 Control and SV40-STAR67 7/7. See example 4 for details.

Figure 9:
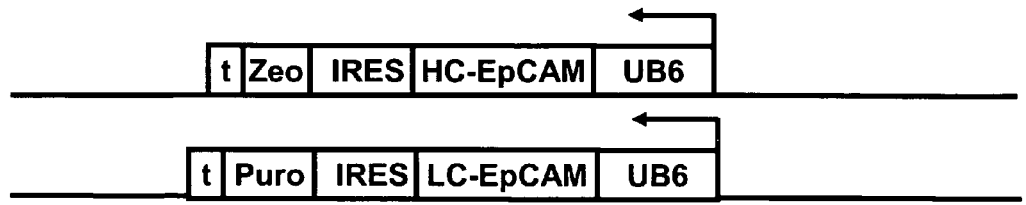
Figure 9:
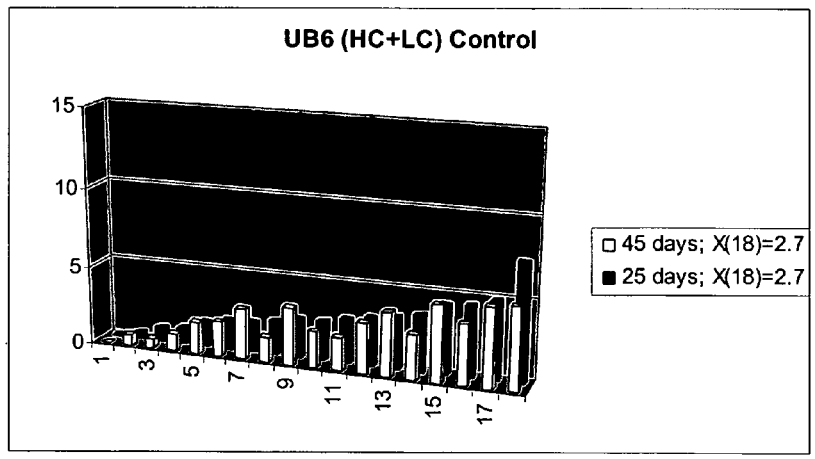
Figure 9:
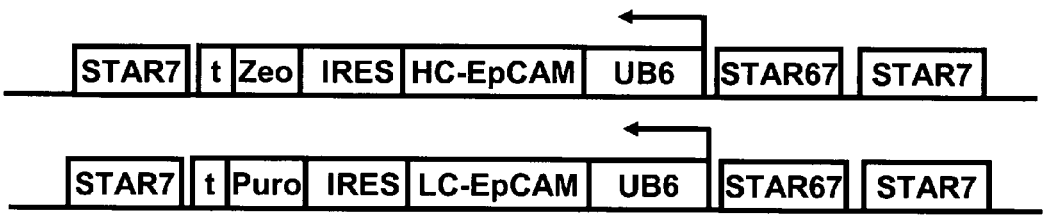
Figure 9:
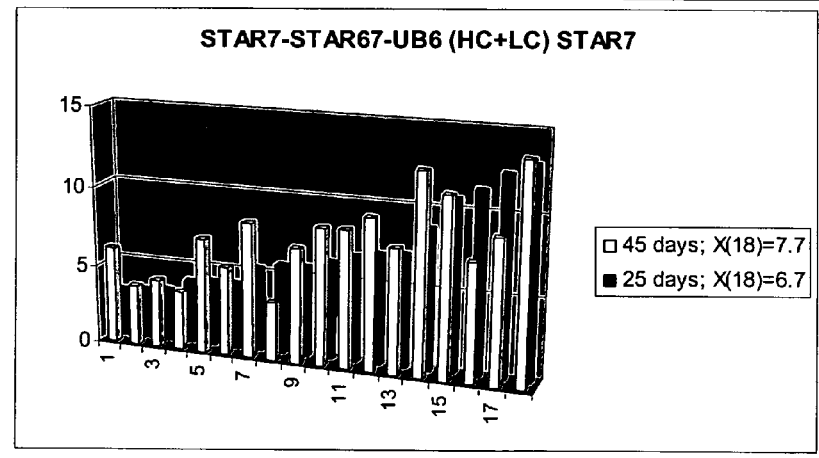

FIG. 9. STAR67 improves UB6 driven expression levels of the EpCAM antibody in CHO-K1 cells. See example 5 for details. A) constructs without STAR elements; B) constructs with STAR67 upstream of promoter and flanking STAR7 elements. The anti-EpCAM antibody concentration is presented as pg/cell/day. X(18): average production level of the 18 colonies.

Figure 10:
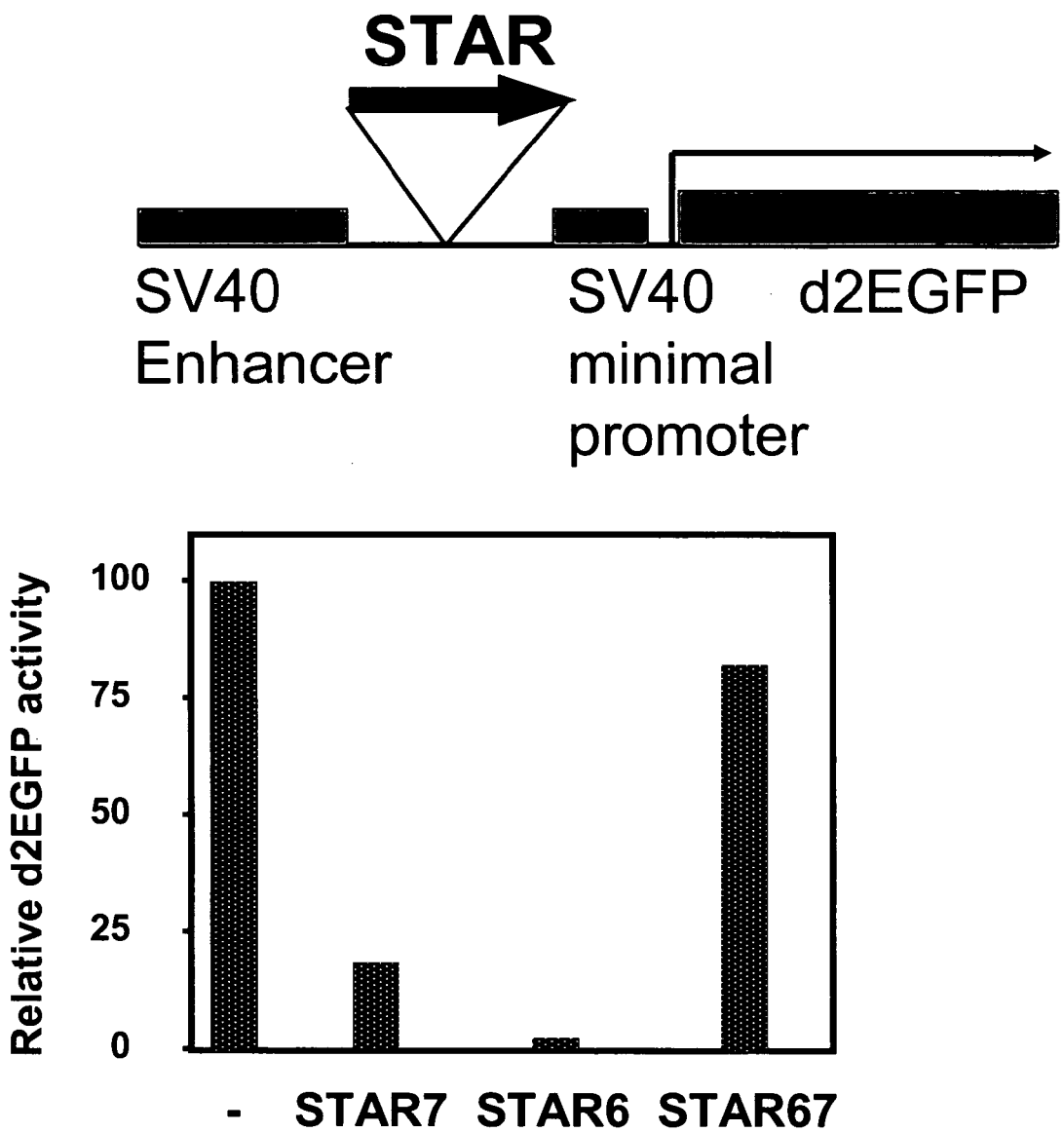

FIG. 10. STAR67 is not an enhancer blocker, whereas STAR 6 and 7 are. See example 6 for details.

Figure 11:
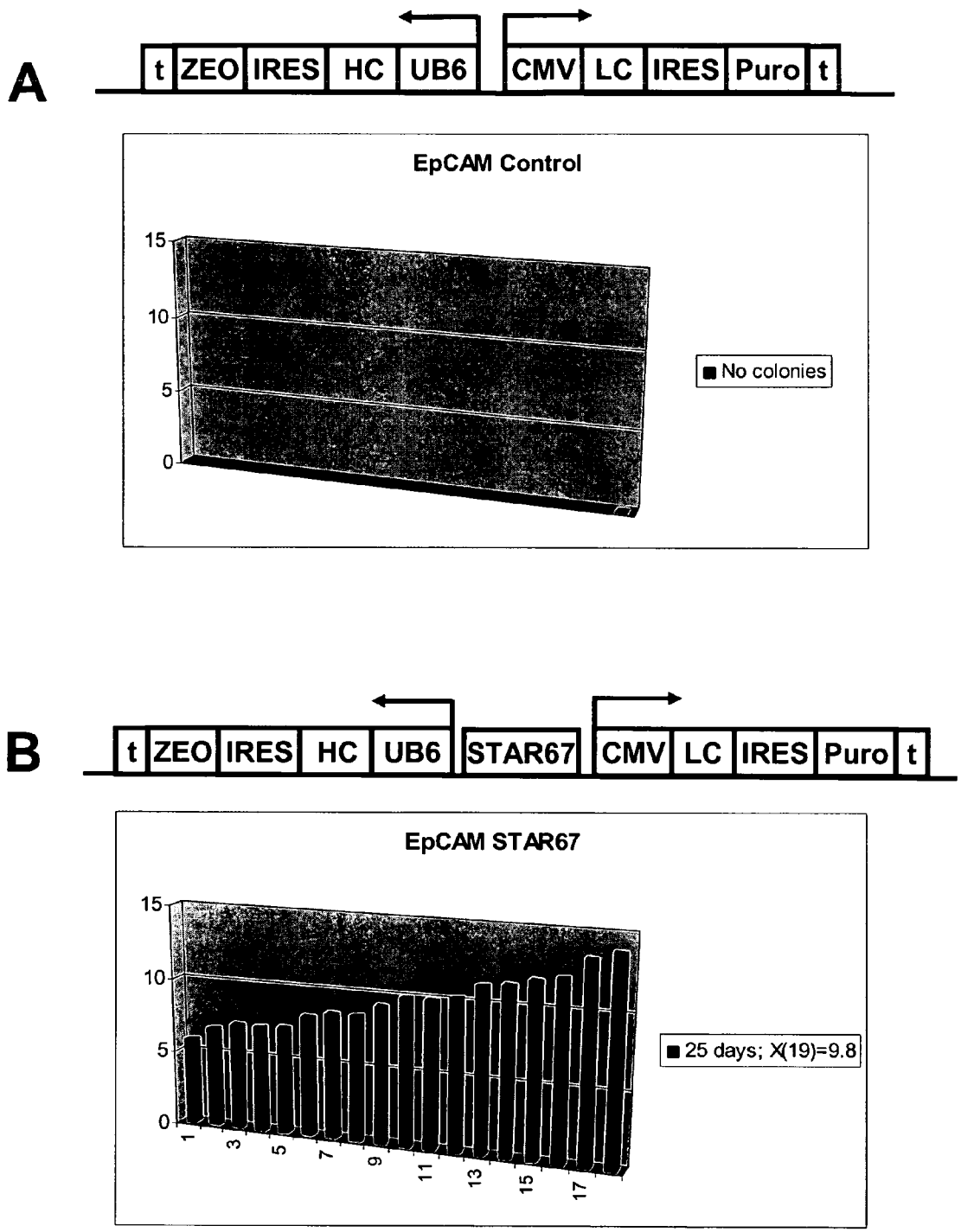

FIG. 11. STAR67 enhances UB6 and CMV-driven antibody expression levels in stably transfected CHO cells. See example 7 for details. A) single DNA molecule containing anti-EpCAM heavy chain (HC) and light chain (LC), each behind a promoter, and each linked to a different selectable marker gene (simultaneous selection was used for both markers): construct without STAR elements. No colonies were found; B) same construct with STAR67 between the two promoters. The anti-EpCAM antibody concentration is presented as pg/cell/day. X(19): average production level of the 19 colonies.

REFERENCES

Boshart, M, Weber, F, Jahn, G, Dorsch-Hasler, K, Fleckenstein, B, and Schaffner, W. (1985) A very strong enhancer is located upstream of an immediate early gene of human cytomegalovirus Cell 41, 521-530.

Chung J H, Whiteley M, and Felsenfeld G. (1993) A 5' element of the chicken beta-globin domain serves as an insulator in human erythroid cells and protects against position effect in Drosophila. *Cell* 74: 505-514.

Chung J H, Bell A C, Felsenfeld G. (1997). Characterization of the chicken beta-globin insulator. *Proc Natl Acad Sci USA* 94: 575-580.

Das, G C, Niyogi, S K, and Salzman, N P. (1985) SV40 promoters and their regulation *Prog Nucleic Acid Res Mol Biol* 32, 217-236.

Gill D R, Smyth S E, Goddard C A, Pringle I A, Higgins C F, Colledge W H, and Hyde S C. (2001) Increased persistence of lung gene expression using plasmids containing the ubiquitin C or elongation factor 1α promoter. Gene Therapy 8: 1539-1546.

Gossen M, and Bujard H. (1992) Tight control of gene expression in mammalian cells by tetracycline-responsive promoters. *Proc Natl Acad Sci USA* 89: 5547-5551.

Graham F O, Smiley J, Russell W and Nairn R. (1977). Characteristics of a human cell line transformed by DNA from human adenovirus type 5. J. Gen. Virol. 36, 59-72.

Huls G A, Heijnen I A F M, Cuomo M E, Koningsberger J C, Wiegman L, Boel E, van der Vuurst-de Vries A -R, Loyson S A J, Helfrich W, van Berge Henegouwen G P, van Meijer M, de Kruif J, Logtenberg T. (1999). A recombinant, fully human monoclonal antibody with antitumor activity constructed from phage-displayed antibody fragments. Nat Biotechnol. 17, 276-281.

Jones D, Kroos N, Anema R, Van Montfort B, Vooys A, Van Der Kraats S, Van Der Helm E, Smits S, Schouten J, Brouwer K, Lagerwerf F, Van Berkel P, Opstelten D -J, Logtenberg T, Bout A (2003) High-level expression of recombinant IgG in the human cell line PER.C6. Biotechnol. Prog. 19: 163-168.

Kaufman, R J. (2000) Overview of vector design for mammalian gene expression *Mol Biotechnol* 16, 151-160.

Kaufman, R J, and Sharp, P A. (1982) Construction of a modular dihydrofolate reductase cDNA gene: analysis of signals utilized for efficient expression *Mol Cell Biol* 2, 1304-1319.

Kellum R, and Schedl P. (1991) A position-effect assay for boundaries of higher order chromosomal domains. *Cell* 64: 941-950.

Kwaks T H, Barnett P, Hemrika W, Siersma T, Sewalt R G, Satijn D P, Brons J F, van Blokland R, Kwakman P, Kruckeberg A L, Kelder A, Otte A P. (2003) Identification of anti-repressor elements that confer high and stable protein production in mammalian cells. *Nat Biotechnol* 21, 553-558. Erratum in: Nat Biotechnol 21, 822 (2003).

Phi-Van L, Von Kreis J P, Ostertag W, and Stratling W H. (1990) The chicken lysozyme 5' matrix attachment region increases transcription from a heterologous promoter in heterologous cells and dampens position effects on the expression of transfected genes. Mol. Cell. Biol. 10: 2302-2307.

Lopez de Quinto, S, and Martinez-Salas, E. (1998) Parameters influencing translational efficiency in aphthovirus IRES-based bicistronic expression vectors *Gene* 217, 51-56.

Martin, D I, and Whitelaw, E. (1996) The vagaries of variegating transgenes *Bioessays* 18, 919-923.

Martinez-Salas, E. (1999) Internal ribosome entry site biology and its use in expression vectors *Curr Opin Biotechnol* 10, 458-464.

McBurney, M W, Mai, T, Yang, X, and Jardine, K. (2002) Evidence for repeat-induced gene silencing in cultured Mammalian cells: inactivation of tandem repeats of transfected genes *Exp Cell Res* 274, 1-8.

Migliaccio, A R, Bengra, C, Ling, J, Pi, W, Li, C, Zeng, S, Keskintepe, M, Whitney, B, Sanchez, M, Migliaccio, G, and Tuan, D. (2000) Stable and unstable transgene integration sites in the human genome: extinction of the Green Fluorescent Protein transgene in K562 cells *Gene* 256, 197-214.

Mizuguchi, H, Xu, Z, Ishii-Watabe, A, Uchida, E, and Hayakawa, T. (2000) IRES-dependent second gene expression is significantly lower than cap-dependent first gene expression in a bicistronic vector *Mol Ther* 1, 376-382.

Rees, S, Coote, J, Stables, J, Goodson, S, Harris, S, and Lee, M G. (1996) Bicistronic vector for the creation of stable mammalian cell lines that predisposes all antibiotic-resistant cells to express recombinant protein *Biotechniques* 20, 102-104, 106, 108-110.

Schorpp, M, Jager, R, Schellander, K, Schenkel, J, Wagner, E F, Weiher, H. and Angel, P. (1996) The human ubiquitin C promoter directs high ubiquitous expression of transgenes in mice *Nucleic Acids Res* 24, 1787-8.

Strutzenberger, K, Borth, N, Kunert, R, Steinfellner, W, and Katinger, H. (1999) Changes during subclone development and ageing of human antibody-producing recombinant CHO cells *J Biotechnol* 69, 215-26.

Van der Vlag, J, den Blaauwen, J L, Sewalt, R G, van Driel, R, and Otte, A P. (2000) Transcriptional repression mediated by polycomb group proteins and other chromatin-associated repressors is selectively blocked by insulators *J Biol Chem* 275, 697-704.

Whitelaw, E, Sutherland, H, Kearns, M, Morgan, H, Weaving, L, and Garrick, D. (2001) Epigenetic effects on transgene expression *Methods Mol Biol* 158, 351-68.

---

The invention claimed is:

1. A recombinant nucleic acid molecule comprising a first nucleic acid sequence selected from the group consisting of:
   a) SEQ ID NO:66; and
   b) functional fragments of SEQ ID NO:66 having the capability to at least in part block transcriptional silencing caused by heterochromatin adjacent to the recombinant nucleic acid molecule when the recombinant nucleic acid molecule is integrated into a cell's genome,
   wherein the recombinant nucleic acid molecule further comprises a second nucleic sequence comprising an expression cassette comprising a heterologous promoter operably linked to a nucleic acid sequence encoding a polypeptide of interest, and
   wherein said first nucleic acid sequence is situated upstream of said promoter in said expression cassette.

2. The recombinant nucleic acid molecule of claim 1, wherein said first nucleic acid sequence and said promoter are separated by less than 2 kb.

3. The recombinant nucleic acid molecule of claim 1, wherein said nucleic acid sequence encoding a polypeptide of interest is present in a multicistronic gene encoding a first selectable marker gene.

4. A recombinant nucleic acid molecule comprising an expression cassette comprising in the following order from 5' to 3':
   (I) a first nucleic acid sequence;
   (II) a promoter;
   (III) a nucleic acid sequence encoding a polypeptide of interest, wherein the promoter is operably linked to the nucleic acid encoding a polypeptide of interest; and
   (IV) a second nucleic acid sequence,
   wherein the first and second nucleic acid sequences are chosen from the group consisting of:

(i) SEQ ID NO:7; and
(ii) functional fragments of SEQ ID NO:7, wherein said fragments have the capability to at least in part block transcriptional silencing caused by heterochromatin adjacent to the recombinant nucleic acid molecule when the recombinant nucleic acid molecule is integrated into a cell's genome, wherein the expression cassette further comprises a third nucleic acid sequence chosen from the group consisting of:
a) SEQ ID NO:66; and
b) functional fragments of SEQ ID NO:66 having the capability to at least in part block transcriptional silencing caused by heterochromatin adjacent to the recombinant nucleic acid molecule when the recombinant nucleic acid molecule is integrated into a cell's genome, wherein said third nucleic acid sequence is situated upstream of said promoter and downstream of the first nucleic acid sequence.

5. An isolated cell comprising the recombinant nucleic acid molecule of claim 1.

6. The cell of claim 5, which is a mammalian cell.

7. The cell of claim 6, which is a CHO cell.

8. A method of producing a polypeptide of interest, said method comprising culturing a cell comprising the recombinant nucleic acid molecule of claim 1 in its genome, wherein said cell produces the polypeptide of interest.

9. The method according to claim 8, further comprising isolating said protein of interest.

10. A method according to claim 8, wherein said first nucleic acid sequence and said promoter are separated by less than 2 kb.

11. The method according to claim 8, wherein said nucleic acid encoding a protein of interest is present in a multicistronic gene further encoding a selectable marker gene.

12. The method according to claim 8, wherein said cell is a mammalian cell.

13. The method according to claim 12, wherein said cell is a CHO cell.

14. A method of increasing expression of a nucleic acid encoding a polypeptide of interest in a cell, said method comprising introducing into the genome of said cell the recombinant nucleic acid molecule of claim 1, thereby increasing expression of a nucleic acid encoding a polypeptide of interest.

15. A method of generating a host cell expressing two polypeptides of interest, the method comprising:
   a) introducing into the genome of a cell a first recombinant nucleic acid molecule, wherein said first nucleic acid molecule is the recombinant nucleic acid molecule of claim 3;
   b) introducing into the cell a second recombinant nucleic acid molecule comprising a heterologous promoter operably linked to a nucleic acid sequence encoding a second polypeptide of interest, wherein the nucleic acid sequence encoding a second polypeptide of interest is present in a multicistronic gene further encoding a second selectable marker gene; and
   c) selecting a cell expressing both selectable markers encoded by the first and second recombinant nucleic acid molecules,
   thereby generating a host cell expressing the two polypeptides of interest encoded by the first and second recombinant nucleic acid molecules.

16. A method of expressing two polypeptides of interest, the method comprising: culturing a host cell obtained by the method of claim 15, thereby expressing two polypeptides of interest.

17. The method of according to claim 15, wherein said two polypeptides of interest are part of a multimeric protein.

18. A recombinant nucleic acid molecule comprising an expression cassette comprising in the following order from 5' to 3': a first nucleic acid sequence comprising SEQ ID NO:7, a second nucleic sequence comprising SEQ ID NO:66, a promoter operably linked to a nucleic acid sequence encoding a peptide, and a third nucleic acid sequence encoding SEQ ID NO:7.

19. An expression vector comprising SEQ ID NO:66 upstream of a promoter operably linked a transgene to be expressed.

* * * * *

UNITED STATES PATENT AND TRADEMARK OFFICE
CERTIFICATE OF CORRECTION

Page 1 of 4

PATENT NO.         : 7,825,232 B2
APPLICATION NO.    : 11/632012
DATED              : November 2, 2010
INVENTOR(S)        : Arie Pieter Otte et al.

It is certified that error appears in the above-identified patent and that said Letters Patent is hereby corrected as shown below:

In the specification:

| | |
|---|---|
| COLUMN 2, LINE 19, | change "5'—anti-repressor sequence" to --5'-anti-repressor sequence-- |
| COLUMN 2, LINE 20, | change "A—promoter—nucleic acid" to --A-promoter-nucleic acid-- |
| COLUMN 2, LINE 21, | change "of interest—anti-repressor sequence B—3'" to --of interest-anti-repressor sequence B-3'-- |
| COLUMN 2, LINE 44, | change "said nucleic acid" to --said recombinant nucleic acid molecule-- |
| COLUMN 2, LINE 67, | change "said fragment has" to --said fragments have-- |
| COLUMN 3, LINE 29, | change "said fragment has" to --said fragments have-- |
| COLUMN 8, LINE 30, | change "such that expression cassette" to --such that the expression cassette-- |
| COLUMN 10, LINE 28, | change "sequence A—promoter—nucleic acid" to --sequence A-promoter-nucleic acid-- |
| COLUMN 10, LINE 29, | change "interest—anti-repressor" to --interest-anti-repressor-- |
| COLUMN 11, LINES 21-22 | change "in cell culture" to --in a cell culture-- |
| COLUMN 16, LINE 1, | change "Hams B D," to --Hames B D,-- |
| COLUMN 21, LINE 40, | change "5'—STAR sequence" to --5'-STAR sequence-- |
| COLUMN 21, LINE 41, | change "A—STAR sequence C—promoter—nucleic acid" to --A-STAR sequence C-promoter-nucleic acid-- |
| COLUMN 21, LINE 42, | change "protein of interest—STAR sequence B—3'" to --protein of interest-STAR sequence B-3'-- |
| COLUMN 25, LINE 36, | change "EF1αdriven" to --EF1α driven-- |

Signed and Sealed this
Fifth Day of April, 2011

David J. Kappos
*Director of the United States Patent and Trademark Office*

CERTIFICATE OF CORRECTION (continued)
U.S. Pat. No. 7,825,232 B2

In the claims (changes marked in underline and strikeout mode):

CLAIM 1, COLUMN 127, LINES 51-67
--1. A recombinant nucleic acid molecule comprising a first nucleic acid sequence selected from the group consisting of:
   a) SEQ ID NO:66; and
   b) functional fragments of SEQ ID NO:66 having the capability to at least in part block transcriptional silencing caused by heterochromatin adjacent to the recombinant nucleic acid molecule when the recombinant nucleic acid molecule is integrated into a cell's genome,
   wherein the recombinant nucleic acid molecule further comprises a second nucleic <u>acid</u> sequence comprising an expression cassette comprising a heterologous promoter operably linked to a nucleic acid sequence encoding a polypeptide of interest, and
   wherein said first nucleic acid sequence is situated upstream of said promoter in said expression cassette.--

CLAIM 4, COLUMN 128, LINE 57 through COLUMN 129, LINE 19,
--4. A recombinant nucleic acid molecule comprising an expression cassette comprising in the following order from 5' to 3':
   (I) a first nucleic acid sequence;
   (II) a promoter;
   (III) a nucleic acid sequence encoding a polypeptide of interest, wherein the promoter is operably linked to the nucleic acid <u>sequence</u> encoding a polypeptide of interest; and
   (IV) a second nucleic acid sequence,
   wherein the first and second nucleic acid sequences are chosen from the group consisting of:
      (i) SEQ ID NO:7; and
      (ii) functional fragments of SEQ ID NO:7, wherein said fragments have the capability to at least in part block transcriptional silencing caused by heterochromatin adjacent to the recombinant nucleic acid molecule when the recombinant nucleic acid molecule is integrated into a cell's genome,
   wherein the expression cassette further comprises a third nucleic acid sequence chosen from the group consisting of:
      (a) SEQ ID NO:66; and
      (b) functional fragments of SEQ ID NO:66 having the capability to at least in part block transcriptional silencing caused by heterochromatin adjacent to the recombinant nucleic acid molecule when the recombinant nucleic acid molecule is integrated into a cell's genome,
   wherein said third nucleic acid sequence is situated upstream of said promoter and downstream of the first nucleic acid sequence.--

CERTIFICATE OF CORRECTION (continued)
U.S. Pat. No. 7,825,232 B2

In the claims (changes marked in underline and strikeout mode) (continued):

CLAIM 9, COLUMN 129, LINES 28-29
--9. The method according to claim 8, further comprising isolating said ~~protein~~ <u>polypeptide</u> of interest.--

CLAIM 10, COLUMN 129, LINES 30-32
--10. [[A]] <u>The</u> method according to claim 8, wherein said first nucleic acid sequence and said promoter are separated by less than 2 kb.--

CLAIM 11, COLUMN 129, LINES 33-35
--11. The method according to claim 8, wherein said nucleic acid <u>sequence</u> encoding a ~~protein~~ <u>polypeptide</u> of interest is present in a multicistronic gene further encoding a selectable marker gene.

CLAIM 15, COLUMN 130, LINES 5-23,
--15. A method of generating a host cell expressing two polypeptides of interest, the method comprising:
    a) introducing into the genome of a cell a first recombinant nucleic acid molecule, wherein said first <u>recombinant</u> nucleic acid molecule is the recombinant nucleic acid molecule of claim 3;
    b) introducing into the cell a second recombinant nucleic acid molecule comprising a heterologous promoter operably linked to a nucleic acid sequence encoding a second polypeptide of interest, wherein the nucleic acid sequence encoding a second polypeptide of interest is present in a multicistronic gene further encoding a second selectable marker gene; and
    c) selecting a cell expressing both selectable markers encoded by the first and second recombinant nucleic acid molecules,
thereby generating a host cell expressing two polypeptides of interest encoded by the first and second recombinant nucleic acid molecules.--

CLAIM 17, COLUMN 130, LINES 28, 29
--17. The method [[of]] according to claim 15, wherein said two polypeptides of interest are part of a multimeric protein.--

CLAIM 18, COLUMN 130, LINES 30-36
--18. A recombinant nucleic acid molecule comprising an expression cassette comprising in the following order from 5' to 3': a first nucleic acid sequence comprising SEQ ID NO:7, a second nucleic <u>acid</u> sequence comprising SEQ ID NO:66, a promoter operably linked to a nucleic acid sequence encoding a peptide, and a third nucleic acid sequence encoding SEQ ID NO:7.--

CERTIFICATE OF CORRECTION (continued)
U.S. Pat. No. 7,825,232 B2

In the claims (changes marked in underline and strikeout mode) (continued):

CLAIM 19, COLUMN 130, LINES 37-39
 --19. An expression vector comprising SEQ ID NO:66 upstream of a promoter operably linked <u>to</u> a transgene to be expressed.--

SEQUENCE LISTING

```
<160> NUMBER OF SEQ ID NOS: 82

<210> SEQ ID NO 1
<211> LENGTH: 749
<212> TYPE: DNA
<213> ORGANISM: Homo sapiens
<220> FEATURE:
<221> NAME/KEY: misc_feature
<223> OTHER INFORMATION: sequence of STAR1

<400> SEQUENCE: 1
atgcggtggg ggcgcgccag agactcgtgg gatccttggc ttggatgttt ggatctttct      60
gagttgcctg tgccgcgaaa gacaggtaca tttctgatta ggcctgtgaa gcctcctgga     120
ggaccatctc attaagacga tggtattgga gggagagtca cagaaagaac tgtggcccct     180
ccctcactgc aaaacggaag tgattttatt ttaatgggag ttggaatatg tgagggctgc     240
aggaaccagt ctccctcctt cttggttgga aaagctgggg ctggcctcag agacaggttt     300
tttggccccg ctgggctggg cagtctagtc gacccttttgt agactgtgca caccctaga    360 agagcaacta cccctataca ccaggctggc tcaagtgaaa ggggctctgg gctccagtct     420
ggaaaatctg gtgtcctggg gacctctggt cttgcttctc tcctcccctg cactggctct     480
gggtgcttat ctctgcagaa gcttctcgct agcaaaccca cattcagcgc cctgtagctg     540
aacacagcac aaaaagccct agagatcaaa agcattagta tgggcagttg agcgggaggt     600
gaatatttaa cgcttttgtt catcaataac tcgttggctt tgacctgtct gaacaagtcg     660
agcaataagg tgaaatgcag gtcacagcgt ctaacaaata tgaaaatgtg tatattcacc     720
ccggtctcca gccggcgcgc caggctccc                                       749

<210> SEQ ID NO 2
<211> LENGTH: 883
<212> TYPE: DNA
<213> ORGANISM: Homo sapiens
```

```
<220> FEATURE:
<221> NAME/KEY: misc_feature
<223> OTHER INFORMATION: sequence of STAR2

<400> SEQUENCE: 2
gggtgcttcc tgaattcttc cctgagaagg atggtggccg gtaaggtccg tgtaggtggg      60
gtgcggctcc ccaggccccg gcccgtggtg gtggccgctg cccagcggcc cggcaccccc     120
atagtccatg gcgcccgagg cagcgtgggg gaggtgagtt agaccaaaga gggctggccc     180
ggagttgctc atgggctcca catagctgcc ccccacgaag acggggcttc cctgtatgtg     240
tggggtccca tagctgccgt tgccctgcag gccatgagcg tgcgggtcat agtcgggggt     300 gcccctgcg cccgcccctg ccgccgtgta gcgcttctgt gggggtggcg ggggtgcgca      360
gctgggcagg gacgcagggt aggaggcggg ggcagcccg taggtaccct ggggggggctt     420 ggagaagggc gggggcgact ggggctcata cgggacgctg ttgaccagcg aatgcataga     480
gttcagatag ccaccggctc cggggggcac ggggctgcga cttggagact ggcccccga      540 tgacgttagc atgcccttgc ccttctgatc cttttttgtac ttcatgcggc gattctggaa    600
ccagatcttg atctggcgct cagtgaggtt cagcagattg gccatctcca cccggcgcgg     660
ccggcacagg tagcggttga agtggaactc tttctccagc tccaccagct gcgcgctcgt     720
gtaggccgtg cgcgcgcgct tggacgaagc ctgccccggc gggctcttgt cgccagcgca     780
gctttcgcct gcgaggacag agagaggaag agcggcgtca ggggctgccg cggccccgcc     840
cagcccctga cccagcccgg ccctccttc caccaggccc caa                        883

<210> SEQ ID NO 3
<211> LENGTH: 2126
<212> TYPE: DNA
<213> ORGANISM: Homo sapiens
<220> FEATURE:
<221> NAME/KEY: misc_feature
<223> OTHER INFORMATION: sequence of STAR3

<400> SEQUENCE: 3
atctcgagta ctgaaatagg agtaaatctg aagagcaaat aagatgagcc agaaaaccat      60
gaaaagaaca gggactacca gttgattcca caaggacatt cccaaggtga aaggccata     120 tacctccact acctgaacca attctctgta tgcagattta gcaaggttat aaggtagcaa     180
aagattagac ccaagaaaat agagaacttc caatccagta aaaatcatag caaatttatt    240
gatgataaca attgtctcca aaggaacaag gcagagtcgt gctagcagag gaagcacgtg    300
agctgaaaac agccaaatct gctttgtttt catgacacag gagcataaag tacacaccac    360
caactgacct attaaggctg tggtaaaccg attcatagag agaggttcta aatacattgg    420
tccctcacag gcaaactgca gttcgctccg aacgtagtcc ctggaaattt gatgtccagt    480
atagaaaagc agagcagtca aaaaatatag ataaagctga accagatgtt gcctgggcaa    540
tgttagcagc accacactta agatataacc tcaggctgtg gactccctcc ctggggagcg    600
gtgctgccgg cggcgggcgg gctccgcaac tccccggctc tctcgcccgc cctccgttc     660 tcctcgggcg gcgcggggg ccgggactgc gccgctcaca gcggcggctc ttctgcgccc    720
ggcctcggag gcagtggcgg tggcggccat ggcctcctgc gttcgccgat gtcagcattt    780
cgaactgagg gtcatctcct tgggactggt tagacagtgg gtgcagccca cggagggcga    840
gttgaagcag ggtgggggtgt cacctccccc aggaagtcca gtgggtcagg gaactccctc    900
ccctagccaa gggaggccgt gagggactgt gcccggtgag agactgtgcc ctgaggaaag    960
```

```
gtgcactctg gcccagatac tacactttc ccacggtctt caaaacccgc agaccaggag     1020
attccctcgg gttcctacac caccaggacc ctgggtttca accacaaaac cgggccattt     1080
gggcagacac ccagctagct gcaagagttg tttttttttt tatactcctg tggcacctgg     1140
aacgccagcg agagagcacc tttcactccc ctggaaaggg ggctgaaggc agggaccttt     1200
agctgcgggc tagggggttt ggggttgagt gggggagggg agaggaaaaa ggcctcgtca     1260
ttggcgtcgt ctgcagccaa taaggctacg ctcctctgct gcgagtagac ccaatccttt     1320
cctagaggtg gaggggcgg gtaggtggaa gtagaggtgg cgcggtatct aggagagaga     1380
aaaagggctg gaccaatagg tgcccggaag aggcggaccc agcggtctgt tgattggtat     1440
tggcagtgga ccctcccccg gggtggtgcc ggaggggggg atgatgggtc gagggggtgtg     1500 tttatgtgga agcgagatga ccggcaggaa cctgccccaa tgggctgcag agtggttagt     1560
gagtgggtga cagacagacc cgtaggccaa cgggtggcct taagtgtctt tggtctcctc     1620
caatggagca gcggcgggc gggaccgcga ctcgggttta atgagactcc attgggctgt     1680
aatcagtgtc atgtcggatt catgtcaacg acaacaacag ggggacacaa aatggcggcg     1740
gcttagtcct acccctggcg gcggcggcag cggtggcgga ggcgacggca ctcctccagg     1800
cggcagccgc agtttctcag gcagcggcag cgccccggc aggcgcggtg gcggtggcgc     1860
gcagccaggt ctgtcaccca ccccgcgcgt tcccaggggg aggagactgg gcgggagggg     1920
ggaacagacg ggggggatt caggggcttg cgacgcccct cccacaggcc tctgcgcgag     1980
ggtcaccgcg gggccgctcg gggtcaggct gcccctgagc gtgacggtag ggggcggggg     2040 aaagggagg agggacaggc cccgcccctc ggcagggcct ctagggcaag ggggcggggc     2100
tcgaggagcg gaggggggcg gggcgg                                           2126

<210> SEQ ID NO 4
<211> LENGTH: 1625
<212> TYPE: DNA
<213> ORGANISM: Homo sapiens
<220> FEATURE:
<221> NAME/KEY: misc_feature
<223> OTHER INFORMATION: sequence of STAR4

<400> SEQUENCE: 4
gatctgagtc atgttttaag gggaggattc ttttggctgc tgagttgaga ttaggttgag       60
ggtagtgaag gtaaaggcag tgagaccacg taggggtcat tgcagtaatc caggctggag      120
atgatggtgg ttcagttgga atagcagtgc atgtgctgta acaacctcag ctgggaagca      180
gtatatgtgg cgttatgacc tcagctggaa cagcaatgca tgtggtggtg taatgacccc      240
agctgggtag ggtgcatgtg gtgtaacgac ctcagctggg tagcagtgtg tgtgatgtaa      300
caacctcagc tgggtagcag tgtacttgat aaaatgttgg catactctag atttgttatg      360
agggtagtgc cattaaattt ctccacaaat tggttgtcac gtatgagtga aaagaggaag      420
tgatggaaga cttcagtgct tttggcctga ataaatagaa gacgtcattt ccagttaatg      480
gagacaggga agactaaagg tagggtggga ttcagtagag caggtgttca gttttgaata      540
tgatgaactc tgagagagga aaaacttttt ctacctctta gttttgtga ctggacttaa       600 gaattaaagt gacataagac agagtaacaa gacaaaaata tgcgaggtta tttaatattt      660
ttacttgcag aggggaatct tcaaaagaaa aatgaagacc caagaagcc attagggtca       720 aaagctcata tgccttttta agtagaaaat gataaatttt aacaatgtga gaagacaaag      780
gtgtttgagc tgagggcaat aaattgtggg acagtgatta gaaatatat gggggaaatg       840
```

-continued

```
aaatgataag ttattttagt agatttattc ttcatatcta ttttggcttc aacttccagt    900
ctctagtgat aagaatgttc ttctcttcct ggtacagaga gagcacctt tctcatgggaa    960
attttatgac cttgctgtaa gtagaaaggg gaagatcgat ctcctgtttc ccagcatcag   1020
gatgcaaaca tttccctcca ttccagttct caaccccatg ctgggcctc atggcattcc   1080
agcatcgcta tgagtgcacc tttcctgcag gctgcctcgg gtagctggtg cactgctagg   1140
tcagtctatg tgaccaggag ctgggcctct ggcaatgcc agttggcagc ccccatccct   1200
ccactgctgg gggcctccta tccagaaggg cttggtgtgc agaacgatgg tgcaccatca   1260
tcattcccca cttgccatct ttcaggggac agccagctgc tttgggcgcg gcaaaaaaca   1320
cccaactcac tcctcttcag gggcctctgg tctgatgcca ccacaggaca tccttgagtg   1380
ctgggcagtc tgaggacagg gaaggagtga tgaccacaaa acaggaatgg cagcagcagt   1440
gacaggagga agtcaaaggc ttgtgtgtcc tggccctgct gagggctggc gagggccctg   1500
ggatggcgct cagtgcctgg tcggctgcaa gaggccagcc ctctgcccat gaggggagct   1560
ggcagtgacc aagctgcact gccctggtgg tgcatttcct gccccactct ttccttctaa   1620
gatcc                                                               1625
```

<210> SEQ ID NO 5
<211> LENGTH: 1571
<212> TYPE: DNA
<213> ORGANISM: Homo sapiens
<220> FEATURE:
<221> NAME/KEY: misc_feature
<223> OTHER INFORMATION: sequence of STAR5

<400> SEQUENCE: 5

```
cacctgattt aaatgatctg tctggtgagc tcactgggtc tttactcgca tgctgggtcc     60
acagctccac tgtcctgcag ggtccgtgag tgtgggcccc ttatctattt catcatcata    120
accctgcgtg tcctcaactc ctggcacata ttgggtggcc ccatccacac acggttgttg    180
agtgaatcca tgagatgaca aaggctatga tgtagactat atcatgagcc agaaccaggc    240
tttcctacct ccagacaatc aagggccttg atttgggatt gagggagaaa ggagtagaag    300
ccaggaagga gaagagattg aggtttacca agggtgcaaa gtcctggccc ctgactgtag    360
gctgaaaact atagaaatga tagaacaatt ttgcaatgaa atgcagaaga ccctgcatca    420
actttaggtg ggacttcggg tatttttatg gccacagaac atcctcccat ttacctgcat    480
ggcccagaca cagacttcaa aacagttgag gccagcaggc tccaggtaag tggtaggatt    540
ccagaatgcc ctcagagtgt tgtgggaggc agcaggcgat tttcctggac ttctgagttt    600
atgagaaccc caaccccaa ttggcattaa cattgaggtc tcaatgtatc atggcaggaa    660
gcttccgagt ggtgaaaagg aaagtgaaca tcaaagctcg gaagacaaga gggtggagtg    720
atggcaacca agagcaagac ccttccctct cctgtgatgg ggtggctcta tgtgaagccc    780
ccaaactgga cacaggtctg gcagaatgag gaacccactg agatttagcg ccaacatcca    840
gcataaaagg gagactgaca tagaatttga gttagttaaa aataaggcac aatgcttttc    900
atgtattcct gagttttgtg gactggtgtt caatttgcag cattcttagt tgattaaatc    960
tgagatgaag aaagagtgtc caacactttc accttggaaa gctctggaaa agcaaaaggg   1020
agagacaatt agcttcatcc attaactcac ttagtcatta tgcattcatt catgtaacta   1080
ccaaacacgt actgagtgcc taacactcct gagacactga gaagtttctt gggaatacaa   1140
agatgaataa aaaccacgcc aggcaggagt tggaggaagg ttctggatgc caccacgctc   1200
```

```
tacctcctgg ctggacacca ggcaatgttg gtaaccttct gcctccaatt tctgcaaata    1260
cataattaat aaacacaagg ttatcttcta aacagttctt aaaatgagtc aactttgttt    1320
aaacttgttc ttttagaga aaaatgtatt tttgaaagag ttggttagtg ctaggggaaa    1380
tgtctgggca cagctcagtc tggtgtgaga gcaggaagca gctctgtgtg tctggggtgg    1440
gtacgtatgt aggacctgtg ggagaccagg ttggggaag gccctcctc atcaagggct     1500 cctttgcttt ggtttgcttt ggcgtgggag gtgctgtgcc acaagggaat acgggaaata    1560
agatctctgc t                                                         1571

<210> SEQ ID NO 6
<211> LENGTH: 1173
<212> TYPE: DNA
<213> ORGANISM: Homo sapiens
<220> FEATURE:
<221> NAME/KEY: misc_feature
<223> OTHER INFORMATION: sequence of STAR6

<400> SEQUENCE: 6
tgacccacca cagacatccc ctctggcctc ctgagtggtt tcttcagcac agcttccaga     60
gccaaattaa acgttcactc tatgtctata gacaaaaagg gttttgacta aactctgtgt    120
tttagagagg gagttaaatg ctgttaactt tttaggggtg ggcgagaggg atgacaaata    180
acaacttgtc tgaatgtttt acatttctcc ccactgcctc aagaaggttc acaacgaggt    240
catccatgat aaggagtaag acctcccagc cggactgtcc ctcggcccc agaggacact     300 ccacagagat atgctaactg gacttggaga ctggctcaca ctccagagaa aagcatggag    360
cacgagcgca cagagcaggg ccaaggtccc aggacagaa tgtctaggag ggagattggg     420
gtgagggtaa tctgatgcaa ttactgtggc agctcaacat tcaagggagg gggaagaaag    480
aaacagtccc tgtcaagtaa gttgtgcagc agagatggta agctccaaaa tttgaaactt    540
tggctgctgg aaagttttag ggggcagaga taagaagaca taagagactt tgagggttta    600
ctacacacta gacgctctat gcatttattt attttattatc tcttatttat tactttgtat    660
aactcttata ataatcttat gaaaacggaa accctcatat acccatttta cagatgagaa    720
aagtgacaat tttgagagca tagctaagaa tagctagtaa gtaaaggagc tgggacctaa    780
accaaaccct atctcaccag agtacacact cttttttttt ttccagtgta attttttta     840 atttttattt tactttaagt tctgggatac atgtgcagaa ggtatggttt gttacatagg    900
tatatgtgtg ccatagtgga ttgctgcacc tatcaacccg tcatctaggt ttaagcccca    960
catgcattag ctatttgtcc tgatgctctc cctcccctcc ccacaccaga caggccttgg   1020
tgtgtgatgt tcccctccct gtgtccatgt gttctcactg ttcagctccc acttatgagt   1080
gagaacgtgt ggtatttggt tttctgttcc tgtgttagtt tgctgaggat gatggcttcc   1140
agcttcatcc atgtccctgc aaaggacacg atc                                1173

<210> SEQ ID NO 7
<211> LENGTH: 2101
<212> TYPE: DNA
<213> ORGANISM: Homo sapiens
<220> FEATURE:
<221> NAME/KEY: misc_feature
<223> OTHER INFORMATION: sequence of STAR7

<400> SEQUENCE: 7
aggtgggtgg atcacccgag gtcaggagtt caagaccagc ctggccaaca tggtaaaacc     60
tcgtctctac taaaaaatac gaaaaattag ctggttgtgg tggtgcgtgc ttgtaatccc    120
```

-continued

| | |
|---|---|
| agctactcgg gaggctgagg caggagaatc acttgaatct gggaggcaga ggttgcagtg | 180 |
| agctgagata gtgccattgc actccagcct gggcaacaga cggagactct gtctccaaaa | 240 |
| aaaaaaaaaa aaatcttaga ggacaagaat ggctctctca aacttttgaa gaaagaataa | 300 |
| ataaattatg cagttctaga agaagtaatg gggatatagg tgcagctcat gatgaggaag | 360 |
| acttagctta actttcataa tgcatctgtc tggcctaaga cgtggtgagc tttttatgtc | 420 |
| tgaaaacatt ccaatataga atgataataa taatcacttc tgaccccct tttttttcct | 480 |
| ctccctagac tgtgaagcag aaaccccata ttttcttag ggaagtggct acgcactttg | 540 |
| tatttatatt aacaactacc ttatcaggaa attcatattg ttgcccttt atggatgggg | 600 |
| aaactggaca gtgacagag caaaatccaa acacagctgg ggatttccct cttttagatg | 660 |
| atgattttaa aagaatgctg ccagagagat tcttgcagtg ttggaggaca tatatgacct | 720 |
| ttaagatatt ttccagctca gagatgctat gaatgtatcc tgagtgcatg gatggacctc | 780 |
| agttttgcag attctgtagc ttatacaatt tggtggtttt ctttagaaga aaataacaca | 840 |
| tttataaata ttaaaatagg cccaagacct tacaagggca ttcatacaaa tgagaggctc | 900 |
| tgaagtttga gttgttcac tttctagtta attatctcct gcctgtttgt cataaatgcg | 960 |
| tttagtaggg agctgctaat gacaggttcc tccaacagag tgtggaagaa ggagatgaca | 1020 |
| gctggcttcc cctctgggac agcctcagag ctagtgggga aactatgtta gcagagtgat | 1080 |
| gcagtgacca agaaaatagc actaggagaa agctggtcca tgagcagctg gtgagaaaag | 1140 |
| gggtggtaat catgtatgcc ctttcctgtt ttatttttta ttgggtttcc ttttgcctct | 1200 |
| caattccttc tgacaataca aaatgttggt tggaacatgg agcacctgga agtctggttc | 1260 |
| attttctctc agtctcttga tgttctctcg ggttcactgc ctattgttct cagttctaca | 1320 |
| cttgagcaat ctcctcaata gctaaagctt ccacaatgca gattttgtga tgacaaattc | 1380 |
| agcatcaccc agcagaactt aggttttttt ctgtcctccg tttcctgacc ttttcttct | 1440 |
| gagtgcttta tgtcacctcg tgaaccatcc tttccttagt catctaccta gcagtcctga | 1500 |
| ttcttttgac ttgtctccct acaccacaat aaatcactaa ttactatgga ttcaatccct | 1560 |
| aaaatttgca caaacttgca aatagattac gggttgaaac ttagagattt caaacttgag | 1620 |
| aaaaaagttt aaatcaagaa aaatgacctt taccttgaga gtagaggcaa tgtcatttcc | 1680 |
| aggaataatt ataataatat tgtgtttaat atttgtatgt aacatttgaa taccttcaat | 1740 |
| gttcttattt gtgttatttt aatctcttga tgttactaac tcatttggta gggaagaaaa | 1800 |
| catgctaaaa taggcatgag tgtcttatta aatgtgacaa gtgaatagat ggcagaaggt | 1860 |
| ggattcatat tcagttttcc atcaccctgg aaatcatgcg gagatgattt ctgcttgcaa | 1920 |
| ataaaactaa cccaatgagg ggaacagctg ttcttaggtg aaaacaaaac aaacacgcca | 1980 |
| aaaccttta ttctctttat tatgaatcaa atttttcctc tcagataatt gttttattta | 2040 |
| tttatttta ttattattgt tattatgtcc agtctcactc tgtcgcctaa gctggcatga | 2100 |
| t | 2101 |

<210> SEQ ID NO 8
<211> LENGTH: 1821
<212> TYPE: DNA
<213> ORGANISM: Homo sapiens
<220> FEATURE:
<221> NAME/KEY: misc_feature
<223> OTHER INFORMATION: sequence of STAR8

<400> SEQUENCE: 8

```
gagatcacct cgaagagagt ctaacgtccg taggaacgct ctcgggttca caaggattga    60
ccgaacccca ggatacgtcg ctctccatct gaggcttgct ccaaatggcc ctccactatt   120
ccaggcacgt gggtgtctcc cctaactctc cctgctctcc tgagcccatg ctgcctatca   180
cccatcggtg caggtccttt ctgaagagct cgggtggatt ctctccatcc cacttccttt   240
cccaagaaag aagccaccgt tccaagacac ccaatgggac attccccttc cacctccttc   300
tccaaagttg cccaggtgtt catcacaggt tagggagaga agcccccagg tttcagttac   360
aaggcatagg acgctggcat gaacacacac acacacacac acacacacac acacacacac   420
acacgactcg aagaggtagc cacaagggtc attaaacact tgacgactgt tttccaaaaa   480
cgtggatgca gttcatccac gccaaagcca agggtgcaaa gcaaacacgg aatggtggag   540
agattccaga ggctcaccaa accctctcag gaatattttc ctgaccctgg gggcagaggt   600
tggaaacatt gaggacattt cttgggacac acggagaagc tgaccgacca ggcattttcc   660
tttccactgc aaatgaccta tggcggggggc atttcacttt ccctgcaaa tcacctatgg    720
cgaggtacct ccccaagccc ccaccccac ttccgcgaat cggcatggct cggcctctat   780
ccgggtgtca ctccaggtag gcttctcaac gctctcggct caaagaagga caatcacagg   840
tccaagccca aagcccacac ctcttccttt tgttataccc acagaagtta gagaaaacgc   900
cacactttga gacaaattaa gagtccttta tttaagccgg cggccaaaga gatggctaac   960
gctcaaaatt ctctgggccc cgaggaaggg gcttgactaa cttctatacc ttggtttagg  1020
aaggggaggg gaactcaaat gcggtaattc tacagaagta aaaacatgca ggaatcaaaa  1080
gaagcaaatg gttatagaga gataaacagt tttaaaaggc aaatggttac aaaaggcaac  1140
ggtaccaggt gcggggctct aaatccttca tgacacttag atataggtgc tatgctggac  1200
acgaactcaa ggctttatgt tgttatctct tcgagaaaaa tcctgggaac ttcatgcact  1260
gtttgtgcca gtatcttatc agttgattgg gctcccttga aatgctgagt atctgcttac  1320
acaggtcaac tccttgcgga aggggttgg gtaaggagcc cttcgtgtct cgtaaattaa   1380
ggggtcgatt ggagtttgtc cagcattccc agctacagag agcctatttt acatgagaag  1440
caaggctagg tgattaaaga gaccaacagg gaagattcaa agtagcgact tagagtaaaa  1500
acaaggttag gcatttcact ttcccagaga acgcgcaaac attcaatggg agagaggtcc  1560
cgagtcgtca aagtcccaga tgtggcgagc ccccgggagg aaaaaccgtg tcttccttag  1620
gatgcccgga acaagagcta ggcttccgga gctaggcagc catctatgtc cgtgagccgg  1680
cgggagggag accgccggga ggcgaagtgg ggcggggcca tccttctttc tgctctgctg  1740
ctgccgggga gctcctggct ggcgtccaag cggcaggagg ccgccgtcct gcagggcgcc  1800
gtagagtttg cggtgcagag t                                            1821
```

<210> SEQ ID NO 9
<211> LENGTH: 1929
<212> TYPE: DNA
<213> ORGANISM: Homo sapiens
<220> FEATURE:
<221> NAME/KEY: misc_feature
<223> OTHER INFORMATION: sequence of STAR9

<400> SEQUENCE: 9

```
cacttcctgg gagtggagca gaggctctgc gtggagcatc catgtgcagt actcttaggt    60
acggaaggga ttgggctaaa ccatggatgg gagctgggaa gggaagggac caacttcagg   120
```

-continued

```
cccactggg acactggagc tgccaccctt tagagccctc ctaaccctac accagaggct      180
gagggggacc tcagacatca cacacatgct ttcccatgtt ttcagaaatc tggaaacgta      240
gaacttcagg ggtgagagtg cctagatatt gaatacaagg ctagattggg cttctgtaat      300
atcccaaagg accctccagc tttttcacca gcacctaatg cccatcagat accaaagaca      360
cagcttagga gaggttcacc ctgaagctga ggaggaggca gccggattag agttgactga      420
gcaaggatga ctgccttctc cacctgacga tttcagctgc tgccctttc ttttcctggg      480 aatgcctgtc gccatggcct tctgtgtcca caggagagtt tgacccagat actcatggac      540
caggcaaagg tgctgttcct cccagcccag ggcccaccat gaagcatgcc tgggagcctg      600
gtaaggaccc agccactcct gggctgttga cattggcttc tcttgcccag cattgtagcc      660
acgccactgc attgtactgt gagataagtc aaggtgggct caccaggacc tgcactaaat      720
tgtgaaattc agctccaaag aactttggaa attacccatg catttaagca aaatgaatga      780
tacctgagca acccttca cattggcaca agttacaatc ctgtctcatc ctcttgatta      840
caaattccat ccaggcaaga gctgtatcac cctgaggtct ccccattcat gttttggtca      900
ataatattta gtttcctttt gaaaatagat ttttgtgtta ctccattatg atgggcagag      960
gccagatgct tatattctat ttaaatgact atgttttct atctgtaact gggtttgtgt     1020
tcaggtggta aatgctttt tttgcagtc agaagattcc tggaaggcga ccagaaatta     1080
gctggccgct gtcagacctg aagttacttc taaagggcct ttagaaatga attcttttt     1140 atgccttctc tgaattctga gaagtaggct tgacttcccc taagtgtgga gttgggagtc     1200
aactcttctg aaaagaaagt ttcagagcat tttccaaagc catggtcagc tgtgggaagg     1260
gaagacgatg gatagtacag ttgccggaaa acactgatgg aggcggatgc tccagctcag     1320
ccaaagacct ttgttctgcc cacccagaa atgcccttc ctcaatcgca gaaacgttgc     1380
cccatggctc ctgatactca gaatgcagcc tctgaccagg accatctgca tcctccagga     1440
gctcgtaaga aatgcagcat cgtgggacct gctggcacct ggtgaaccca aacctgcagg     1500
gctcctgggt gtgcttgggg cggctgcagg ggaagaggga gtcagcagcc tcctcctgac     1560
cttccccggg gctgctttc tgaggggcca gaatgcaccg gttgaccttg ttgcatcact     1620
ggcccatgac tggctgcttt ggtcaggtgt aaaaaggtgt ttccagaggg tctgctcctc     1680
tcactatcgg accaggtttc catggagagc tcagcctccc agcaaggata gagaacttca     1740
aatggctcaa agaactgaga ggccacacat gtgtgacctg aatagtctct gctgcaaaac     1800
aaagggtttc ttaatgtaaa acgttctctt cctcacagag gggttcccag ctgctagtgg     1860
gcatgttgca ggcatttcct gggctgcatc aggttgtcat aagccagagg atcatttttg     1920
ggggctcat                                                              1929
```

<210> SEQ ID NO 10
<211> LENGTH: 1167
<212> TYPE: DNA
<213> ORGANISM: Homo sapiens
<220> FEATURE:
<221> NAME/KEY: misc_feature
<223> OTHER INFORMATION: sequence of STAR10
<220> FEATURE:
<221> NAME/KEY: misc_feature
<222> LOCATION: (452)..(1143)
<223> OTHER INFORMATION: n is a, c, g, or t on various positions

```
<400> SEQUENCE: 10
aggtcaggag ttcaagacca gcctggccaa catggtgaaa ccctgtccct acaaaaaata      60
caaaaattag ccgggcgtgg tggggggcgc ctataatccc agctactcag gatgctgaga     120
caggagaatt gtttgaaccc gggaggtgga ggttgcagtg aactgagatc gcgccactgc    180
actccagcct ggtgacagag agagactccg tctcaacaac agacaaacaa acaaacaaac    240
aacaacaaaa atgtttactg acagctttat tgagataaaa ttcacatgcc ataaaggtca    300
ccttctacag tatacaattc agtggattta gtatgttcac aaagttgtac gttgttcacc    360
atctactcca gaacatttac atcaccccta aaagaagctc tttagcagtc acttctcatt    420
ctccccagcc cctgccaacc acgaatctac tntctgtctc tattctgaat atttcatata    480
aaggagtcct atcatatggg ccttttacgt ctaccttctt tcacttagca tcatgttttt    540
aagattcatc acagtgtag cacgtgtcag ttaattcatt tcatcttatg ctggataat     600 gctctattgt atgcatatcc ctcactttgc ttatccattc atcaactgat tgacatttgg    660
gttatttcta cttttgact attatgagta atgctgctat gaacattcct gtaccaatcg    720
ttacgtggac atatgctttc aattctcctg agtatgtaac tagggttgga gttgctgggt    780
catatgttaa ctcagtgttt cattttttg aagaactacc aaatggtttt ccaaagtgga    840
tgcaacactt tacattccca ccagcaagat atgaaggttc caatgtctct acattttgc    900 caacacttgt gatttctttt tatttattta tttatttatt tattttgag atggagtctc    960 actctgtcac ccaggctgga gtgcagtggc acaatttcag ctcactgcaa tctccacctc   1020
tcgggctcaa gcgatactcc tgcctcaacc tcccgagtaa ctgggattac aggcgcccac   1080
caccacacca agctaatttt ttgtattttt agtagagacg gggtttcatc atgtcggcca   1140
ggntgtactc gaactctgac ctcaagt                                        1167

<210> SEQ ID NO 11
<211> LENGTH: 1377
<212> TYPE: DNA
<213> ORGANISM: Homo sapiens
<220> FEATURE:
<221> NAME/KEY: misc_feature
<223> OTHER INFORMATION: sequence of STAR11

<400> SEQUENCE: 11
aggatcactt gagcccagga gttcaagacc agcctgggca acatagcgag aacatgtctc      60
aaaaaggaaa aaaatggggg aaaaaaccct cccagggaca gatatccaca gccagtcttg     120
ataagctcca tcattttaaa gtgcaaggcg gtgcctccca tgtggatgat tatttaatcc     180
tcttgtactt tgtttagtcc tttgtggaaa tgcccatctt ataaattaat agaattctag     240
aatctaatta aaatggttca actctacatt ttactttagg ataatatcag gaccatcaca     300
gaatgtctga gatgtggatt taccctatct gtagctcact tcttcaacca ttcttttagc     360
aaggctagtt atcttcagtg acaaccccctt gctgccctct actatctcct ccctcagatg    420
gactactctg attaagcttg agctagaata agcatgttat cccgggattt catatggaat    480 atttttataca tgagtgagcc attatgagtt gtttgaaaat ttattatgtt gagggagggt    540
aaccgctgta acaaccatca ccaaatctaa tcgactgaat acatttgacg tttatttctt    600
gttcacctga cagttcagtg ttacctaaat ttacatgaag acccagaggc ccacgctcct    660
tcatttgggg ctccaccgac ctccaaggtt tcagggccct ctgccccgcc ttctgcaccc    720
acaggggaag agagtggagg atgcacacgc ccaggcctgg aagtgacgca tgtggcttcc    780
```

```
ccgtccacag acttcaccca cagtccattg gccttcttaa gtcatggact cctgctgagc     840
tgccagggtg catgggaaat ccatgtgact gtgtgccctg gaggaagggg agcgtttcgg     900
tgagcacaca ggagtctttg ccactagacg ctgatgagga ttccccacag gcgatgaagc     960
atggagactc atcttgtaac aaacagatga gttgttgaca tctcttaagt ttactttgtg    1020
tgcagttttt attcagatag gaaaggctgt taaaatctta acacctaact ggaagaaggg    1080
ttttagagaa gtgtggtttt cagtaagcca gttctttcca caatccaaga aacgaaataa    1140
atttccagca tggagcagtt ggcaggtaag gttttgttg tggtctcgcc caggcttgag     1200
tgtaaccggt gtggtcatag ctcactacat tctcaaactc ctggccttaa gtcatcctcc    1260
tgcctcagcc tcccaaaggc aagtaaggtt aagaataggg gaaaggtgaa gtttcacagc    1320
ttttctagaa ttcttttat tcaagggact ctcagatcat caaacccacc cagaatc       1377
```

<210> SEQ ID NO 12
<211> LENGTH: 1051
<212> TYPE: DNA
<213> ORGANISM: Homo sapiens
<220> FEATURE:
<221> NAME/KEY: misc_feature
<223> OTHER INFORMATION: sequence of STAR12

<400> SEQUENCE: 12

```
atcctgcttc tgggaagaga gtggcctccc ttgtgcaggt gactttggca ggaccagcag      60
aaacccaggt ttcctgtcag gaggaagtgc tcagcttatc tctgtgaagg gtcgtgataa     120
ggcacgagga ggcaggggct tgccaggatg ttgcctttct gtgccatatg ggacatctca     180
gcttacgttg ttaagaaata tttggcaaga agatgcacac agaatttctg taacgaatag     240
gatggagttt taagggttac tacgaaaaaa agaaaactac tggagaagag ggaagccaaa     300
caccaccaag tttgaaatcg attttattgg acgaatgtct cactttaaat ttaaatggag     360
tccaacttcc ttttctcacc cagacgtcga gaaggtggca ttcaaaatgt ttacacttgt     420
ttcatctgcc tttttgctaa gtcctggtcc cctacctcct ttccctcact tcacatttgt     480
cgtttcatcg cacacatatg ctcatcttta tatttacata tatataattt ttatatatgg     540
cttgtgaaat atgccagacg agggatgaaa tagtcctgaa aacagctgga aaattatgca     600
acagtgggga gattgggcac atgtacattc tgtactgcaa agttgcacaa cagaccaagt     660
ttgttataag tgaggctggg tggttttat tttttctcta ggacaacagc ttgcctggtg     720
gagtaggcct cctgcagaag gcattttctt aggagcctca acttccccaa gaagaggaga    780
gggcgagact ggagttgtgc tggcagcaca gagacaaggg ggcacggcag gactgcagcc    840
tgcagagggg ctggagaagc ggaggctggc acccagtggc cagcgaggcc caggtccaag    900
tccagcgagg tcgaggtcta gagtacagca aggccaaggt ccaaggtcag tgagtctaag    960
gtccatggtc agtgaggctg agacccaggg tccaatgagg ccaaggtcca gagtccagta   1020
aggccgagat ccagggtcca gggaggtcaa g                                  1051
```

<210> SEQ ID NO 13
<211> LENGTH: 1291
<212> TYPE: DNA
<213> ORGANISM: Homo sapiens
<220> FEATURE:
<221> NAME/KEY: misc_feature
<223> OTHER INFORMATION: sequence of STAR13

<400> SEQUENCE: 13

```
agccactgag gtcctaactg cagccaaggg gccgttctgc acatgtcgct caccctctgt      60
gctctgttcc ccacagagca aacgcacatg gcaacgttgg tccgctcagc cactggttct     120
gtggtggaac ggtggatgtc tgcactgtga catcagctga gtaagtaaca acgactgagg     180
atgccgctga cccagggctg gggaagggga ctcccagctc agacaggctt ggctgtggtt     240
tgctttggga ggagagtgaa catcacaggg aatggctcat gtcagcccca ggagggtggg     300
ctggccctg gtccccgggc tccttctggc cctgcaggcg atagagagcc tcaacctgct     360
gccgcttctc cttggcccgg gtgatggccg tctggaagag cctgcagtag aggtgcacag     420
ccagcggaga gtcgtcattg ccgggtacag ggtaggtgat gaggcagggg ttgcagttgg     480
tgtccacgat gcccactgtg gggatgttca tcttggctgc gtctctcacg ccacgtgtg     540
gctcaaagat gttgttgagc gtgtgcagga agatgatgag gtccggcagg cggaccgtgg     600
ggccaaagag gaggcgcgcg ttggtcagca tgccgcccct gaagtagcga gtgtgggcgt     660
actcgccaca gtcacgggcc atgttctcaa tcaggtacga gaactgccgg ttgcggctta     720
taaacaagat gatgcccttg cggtaggcca tgtgggcggt gaagttcaag gccagctgga     780
ggtgcgtggc tgtctgttcc aggtcgatga tgtcgtggtc caggcggctc ccaaagatgt     840
acggctccat aaacctgcca gagacccac caaggcaagg gggatgagag ttcacggggc     900
catctccact ggctccttgc aggaacacag acgcccacca gggactcccg ggctcctctg     960
tgggggcact atgggctggg aagcacaatt gcaacgctc cccgtgtgca tggacagcag    1020
tgcagaccca tccaggccac ccctctgcat gcctcgtctc gtggcttaac ccctcctacc    1080
ctctacctct tcccgaagga atcctaatag aactgacccc atatggatgt gtggacatcc    1140
aacatgacgc caaaaggaca ttctgccccg tgcagctcac agggcagccg cctccgtcac    1200
tgtcctcttc ccgaggcttt gcggatgagg ccctctgggg gttggactta gcggggtgct    1260
ctgggccaaa agcattaagg gatcagggca g                                   1291
```

<210> SEQ ID NO 14
<211> LENGTH: 711
<212> TYPE: DNA
<213> ORGANISM: Homo sapiens
<220> FEATURE:
<221> NAME/KEY: misc_feature
<223> OTHER INFORMATION: sequence of STAR14

<400> SEQUENCE: 14

```
ccctggacca gggtccgtgg tcttggtggg cactggcttc ttcttgctgg gtgttttcct      60
gtgggtctct ggcaaggcac ttttgtggc gctgcttgtg ctgtgtgcgg gaggggcagg     120
tgctctttcc tcttggagct ggaccctctg gggcggtcc ccgtcggcct ccttgtgtgt     180
tttctgcacc tggtacagct ggatggcctc ctcaatgccg tcgtcgctgc tggagtcgga     240
cgcctcgggc gcctgtacgg cgctcgtgac tcgctttccc ctccttgcgg tgctggcgtt     300
cctttaatc ccacttttat tctgtactgc ttctgaaggg cggtggggt tgctggcttt     360
gtgctgccct ccttctcctg cgtggtcgtg gtcgtgacct tggacctgag gcttctgggc     420
tgcacgtttg tctttgctaa ccgggggagg tctgcagaag gcgaactcct tctggacgcc     480
catcaggccc tgccggtgca ccacctttgt agccggctct tggtgggatt tcgagagtga     540
cttcgccgaa ttttcatgtg tgtctggttt cttctccact gacccatcac atttttgggt     600
```

```
ctcatgctgt cttttctcat tcagaaactg ttctatttct gccctgatgc tctgctcaaa    660
ggagtctgct ctgctcatgc tgactgggga ggcagagccc tggtccttgc t             711

<210> SEQ ID NO 15
<211> LENGTH: 1876
<212> TYPE: DNA
<213> ORGANISM: Homo sapiens
<220> FEATURE:
<221> NAME/KEY: misc_feature
<223> OTHER INFORMATION: sequence of STAR15

<400> SEQUENCE: 15
gagtccaaga tcaaggtgcc agcatcttgt gagggccttc ttgttacgtc actccctagc     60
gaaagggcaa agagagggtg agcaagagaa aggggggctg aactcgtcct tgtagaagag    120
gcccattccc gagacaatgg cattcatcca ttcactccac cctcatggcc tcaccacctc    180
tcatgaggct ccacctccca gccctggttt gttggggatt aaatttccaa cacatgcctt    240
ttgggggaca tgttaaaatt atagcacccc aaatgttaca ctatcttttg atgagcggta    300
gttctgattt taagtctagc tggcctactt tttcttgcac gtgggatgct ttctgcctgt    360
tccagggcag gcagctcttc tctgtccctc tgctggcccc acctcatcct ctgttgtcct    420
cttccctcct tctgtgccct ggggtcctgg tgggggtgtg actgtcaact gcgttgggct    480 aactttttc cctgctggtg gcccgtaatg aaagaaagct tcttgctccc aagttcctta    540
aatccaagct catagacaac gcggtctcac agcaggcctg gggccagcct cacgtgagcc    600
ccttccctgg tgtagtcact ggcatggggg aatgggattt cctgttgccc tactgtgtgg    660
ctgaggtggg ggttgcttcc tggagccagg ccttgtggaa gggcagtgcc cactgcagtg    720
gatgctgggc cctgaatctg accccagtgt tcattggctc tgtgagaccc agtgagggca    780
gggagggaag tggagctggg gtgagaagta gaggccctgc agggcccacg tgccagccac    840
caggcctcag actaggctca gatgacggag agctgcacac ctgcccaacc caggccctgc    900
agtgcccaca tgccagccgc tggggcccag acttgctcca gagggcggag agctttacac    960
cggcccaacc caggccatgg ctccaaatgc gtgacagttt tgctgttgct cttttagtc   1020 attgtcaagt tgatgcttgt tttgcagagg accaaggctt tatgaaccta ttccctgtg   1080 tgaagagttt caccaggtta tggaaatttc tttaaaacca taccacagtt ttttcattat   1140
tcatgtatat ttttaaaaat aattactgca ctcagtagaa taacatgaaa atgttgcctg   1200
ttagcccttt tccagtttgc cccgagaata ctggggcac ttgtggctgc aatgtttatc   1260
ctgcggcagc tttgccatga agtatctcac tttttattatt attttttgcat tgctcgagta   1320 tattgacttt ggaaacaaaa gacatcattc tatttatagc attatgtttt tagtagtggt   1380
atttccatat acaagataca gtaattttcc gtcaatgaaa atgtcaaatt ctagaaaatg   1440
taacattcct atgcgtggtg ttaacatcgt tctctaacag ttgttggccg aagattcgtt   1500
tgatgaatcc gattttccca aaatagccga ttctgatgat tcagacgatt ctgatgttct   1560
gtttagaaat aattccaaga acagttttta catttatttt tcacattgaa aatcagtcag   1620
atttgcttca gcctcaaaga gcacgtttat gtaaaattaa atgagtgctg gcagccagct   1680
gcgctttgtt tttctaaatg ggaaaagggt taaatttcac tcagctttta aatgacagcg   1740
cacagcctgt gtcatagagg gttggaggag atgactttaa ctgcctgtgg ttaggatccc   1800
tttcccccag gaatgtctgg gagcccactg ccgggtttgc tgtccgtctc gtttggactc   1860
agttctgcat gtactg                                                   1876
```

```
<210> SEQ ID NO 16
<211> LENGTH: 1282
<212> TYPE: DNA
<213> ORGANISM: Homo sapiens
<220> FEATURE:
<221> NAME/KEY: misc_feature
<223> OTHER INFORMATION: sequence of STAR16

<400> SEQUENCE: 16
cgcccacctc ggcttttccaa agtgctggga ttacaggcat gagtcactgc gcccatcctg     60
attccaagtc tttagataat aacttaactt tttcgaccaa ttgccaatca ggcaatcttt    120
gaatctgcct atgacctagg acatccctct ccctacaagt tgccccgcgt ttccagacca    180
aaccaatgta catcttacat gtattgattg aagttttaca tctccctaaa acatataaaa    240
ccaagctata gtctgaccac ctcaggcacg tgttctcagg acctccctgg ggctatggca    300
tgggtcctgg tcctcagatt tggctcagaa taaatctctt caaatatttt ccagaatttt    360
actcttttca tcaccattac ctatcaccca taagtcagag ttttccacaa ccccttcctc    420
agattcagta atttgctaga atggccacca aactcaggaa agtatttttac ttacaattac    480 caatttatta tgaagaactc aaatcaggaa tagccaaatg gaagaggcat agggaaaggt    540
atggaggaag gggcacaaag cttccatgcc ctgtgtgcac accaccctct cagcatcttc    600
atgtgttcac caactcagaa gctcttcaaa cttttgtcatt taggggttttt tatggcagtt    660 ccactatgta ggcatggttg ataaatcact ggtcatcggt gatagaactc tgtctccagc    720
tcctctctct ctcctcccca gaagtcctga ggtgggctg aaagtttcac aaggttagtt    780
gctctgacaa ccagccccta tcctgaagct attgagggt cccccaaaag ttaccttagt    840
atggttggaa gaggcttatt atgaataaca aaagatgctc ctattttttac cactagggag    900 catatccaag tcttgcggga acaaagcatg ttactggtag caaattcata caggtagata    960
gcaatctcaa ttcttgcctt ctcagaagaa agaatttgac caaggggggca taaggcagag   1020 tgagggacca agataagttt tagagcagga gtgaaagttt attaaaaagt tttaggcagg   1080
aatgaaagaa agtaaagtac atttggaaga gggccaagtg ggcgacatga gagagtcaaa   1140
caccatgccc tgtttgatgt ttggcttggg gtcttatatg atgacatgct tctgagggtt   1200
gcatccttct ccctgattc ttcccttggg gtgggctgtc cgcatgcaca atggcctgcc   1260
agcagtaggg aggggccgca tg                                             1282

<210> SEQ ID NO 17
<211> LENGTH: 793
<212> TYPE: DNA
<213> ORGANISM: Homo sapiens
<220> FEATURE:
<221> NAME/KEY: misc_feature
<223> OTHER INFORMATION: sequence of STAR17

<400> SEQUENCE: 17
atccgagggg aggaggagaa gaggaaggcg agcagggcgc cggagcccga ggtgtctgcg     60
agaactgttt taaatggttg gcttgaaaat gtcactagtg ctaagtggct tttcggattg    120
tcttatttat tactttgtca ggtttcctta aggagagggt gtgttggggg tgggggagga    180
ggtggactgg ggaaacctct gcgtttctcc tcctcggctg cacagggtga gtaggaaacg    240
cctcgctgcc acttaacaat ccctctatta gtaaatctac gcggagactc tatgggaagc    300
cgagaaccag tgtcttcttc cagggcagaa gtcacctgtt gggaacggcc cccgggtccc    360
cctgctgggc tttccggctc ttctaggcgg cctgatttct cctcagccct ccacccagcg    420
```

```
tccctcaggg acttttcaca cctccccacc cccatttcca ctacagtctc ccagggcaca      480
gcacttcatt gacagccaca cgagccttct cgttctcttc cctctgttc cttctctttc       540 tcttctcctc tgttccttct ctttctctgt cataatttcc ttggtgcttt cgccaccttc      600
aacaaaaaag agaaaaaaat aaaataaaaa aacccattc tgagccaaag tattttaaga      660
tgaatccaag aaagcgaccc acatagccct ccccacccac ggagtgcgcc aagacgcacc      720
caggctccat cacagggccg agagcagcgc cactctggtc gtactttggg gtcaagagat     780
cttgcaaaag agg                                                         793

<210> SEQ ID NO 18
<211> LENGTH: 492
<212> TYPE: DNA
<213> ORGANISM: Homo sapiens
<220> FEATURE:
<221> NAME/KEY: misc_feature
<223> OTHER INFORMATION: sequence of STAR18

<400> SEQUENCE: 18 atcttttgc tctctaaatg tattgatggg ttgtgttttt tttcccacct gctaataaat       60
attacattgc aacattcttc cctcaacttc aaaactgctg aactgaaaca atatgcataa     120
aagaaaatcc tttgcagaag aaaaaaagct attttctccc actgattttg aatggcactt    180
gcggatgcag ttcgcaaatc ctattgccta ttccctcatg aacattgtga atgaaacct     240 ttggacagtc tgccgcattg cgcatgagac tgcctgcgca aggcaagggt atggttccca     300
aagcacccag tggtaaatcc taacttatta ttcccttaaa attccaatgt aacaacgtgg     360
gccataaaag agtttctgaa caaaacatgt catctttgtg gaaggtgtt tttcgtaatt     420 aatgatggaa tcatgctcat ttcaaaatgg aggtccacga tttgtggcca gctgatgcct    480
gcaaattatc ct                                                          492

<210> SEQ ID NO 19
<211> LENGTH: 1840
<212> TYPE: DNA
<213> ORGANISM: Homo sapiens
<220> FEATURE:
<221> NAME/KEY: misc_feature
<223> OTHER INFORMATION: sequence of STAR19

<400> SEQUENCE: 19
tcacttcctg atattttaca ttcaaggcta gctttatgca tatgcaacct gtgcagttgc      60
acagggcttt gtgttcagaa agactagctc ttggtttaat actctgttgt tgccatcttg     120
agattcatta taatataatt tttgaatttg tgttttgaac gtgatgtcca atgggacaat     180
ggaacattca cataacagag gagacaggtc aggtggcagc ctcaattcct tgccaccctt     240
ttcacataca gcattggcaa tgccccatga gcacaaaatt tgggggaacc atgatgctaa     300
gactcaaagc acatataaac atgttacctc tgtgactaaa agaagtggag gtgctgacag     360
cccccagagg ccacagttta tgttcaaacc aaaacttgct tagggtgcag aaagaaggca     420
atggcagggt ctaagaaaca gcccatcata tccttgttta ttcatgttac gtccctgcat     480
gaactaatca cttacactga aaatattgac agaggaggaa atggaaagat agggcaaccc     540
atagttcttt ttccttttag tctttcctta tcagtaaacc aaagatagta ttggtaaaat     600
gtgtgtgagt taattaatga gttagtttta ggcagtgttt ccactgttgg ggtaagaaca     660
aaatatatag gcttgtattg agctattaaa tgtaaattgt ggaatgtcag tgattccaag     720
tatgaattaa atatccttgt atttgcattt aaaattggca ctgaacaaca aagattaaca     780
```

```
gtaaaattaa taatgtaaaa gtttaatttt tacttagaat gacattaaat agcaaataaa    840
agcaccatga taaatcaaga gagagactgt ggaaagaagg aaaacgtttt tattttagta    900
tatttaatgg gactttcttc ctgatgtttt gttttgtttt gagagagagg gatgtggggg    960
cagggaggtc tcattttgtt gcccaggctg gacttgaact cctgggctcc agctatcctg   1020
ccttagcttc ttgagtagct gggactacag gcacacacca cagtgtctga cattttctgg   1080
attttttttt tttttttatt tttttgtgta gacaggttct ggctctgtta ctcaggttgc   1140
agtgcagtgg catgatagcg gctcactgca gcctcaacct cctcagctta agctactctc   1200
ccacttcagc ctcctgagta gccaggacta cagttgtgtg ccaccacacc tgtggctaat   1260
ttttgtagag atggggtctc tccacgttgc cgaggctggt ctccaactcc tggtctcaag   1320
cgaacctcct gacttggcct cccgaagtgc tgggattaca ggcttgagcc actgcatcca   1380
gcctgtcctc tgtgttaaac ctactccaat tgtctttca tctctacata aacggctctt    1440
ttcaaagttc ccatagacct cactgttgct aatctaataa taaattatct gccttttctt   1500
acatggttca tcagtagcag cattagattg ggctgctcaa ttcttcttgg tatattttct   1560
tcatttggct tctggggcat cacactctct ttgagttact cattcctcat tgatagcttc   1620
ttcctagtct tctttactgg ttcttcctct tctccctgac tccttaatat tgttttctc    1680 cccaggcttt agttcttagt cctcttctgt tatctattta cacccaattc tttcagagtc   1740
tcatccagag tcatgaactt aaacctgttt ctgtgcagat aattcacatt attatatctc   1800
cagcccagac tctcccgcaa actgcagact gatcctactg                         1840

<210> SEQ ID NO 20
<211> LENGTH: 780
<212> TYPE: DNA
<213> ORGANISM: Homo sapiens
<220> FEATURE:
<221> NAME/KEY: misc_feature
<223> OTHER INFORMATION: sequence of STAR20

<400> SEQUENCE: 20
gatctcaagt ttcaatatca tgttttggca aaacattcga tgctcccaca tccttaccta     60
aagctaccag aaaggctttg ggaactgtca acagagctac agaaaagtca gtaaagacca    120
atggacccct caaacaaaaa cagccaagct tttctgccaa aaagatgact gagaagactg    180
ttaaagcaaa aaactctgtt cctgcctcag atgatggcta tccagaaata gaaaaattat    240
ttcccttcaa tcctctaggc ttcgagagtt ttgacctgcc tgaagagcac cagattgcac    300
atctcccctt gagtgaagtg cctctcatga tacttgatga ggagagagag cttgaaaagc    360
tgtttcagct gggcccccct tcacctttga agatgccctc tccaccatgg aaatccaatc    420
tgttgcagtc tcctttaagc attctgttga ccctggatgt tgaattgcca cctgtttgct    480
ctgacataga tatttaaatt tcttagtgct ttagagtttg tgtatatttc tattaataaa    540
gcattatttg tttaacagaa aaaagatat atacttaaat cctaaaataa aataaccatt    600
aaaaggaaaa acaggagtta taactaataa gggaacaaag gacataaaat gggataataa    660
tgcttaatcc aaaataaagc agaaaatgaa gaaaatgaa atgaagaaca gataaataga    720
aaacaaatag caatatgaaa gacaaacttg accgggtgtg gtggctgatg cctgtaatcc    780

<210> SEQ ID NO 21
<211> LENGTH: 607
<212> TYPE: DNA
<213> ORGANISM: Homo sapiens
```

```
<220> FEATURE:
<221> NAME/KEY: misc_feature
<223> OTHER INFORMATION: sequence of STAR21

<400> SEQUENCE: 21
gatcaataat ttgtaatagt cagtgaatac aaaggggtat atactaaatg ctacagaaat      60
tccattcctg ggtataaatc ctagacatat ttatgcatat gtacaccaag atatatctgc    120
aagaatgttc acagcaaatc tctttgtagt agcaaaaggc caaaaggtct atcaacaaga    180
aaattaatac attgtggcac ataatggcat ccttatgcca ataaaatgg atgaaattat     240 agttaggttc aaaaggcaag cctccagata atttatatca tataattcca tgtcaaacat    300
tcaacaacaa gcaaaactaa acatatacaa atgtcaggga aaatgatgaa caaggttaga    360
aaatgattaa tataaaaata ctgcacagtg ataacattta atgagaaaaa aagaaggaag    420
ggcttaggga gggacctaca gggaactcca agttcatgg taagtactaa atacataatc     480
aaagcactca aaatagaaaa tattttagta atgttttagc tagttaatat cttacttaaa    540
acaaggtcta ggccaggcac ggtggctcac acctgtaatc ccagcacttt gggaggctga    600
ggcgggt                                                              607

<210> SEQ ID NO 22
<211> LENGTH: 1380
<212> TYPE: DNA
<213> ORGANISM: Homo sapiens
<220> FEATURE:
<221> NAME/KEY: misc_feature
<223> OTHER INFORMATION: sequence of STAR22

<400> SEQUENCE: 22
cccttgtgat ccacccgcct tggcctccca aagtgctggg attacaggcg tgagtcacta     60
cgcccggcca ccctccctgt atattatttc taagtatact attatgttaa aaaagtttta   120 aaatattga tttaatgaat tcccagaaac taggattta catgtcacgt tttcttatta     180
taaaaataaa aatcaacaat aaatatatgg taaaagtaaa aagaaaaaca aaaacaaaaa    240
gtgaaaaaaa taaacaacac tcctgtcaaa aacaacagt tgtgataaaa cttaagtgcc     300
tgaaaattta gaaacatcct tctaaagaag ttctgaataa aataaggaat aaaataatca    360
catagttttg gtcattggtt ctgtttatgt gatggattat gttattgat ttgtgtatgt     420 tgaacttatc tcaatagatg cagacaaggc cttgataaaa gttttaaca ccttttcatg     480 ttgaaaactc tcaatagact aggtattgat gaaacatatc tcaaaataat agaagctatt    540
tatgataaac ccatagccaa tatcatactg agtgggcaaa agctggaagc attcccttg    600 aaaactggca agacaagg atgccctctc tcaccactcc tattaaatgt agtattggaa      660
gttctggcca gagcaatcag gcaggagaaa gaaaaggtat taaaatagga agagaggaag    720
tcaaattgtc tctgtttgca gtaaacatga ttgtatattt agaaaacccc attgtctcat    780
cctaaaaact ccttaagctg ataaacaact tcagcaaagt ctcaggatac aaaatcaatg    840
tgcaaaaatc acaagcattc ctatacaccg ataatagaca gcagagagcc aaatcatgag    900
tgaagtccca ttcacaattg cttcaaagaa aataaaatac ttaggaatac aactttcacg    960
ggacatgaag gacattttca aggacaacta aaaaccactg ctcaaggaaa tgagagagga   1020
cacaaagaaa tggaaaaaca ttccatgctc atggaagaat caatatcatg aaaatggcca   1080
tactgcccaa agtaatttat agattcaatg ctaaccccat caagccacca ttgactttct   1140
tcacagaact agaaaaaaac tattttaaaa ctcatatgta gtcaaaaaga gtcggtatag   1200
```

```
ccaagacaat cctaagcata aagaacaaag ctggatgcat cacgctgact tcaaaccata   1260
ctacaaggct acagtaacca aaacagcatg gtactgtac caaaacagat agatagaccg   1320
atagaacaga acagaggcct cggaaataac accacacatc tacaacccctt tgatcttcaa   1380
```

```
<210> SEQ ID NO 23
<211> LENGTH: 1246
<212> TYPE: DNA
<213> ORGANISM: Homo sapiens
<220> FEATURE:
<221> NAME/KEY: misc_feature
<223> OTHER INFORMATION: sequence of STAR23

<400> SEQUENCE: 23
atcccctcat ccttcagggc agctgagcag ggcctcgagc agctggggga gcctcactta     60
atgctcctgg gagggcagcc agggagcatg gggtctgcag gcatggtcca gggtcctgca    120
ggcggcacgc accatgtgca gccgccccca cctgttgctc tgcctccgcc acctggccat    180
gggcttcagc agccagccac aaagtctgca gctgctgtac atggacaaga agcccacaag    240
cagctagagg accttgtgtt ccacgtgccc agggagcatg gcccacagcc aaagaccag    300 tcaggagcag gcaggggctt ctggcaggcc cagctctacc tctgtcttca cacagatggg    360
agatttctgt tgtgattttg agtgatgtgc ccctttggtg acatccaaga tagttgctga    420
agcaccgctc taacaatgtg tgtgtattct gaaaacgaga acttctttat tctgaaataa    480
ttgatgcaaa ataaattagt ttggatttga aattctattc atgtaggcat gcacacaaaa    540
gtccaacatt gcatatgaca caaagaaaag aaaaagcttg cattccttaa atacaaatat    600
ctgttaacta tatttgcaaa tatatttgaa tacacttcta ttatgttaca tataatatta    660
tatgtatatg tatatataat atacatatat atgttacata taatatactt ctattatgtt    720
acatataata tttatctata agtaaataca taaatataaaa gatttgagta gctgtagaac    780
attgtcttat gtgttatcag ctactactac aaaaatatct cttccactta tgccagtttg    840
ccatataaat atgatcttct cattgatggc ccagggcaag agtgcagtgg gtacttattc    900
tctgtgagga gggaggagaa aagggaacaa ggagaaagtc acaaagggaa aactctggtg    960
ttgccaaaat gtcaagtttc acatattccg agacggaaaa tgacatgtcc cacagaagga   1020
ccctgcccag ctaatgtgtc acagatatct caggaagctt aaatgatttt tttaaaagaa   1080
aagagatggc attgtcactt gtttcttgta gctgaggctg tgggatgatg cagatttctg   1140
gaaggcaaag agctcctgct ttttccacac cgagggactt tcaggaatga ggccagggtg   1200
ctgagcacta caccaggaaa tccctggaga gtgtttttct tactta                  1246
```

```
<210> SEQ ID NO 24
<211> LENGTH: 939
<212> TYPE: DNA
<213> ORGANISM: Homo sapiens
<220> FEATURE:
<221> NAME/KEY: misc_feature
<223> OTHER INFORMATION: sequence of STAR24

<400> SEQUENCE: 24
acgaggtcac gagttcgaga ccagcctggc caagatggtg aagccctgtc tctactaaaa     60
atacaacaag tagccgggcg cggtgacggg cgcctgtaat cccagctact caggaggctg    120
aagcaggaga atctctagaa cccaggaggc ggaggtgcag tgagctgaga ctgccccgct    180
gcactctagc ctgggcaaca cagcaagact ctgtctcaaa taaataaata aataaataaa    240
taaataaata aataaataaa tagaaaggga gagttggaag tagatgaaag agaagaaaag    300
```

```
aaatcctaga tttcctatct gaaggcacca tgaagatgaa ggccacctct tctgggccag      360
gtcctcccgt tgcaggtgaa ccgagttctg gcctccattg gagaccaaag gagatgactt      420
tggcctggct cctagtgagg aagccatgcc tagtcctgtt ctgtttgggc ttgatcctgt      480
atcacttgat tgtctctcct ggactttcca tggattccag ggatgcaact gagaagttta      540 ttttaatgc acttacttga agtaagagtt atttttaaaac attttagcaa aggaaatgaa      600
ttctgacagg ttttgcactg aagacattca catgtgagga aaacaggaaa accactatgc      660
tagaaaaagc aaatgctgtt gagattgtct cacaaacaca aattgcgtgc cagcaggtag      720
gtttgagcct caggttgggc acattttacc ttaagcgcac tgttggtgga acttaaggtg      780
actgtaggac ttatatatac atacatacat ataatatata tacatattta tgtgtatata      840
cacacacaca cacacacaca cacacagggt cttgctatct tgcccagggt ggtctccaac      900
tctgggtctc aagcgatcct ctgcctcccc ttcccaaag                             939
```

```
<210> SEQ ID NO 25
<211> LENGTH: 1067
<212> TYPE: DNA
<213> ORGANISM: Homo sapiens
<220> FEATURE:
<221> NAME/KEY: misc_feature
<223> OTHER INFORMATION: sequence of STAR25

<400> SEQUENCE: 25
```

```
cagcccctct tgtgttttc tttatttctc gtacacacac gcagttttaa gggtgatgtg      60
tgtataatta aaaggaccct tggcccatac tttcctaatt ctttagggac tgggattggg     120
tttgactgaa atatgttttg gtggggatgg gacggtggac ttccattctc cctaaactgg     180
agttttggtc ggtaatcaaa actaaaagaa acctctggga gactgaaaac ctgattggag     240
cactgaggaa caagggaatg aaaaggcaga ctctctgaac gtttgatgaa atggactctt     300
gtgaaaatta acagtgaata ttcactgttg cactgtacga agtctctgaa atgtaattaa     360
aagtttttat tgagcccccg agctttggct tgcgcgtatt tttccggtcg cggacatccc     420
accgcgcaga gcctcgcctc cccgctgccc tcagcctccg atgacttccc cgcccccgcc     480
ctgctcggtg acagacgttc tactgcttcc aatcggaggc accttcgcg ggagcggcca      540 atcgggagct ccggcaggcg gggaggccgg gccagttaga tttggaggtt caacttcaac     600
atggccgaag caagtagcgc caatctaggc agcggctgtg aggaaaaaag gcatgagggg     660
tcgtcttcgg aatctgtgcc acccggcact accatttcga gggtgaagct cctcgacacc     720
atggtggaca cttttcttca gaagctggtc gccgccggca ggtaaagtgg acgcagccgc     780
ggtgggagtg tttgttggca ccgaagctca atcccgcga ggtcaggacg ccgcaggct       840 ggcgcgcggt gacgtgggtc cgcgttgggg gcggggcagt cggacgaggc gacccagtca    900
aatcctgagc ttaggagtc agggtattca cgcactgata acctgtagcg gaccgggata     960
gctagctact ccttcctaca ggaagccccg ttttcactaa aatttcaggt ggttgggagg   1020
aaagatagag cctttgcaaa ttagagcagg gttttttatt tttttat                 1067
```

```
<210> SEQ ID NO 26
<211> LENGTH: 540
<212> TYPE: DNA
<213> ORGANISM: Homo sapiens
<220> FEATURE:
<221> NAME/KEY: misc_feature
<223> OTHER INFORMATION: sequence of STAR26
```

<400> SEQUENCE: 26

```
cccccctgaca agccccagtg tgtgatgttc cccactctgt gtccatgcat tctcattgtt      60
caactcccat ctgtgagtga gaacatgcag tgtttggttt tctgtccttg agatagtttg     120
ctgagaatga tggtttccag cttcatccat gtccttgcaa aggaagtgaa cttatccttt     180
tttatggctt catagtattc catggcacat atgtgccaca ttttttaat ccagtctatc      240
attgatggac atttggttg gttccaagtc tttgctattg tgaatagcac cacaattaac      300
atatgtgtgc atgtatacat ctttatagta gcatgattta taatccttcg ggtatatacc     360
ctgtaatggg atcgctgggt caaatggtat ttctagttct agatccttga ggaatcacca     420
cactgctttc cacaatggtt gaactaattt acgctcccac cagcagtgta aaagcattcc     480
tatttctcca cgtcctctcc agtatctgtt gtttcctgac tttttaatga tcatcattct     540
```

<210> SEQ ID NO 27
<211> LENGTH: 1520
<212> TYPE: DNA
<213> ORGANISM: Homo sapiens
<220> FEATURE:
<221> NAME/KEY: misc_feature
<223> OTHER INFORMATION: sequence of STAR27

<400> SEQUENCE: 27

```
cttggccctc acaaagcctg tgccaggga acaattagcg agctgcttat tttgctttgt       60
atccccaatg ctgggcataa tgcctgccat tatgagtaat gccggtagaa gtatgtgttc     120
aaggaccaaa gttgataaat accaaagaat ccagagaagg gagagaacat tgagtagagg     180
atagtgacag aagagatggg aacttctgac aagagttgtg aagatgtact aggcaggggg     240
aacagcttaa ggagagtcac acaggaccga gctcttgtca agccggctgc catggaggct     300
gggtggggcc atggtagctt tcccttcctt ctcaggttca gagtgtcagc cttgaacttc     360
taattcccag aggcatttat tcaatgtttt cttctagggg catacctgcc ctgctgtgga     420
agactttctt ccctgtgggt cgccccagtc cccagatgag acggtttggg tcagggccag     480
gtgcaccgtt gggtgtgtgc ttatgtctga tgacagttag ttactcagtc attagtcatt     540
gagggaggtg tggtaaagat ggagatgctg ggtcacatcc ctagagaggt gttccagtat     600
gggcacatgg gagggctgga aggataggtt actgctagac gtagagaagc cacatccttt     660
aacaccctgg cttttcccac tgccaagatc cagaaagtcc ttgtggtttc gctgctttct     720
cctttttttt tttttttttt tttctgagat ggagtctggc tctgtcgccc aggctggagt     780
gcagtggcac gatttcggct cactgcaagt tccgcctcct aggttcatac cattctccca     840
cctcagcctc ccgagtagct gggactacag gcgccaccac acccagctaa ttttttgtat     900
ttttagtaga cggcgtttt caccatgtta gccaggatgg tcttgatccg cctgcctcag     960
cctcccaaag tgctgggatt acaggcgtga gccaccgcgc ccggcctgct tcttctttc     1020
atgaagcatt cagctggtga aaaagctcag ccaggctggt ctggaactct tgacctcaag    1080
tgatctgcct gcctcagcct cccaaagtgc tgagattaca ggcatgagcc agtccgaatg    1140
tggcttttt tgttttgttt tgaaacaagg tctcactgtt gcccaggctg cagtgcagtg    1200
gcatacctca gctccactgc agcctcgacc tcctgggctc aagcaatcct cccaactgag    1260
cctccccagt agctggggct acaagcgcat gccaccacgc ctggctattt tttttttttt   1320
tttttttttt gagaaggagt ttcattcttg ttgcccaggc tggagtgcaa tggcacagtc    1380
tcagctcact gcagcctccg cctcctgggt tcaagcgatt ctcctgcctc agcctcccga    1440
```

| | |
|---|---|
| gtagctggga ttataggcac ctgccaccat gcctggctaa ttttttttgta tttttagtag | 1500 |
| ggatggggtt tcaccatgtt | 1520 |

<210> SEQ ID NO 28
<211> LENGTH: 961
<212> TYPE: DNA
<213> ORGANISM: Homo sapiens
<220> FEATURE:
<221> NAME/KEY: misc_feature
<223> OTHER INFORMATION: sequence of STAR28

<400> SEQUENCE: 28

| | |
|---|---|
| aggaggttat tcctgagcaa atggccagcc tagtgaactg gataaatgcc catgtaagat | 60 |
| ctgtttaccc tgagaagggc atttcctaac tctccctata aaatgccaag tggagcaccc | 120 |
| cagatgaaat agctgatatg ctttctatac aagccatcta ggactggctt tatcatgacc | 180 |
| aggatattca cccactgaat atggctatta cccaagttat ggtaaatgct gtagttaagg | 240 |
| gggtcccttc cacatggaca ccccaggtta taaccagaaa gggttcccaa tctagactcc | 300 |
| aagagagggt tcttagacct catgcaagaa agaacttggg gcaagtacat aaagtgaaag | 360 |
| caagtttatt aagaaagtaa agaaacaaaa aaatggctac tccataagca aagttatttc | 420 |
| tcacttatat gattaataag agatggatta ttcatgagtt ttctgggaaa ggggtgggca | 480 |
| attcctggaa ctgagggttc ctcccacttt tagaccatat agggtatctt cctgatattg | 540 |
| ccatggcatt tgtaaactgt catggcactg atgggagtgt cttttagcat tctaatgcat | 600 |
| tataattagc atataatgag cagtgaggat gaccagaggt cacttctgtt gccatattgg | 660 |
| tttcagtggg gtttggttgg cttttttttt tttttaacca caacctgttt tttatttatt | 720 |
| tatttattta tttatttatt tatattttt atttttttt agatggagtc ttgctctgtc | 780 |
| acccaggtta gagtgcagtg gcaccatctc ggctcactgc aagctctgcc tccttggttc | 840 |
| acgccattct gctgcctcag cctcccgagt agctgggact acaggtgcct gccaccatac | 900 |
| ccggctaatt ttttctattt ttcagtagag acggggtttc accgtgttag ccaggatggt | 960 |
| c | 961 |

<210> SEQ ID NO 29
<211> LENGTH: 2233
<212> TYPE: DNA
<213> ORGANISM: Homo sapiens
<220> FEATURE:
<221> NAME/KEY: misc_feature
<223> OTHER INFORMATION: sequence of STAR29

<400> SEQUENCE: 29

| | |
|---|---|
| agcttggaca cttgctgatg ccactttgga tgttgaaggg ccgccctctc ccacaccgct | 60 |
| ggccactttt aaatatgtcc cctctgccca gaagggcccc agaggagggg ctggtgaggg | 120 |
| tgacaggagt tgactgctct cacagcaggg ggttccggag ggaccttttc tccccattgg | 180 |
| gcagcataga aggacctaga agggccccct ccaagcccag ctgggcgtgc agggccagcg | 240 |
| attcgatgcc ttcccctgac tcaggtggcg ctgtcctaaa ggtgtgtgtg ttttctgttc | 300 |
| gccaggggt ggcggataca gtggagcatc gtgcccgaag tgtctgagcc cgtggtaagt | 360 |
| ccctggaggg tgcacggtct cctccgactg tctccatcac gtcaggcctc acagcctgta | 420 |
| ggcaccgctc ggggaagcct ctggatgagg ccatgtggtc atcccctgg agtcctggcc | 480 |
| tggcctgaag aggaggggag gaggaggcca gcccctccct agcccaagg cctgcgaggc | 540 |
| tgcaagcccg gccccacatt ctagtccagg cttggctgtg caagaagcag attgcctggc | 600 |

-continued

| | |
|---|---|
| cctggccagg cttcccagct aggatgtggt atggcagggg tgggggacat tgagggggctg | 660 |
| ctgtagcccc cacaacctcc ccaggtaggg tggtgaacag taggctggac aagtggacct | 720 |
| gttcccatct gagattcaag agcccacctc tcggaggttg cagtgagccg agatccctcc | 780 |
| actgcactcc agcctgggca acagagcaag actctgtctc aaaaaaacag aacaacgaca | 840 |
| acaaaaaacc cacctctggc ccactgccta actttgtaaa taaagttttta ttggcacata | 900 |
| gacacaccca ttcatttaca tactgctgcg gctgcttttg cattacccctt gagtagacga | 960 |
| cagaccacgt ggccatggaa gccaaaaata tttactgtct ggcccttttac agaagtctgc | 1020 |
| tctagaggga gaccccggcc catggggcag gaccactggg cgtgggcaga agggaggcct | 1080 |
| cggtgcctcc acgggcctag ttgggtatct cagtgcctgt ttcttgcatg gagcaccagg | 1140 |
| ggtcagggca agtacctgga ggaggcaggc tgttgcccgc ccagcactgg gacccaggag | 1200 |
| accttgagag gctcttaacg aatgggagac aagcaggacc agggctccca ttggctgggc | 1260 |
| ctcagtttcc ctgcctgtaa gtgagggagg gcagctgtga aggtgaactg tgaggcagag | 1320 |
| cctctgctca gccattgcag gggcggctct gccccactcc tgttgtgcac ccagagtgag | 1380 |
| gggcacgggg tgagatgtca ccatcagccc atagggggtgt cctcctggtg ccaggtcccc | 1440 |
| aagggatgtc ccatccccccc tggctgtgtg gggacagcag agtccctggg gctggggggg | 1500 |
| ctccacactg ttttgtcagt ggttttttctg aactgttaaa tttcagtgga aaattctctt | 1560 |
| tccccttttta ctgaaggaac ctccaaagga agacctgact gtgtctgaga agttccagct | 1620 |
| ggtgctggac gtcgcccaga aagcccaggt actgccacgg gcgccggcca ggggtgtgtc | 1680 |
| tgcgccagcc atgggcacca gccagggggtg tgtctacgcc ggccaggggt aggtctccgc | 1740 |
| cggcctccgc tgctgcctgg ggagggccgt gcctgacact gcaggcccgg tttgtccgcg | 1800 |
| gtcagctgac ttgtagtcac cctgcccttg gatggtcgtt acagcaactc tggtggttgg | 1860 |
| ggaagggggcc tcctgattca gcctctgcgg acgtgcgcg agggtggagc tccccctccct | 1920 |
| ccccaccgcc cctggccagg gttgaacgcc cctgggaagg actcaggccc gggtctgctg | 1980 |
| ttgctgtgag cgtggccacc tctgccctag accagagctg ggccttcccc ggcctaggag | 2040 |
| cagccgggca ggaccacagg gctccgagtg acctcagggc tgcccgacct ggaggccctc | 2100 |
| ctggcgtcgc ggtgtgactg acagcccagg agcgggggct gttgtaattg ctgtttctcc | 2160 |
| ttcacacaga accttttcgg gaagatggct gacatcctgg agaagatcaa gaagtaagtc | 2220 |
| ccgccccccca ccc | 2233 |

<210> SEQ ID NO 30
<211> LENGTH: 1851
<212> TYPE: DNA
<213> ORGANISM: Homo sapiens
<220> FEATURE:
<221> NAME/KEY: misc_feature
<223> OTHER INFORMATION: sequence of STAR30

<400> SEQUENCE: 30

| | |
|---|---|
| gggtgcattt ccacccaggg gacacttggc aatggtggga gacattgctt gttgtcacaa | 60 |
| ctgggcatgg gagtgctgct gcgtctagtg ggtagaggcc agagatgctc ctaatatcct | 120 |
| acaaggcaca gaacagcccc ccacaacaga gaattatcca gcctgaaaat gtccacagtg | 180 |
| ctgaggttgg gaaaccctat tctagagcca acaggctgtg aagcttgact catggttcca | 240 |
| tcaccaaatag ctgcgtgacc ttggtgagtt ccttagctgc tctgtgcctc ggattcatgg | 300 |
| taggttttcc ttgttaggtt taaatgagtg aagttataca gagggcctga agtctcatgg | 360 |

```
tattttacta gagcctcatt gtgttttagt tataattaga aattgggtaa ggtaaggaca    420
cagaagaagc catctgatct gggggcttca cacttagaag tgacctcgga gcaattgtat    480
tggggtggaa agggactaac agccaggagc agagggcaca ttggaattgg ggccagaggg    540
cacagactgc cttgtccatc aggcatagca atggacagag aaggggaat  gactagttat    600
ggctgcaagg ccaagtacag gggacttatt tctcatatct atctatctat ctacctaccg    660
tctatttatc tatcatctat ctacttattt atctatctat ttatgcatgt gtaccaaccg    720
aaagttttag taaatgcaca aactgcgata taatgaaaat ggaaattttc aaaagaagag    780
aaatcacctg ccacctgact accttaacaa atgagtggtt ttcatctctc cttccaggcc    840
tgtcatttt  acagtgcttt agtcataaaa caggtcctct attctattgt tttatgtcac    900
atgaaattgt accataagca ttttccatga tgtgactcca ctgtttcatt ttccattttt    960
ttccagaatg aagataacct cattgttttt ttcctgattg taaaaatgct ctgtgctctt   1020
tttttttttt tttaacaatg caggcagtac caaaaagtat gaagaagaat gtaatagttc   1080
ccatttccca tctcactctt taaggccagc attttggtga acatccatcc gaacaaatct   1140
ccacgcgttt atcaatttgt tgacttactc cttcttttat gtaaatatga acatgattta   1200
actgccagtc catttggaac cttaaagtga aggttttta  ttgttggggt ttgctatggt   1260
ctgaatatgt gtgtccccccc aaaatttatg ttgaatccta acgcccaatg cgattaggag   1320
gtggggccat taggaggtga ttaagtcatg aagtcatcag ccctaatgaa tgggatttgt   1380
ggccttgaaa agggacccca gagagctgcc ttgccccttc tgccatgtaa ggacacagtg   1440
aggagctagg aaggggggcct cagcagagac caaatgtgat ggtgcctcga tattggactt   1500
cccagcctcc agaatgtgag aaatgaattt ctgttgttta taagtcaccc agtctatagt   1560
attttgttct agcagcccaa acagactaag tcagggttgt tgttttagga agtggggaat   1620
ggggccatgc atgggtgtac gccagaacaa aggaagccag caagtcctga aagatactgg   1680
aaaagggaat agtgggcacg tgcagtgtgt tagtttcctg aggctgctat aacaaagcac   1740
cacaggttgg gtggcttaaa taacagaaat tcattctccc atcattctgg ggaccagacg   1800
tctgaaatca agactcctat gccatgctcc ttctgaaggc tccaggggag g            1851
```

<210> SEQ ID NO 31
<211> LENGTH: 1701
<212> TYPE: DNA
<213> ORGANISM: Homo sapiens
<220> FEATURE:
<221> NAME/KEY: misc_feature
<223> OTHER INFORMATION: sequence of STAR31
<220> FEATURE:
<221> NAME/KEY: misc_feature
<222> LOCATION: (159)..(1696)
<223> OTHER INFORMATION: n is a, c, g, or t on various positions

<400> SEQUENCE: 31

```
cacccgcctt ggccccccag agtgctggga ttacaagtgt aaaccaccat tcctggctag     60
atttaatttt ttaaaaaata aagagaagta ggaatagttc attttaggga gagcccccta    120
actgggacag gggcaggaca ggggtgaggc ttcccttant tcaagctcac ctcaaaccca    180
cccaggactg tgtgtcacat tctccaataa aggaaaggtt gctgccccg  cctgtgagtg    240
ctgcagtgga gggtagaggg ccgtgggcag agtgcttcat ggactgctca tcaagaaagg    300
cttcatgaca atcggcccag ctgctgtcat cccacattct acttccagct aggagaaggc    360
ggcttgccca cagtcaccca gccggcaagt gtcacccctg ggttggaccc agagctatga    420
```

| | |
|---|---:|
| tcctgcccag gggtccagct gagaatcagg cccacgttct aggcagaggg gctcacctac | 480 |
| tgggactcca gtagctgtag tgcatggagg catcatggct gcagcagcct ggacctggtc | 540 |
| tcacactggc tgtccctgtg ggcaggccat cctcaatgcc aggtcaggcc caagcatgta | 600 |
| tcccagacaa tgacaatggg gtggaatcct ctcttgtccc agaagccact cctcactgtt | 660 |
| ctacctgagg aaggcagggg catggtggaa tcctgaagcc tgctgtgagg gtctccagcg | 720 |
| aacttgcaca tggtcagccc tgccttctcc tccctgaact agattgagcg agagcaagaa | 780 |
| ggacattgaa ccagcaccca agaattttg gggaacggcc tctcatccag gtcaggctca | 840 |
| cctccttttt aaaatttaat taattaatta attaattttt ttttagagac agagtcttac | 900 |
| tgtgtggccc aggctgtagt gcagtggcac aatcatagtt cactgcagcc tcaaactccc | 960 |
| cacctcagcc tctggattag ctgagactac aggtgcacca ccaccacacc cagctaatat | 1020 |
| ttttattttt gtagagagag ggtttcacca tcttgcccag gctggtctca aactcctggg | 1080 |
| ctcaagtgat cccgcccagg tctgaaagcc cccaggctgg cctcagactg tggggttttc | 1140 |
| catgcagcca cccgagggcg cccccaagcc agttcatctc ggagtccagg cctggccctg | 1200 |
| ggagacagag tgaaaccagt ggttttttatg aacttaactt agagtttaaa agatttctac | 1260 |
| tcgatcactt gtcaagatgc ccctctctg gggagaaggg aacgtgactg gattccctca | 1320 |
| ctgttgtatc ttgaataaac gctgctgctt catcctgtgg gggccgtggc cctgtccctg | 1380 |
| tgtgggtggg gcctcttcca tttccctgac ttagaaacca cagtccacct agaacagggt | 1440 |
| ttgagaggct tagtcagcac tgggtagcgt tttgactcca ttctcggctt tcttctttt | 1500 |
| cttccagga ttttttgtgca gaatggttc ttttgttgcc gtgttagtcc tccttggaag | 1560 |
| gcagctcaga aggcccgtga atgtcgggg gacaggaccc ccagggaggg aaccccaggc | 1620 |
| tacgcacttt agggttcgtt ctccagggag ggcgacctga ccccgnatc cgtcggngcg | 1680 |
| cgnngnnacn aannnnttcc c | 1701 |

<210> SEQ ID NO 32
<211> LENGTH: 771
<212> TYPE: DNA
<213> ORGANISM: Homo sapiens
<220> FEATURE:
<221> NAME/KEY: misc_feature
<223> OTHER INFORMATION: sequence of STAR32

<400> SEQUENCE: 32

| | |
|---|---:|
| gatcacacag cttgtatgtg ggagctagga ttggaacccc agaagtctgg ccccaggttc | 60 |
| atgctctcac ccactgcata caatggcctc tcataaatca atccagtata aacattaga | 120 |
| atctgcttta aaaccataga attagtagcg taagtaataa atgcagagac catgcagtga | 180 |
| atggcattcc tggaaaaagc ccccagaagg aattttaaat cagctttcgt ctaatcttga | 240 |
| gcagctagtt agcaaatatg agaatacagt tgttcccaga taatgcttta tgtctgacca | 300 |
| tcttaaactg gcgctgtttt tcaaaaactt aaaaacaaaa tccatgactc ttttaattat | 360 |
| aaaagtgata catgtctact tgggaggctg aggtggtggg aggatggctt gagtttgagg | 420 |
| ctgcagtatg ctactatcat gcctataaat agccgctgca ttccagcttg gcaacatac | 480 |
| ccaggcccta tctcaaaaaa ataaaaagta atacatctac attgaagaaa attaatttta | 540 |
| ttgggttttt ttgcatttt attatacaca gcacacacag cacatatgaa aaatgggta | 600 |
| tgaactcagg cattcaactg gaagaacagt actaaatcaa tgtccatgta gtcagcgtga | 660 |

```
ctgaggttgg tttgtttttt cttttttctt ctcttctctt ctctttttctt ttttttttgag    720 acggagcttt gctcttttg cccaggcttg attgcaatgg cgtgatctca g                771
```

<210> SEQ ID NO 33
<211> LENGTH: 1368
<212> TYPE: DNA
<213> ORGANISM: Homo sapiens
<220> FEATURE:
<221> NAME/KEY: misc_feature
<223> OTHER INFORMATION: sequence of STAR33

<400> SEQUENCE: 33

```
gcttttatcc tccattcaca gctagcctgg cccccagagt acccaattct ccctaaaaaa      60
cggtcatgct gtatagatgt gtgtggcttg gtagtgctaa agtggccaca tacagagctc     120
tgacaccaaa cctcaggacc atgttcatgc cttctcactg agttctggct tgttcgtgac     180
acattatgac attatgatta tgatgacttg tgagagcctc agtcttctat agcactttta     240
gaatgcttta taaaaaccat ggggatgtca ttatattcta acctgttagc acttctgttc     300
gtattaccca tcacatccca acatcaattc tcatatatgc aggtacctct tgtcacgcgc     360
gtccatgtaa ggagaccaca aaacaggctt tgtttgagca acaaggtttt tatttcacct     420
gggtgcaggt gggctgagtc tgaaaagaga gtcagtgaag ggagacaggg gtgggtccac     480
tttataagat ttgggtaggt agtggaaaat tacaatcaaa gggggttgtt ctctggctgg     540
ccagggtggg ggtcacaagg tgctcagtgg gagagccttt gagccaggat gagccagaag     600
gaatttcaca aggtaatgtc atcagttaag gcagggactg gccatttca cttcttttgt      660 ggtggaatgt catcagttaa ggcaggaacc ggccattttc acttcttttg tgattcttca     720
cttgcttcag gccatctgga cgtataggtg caggtcacag tcacagggga taagatggca     780
atggcatagc ttgggctcag aggcctgaca cctctgagaa actaaagatt ataaaaatga     840
tggtcgcttc tattgcaaat ctgtgtttat tgtcaagagg cacttatttg tcaattaaga     900
acccagtggt agaatcgaat gtccgaatgt aaaacaaaat acaaaacctc tgtgtgtgtg     960
tgtgtgtgag tgtgtgtgta tgtgtgtgtg tgtgtattag agaggaaaag cctgtatttg    1020
gaggtgtgat tcttagattc taggttcttt cctgcccacc ccatatgcac ccaccccaca    1080
aaagaacaaa caacaaatcc caggacatct tagcgcaaca tttcagtttg catattttac    1140
atatttactt ttcttacata ttaaaaaact gaaaatttta tgaacacgct aagttagatt    1200
ttaaattaag tttgttttta cactgaaaat aatttaatat ttgtgaagaa tactaataca    1260
ttggtatatt tcattttctt aaaattctga accctcttc ccttatttcc ttttgacccg     1320
attggtgtat tggtcatgtg actcatggat ttgccttaag gcaggagg                 1368
```

<210> SEQ ID NO 34
<211> LENGTH: 755
<212> TYPE: DNA
<213> ORGANISM: Homo sapiens
<220> FEATURE:
<221> NAME/KEY: misc_feature
<223> OTHER INFORMATION: sequence of STAR34

<400> SEQUENCE: 34

```
actgggcacc ctcctaggca ggggaatgtg agaactgccg ctgctctggg gctgggcgcc      60
atgtcacagc aggagggagg acggtgttac accacgtggg aaggactcag ggtggtcagc     120
cacaaagctg ctggtgatga ccaggggctt gtgtcttcac tctgcagccc taacacccag     180
gctgggttcg ctaggctcca tcctgggggt gcagaccctg agagtgatgc cagtgggagc     240
```

-continued

```
ctcccgcccc tccccttcct cgaaggccca ggggtcaaac agtgtagact cagaggcctg      300
agggcacatg tttatttagc agacaaggtg gggctccatc agcggggtgg cctggggagc      360
agctgcatgg gtggcactgt ggggagggtc tcccagctcc ctcaatggtg ttcgggctgg      420
tgcggcagct ggcggcaccc tggacagagg tggatatgag ggtgatgggt ggggaaatgg      480
gaggcacccg agatggggac agcagaataa agacagcagc agtgctgggg gcaggggga       540 tgagcaaagg caggcccaag accccagcc cactgcaccc tggcctccca caagcccct        600 cgcagccgcc cagccacact cactgtgcac tcagccgtcg atacactggt ctgttaggga      660
gaaagtccgt cagaacaggc agctgtgtgt gtgtgtgcgt gtatgagtgt gtgtgtgtga      720
tccctgactg ccaggtcctc tgcactgccc ctggg                                 755
```

<210> SEQ ID NO 35
<211> LENGTH: 1193
<212> TYPE: DNA
<213> ORGANISM: Homo sapiens
<220> FEATURE:
<221> NAME/KEY: misc_feature
<223> OTHER INFORMATION: sequence of STAR35
<220> FEATURE:
<221> NAME/KEY: misc_feature
<222> LOCATION: (312)..(1191)
<223> OTHER INFORMATION: n is a, c, g, or t on various positions

<400> SEQUENCE: 35

```
cgacttggtg atgcgggctc ttttttggtt ccatatgaac tttaaagtag tcttttccaa      60
ttctgtgaag aaagtcattg gtaggttgat ggggatggca ttgaatctgt aaattacctt     120
gggcagtatg gccattttca caatgttgat tcttcctatc catgatgatg aatgttctt     180 ccattagttt gtatcctctt ttatttcctt gagcagtggt ttgtagttct ccttgaagag    240
gtccttcaca tcccttgtaa gttggattcc taggtatttt attctctttg aagcaaattg     300
tgaatgggag tncactcacg atttggctct ctgtttgtct gctgggtgta taaanaatgt     360
ngtgatnttn gtacattgat ttngtatccn tgagacttng ctgaatttgc ttnatcngct     420
tnngggaacc ttttgggctg aaacnatggg attttctaaa tatacaatca tgtcgtctgc    480
aaacagggaa caatttgact tcctctttttc ctaattgaat acactttatc tccttctcct    540
gcctaattgc cctgggcaaa acttccaaca ctatgntngn aataggagnt ggtgagagag     600
ggcatccctg ttcttgttgc cagnttttca aagggaatgc ttccagtttt ggcccattca     660
gtatgatatg ggctgtgggt ngtgtcataa atagctctta tnattttgaa atgtgtccca     720
tcaataccta atttattgaa agtttttagc atgaangcat ngttgaattt ggtcaaaggc     780 ttttctgca tctatggaaa taatcatgtg gttttttgtct ttggctcntg tttatatgct     840
ggatnacatt tattgatttg tgtatatnga acccagcctn ncatcccagg gatgaagccc     900
acttgatcca agcttggcgc gcngnctagc tcgaggcagg caaaagtatg caaagcatgc     960
atctcaatta gtcagcaccc atagtccgcc cctacctccg cccatccgcc cctaactcng    1020
nccgttcgcc cattctcgcc catggctgac taatnttttt annatccaag cggngccgcc    1080
ctgcttganc attcagagtn nagagnnttg gaggccnagc cttgcaaaac tccggacngn    1140
ttctnnggat tgacccccnnt taaatatttg gttttttgtn ttttcannggg nga         1193
```

<210> SEQ ID NO 36
<211> LENGTH: 1712
<212> TYPE: DNA
<213> ORGANISM: Homo sapiens
<220> FEATURE:
<221> NAME/KEY: misc_feature
<223> OTHER INFORMATION: sequence of STAR36

<400> SEQUENCE: 36

| | | |
|---|---|---|
| gatcccatcc ttagcctcat cgatacctcc tgctcacctg tcagtgcctc tggagtgtgt | 60 |
| gtctagccca ggcccatccc ctggaactca ggggactcag gactagtggg catgtacact | 120 |
| tggcctcagg ggactcagga ttagtgagcc ccacatgtac acttggcctc agtggactca | 180 |
| ggactagtga gccccacatg tacacttggc tcaggggac tcaggattag tgagccccca | 240 |
| catgtacact tggcctcagg ggactcagga ttagtgagcc ccacatgtac acttggcctc | 300 |
| agggggactca ggactagtga gccccacatg tacacttggc tcaggggac tcagaactag | 360 |
| tgagccccac atgtacactt ggcttcaggg gactcaggat tagtgagccc cacatgtaca | 420 |
| cttggacacg tgaaccacat cgatgtgctg cagagctcag ccctctgcag atgaaatgtg | 480 |
| gtcatggcat tccttcacag tggcacccct cgttccctcc ccacctcatc tcccattctt | 540 |
| gtctgtcttc agcacctgcc atgtccagcc ggcagattcc accgcagcat cttctgcagc | 600 |
| acccccgacc acacacctcc ccagcgcctg cttggccctc cagcccagct cccgcctttc | 660 |
| ttccttgggg aagctccctg gacagacacc ccctcctccc agccatggct ttttcctgct | 720 |
| ctgccccacg cgggaccctg ccctggatgt gctacaatag acacatcaga tacagtcctt | 780 |
| cctcagcagc cggcagaccc agggtggact gctcggggcc tgcctgtgag gtcacacagg | 840 |
| tgtcgttaac ttgccatctc agcaactagt gaatatgggc agatgctacc ttccttccgg | 900 |
| ttccctggtg agaggtactg gtggatgtcc tgtgttgccg gccacctttt gtccctggat | 960 |
| gccatttatt ttttccaca aatatttccc aggtctcttc tgtgtgcaag gtattagggc | 1020 |
| tgcagcgggg gccaggccac agatctctgt cctgagaaga cttggattct agtgcaggag | 1080 |
| actgaagtgt atcacaccaa tcagtgtaaa ttgttaactg ccacaaggag aaaggccagg | 1140 |
| aaggagtggg gcatggtggt gttctagtgt tacaagaaga agccagggag ggcttcctgg | 1200 |
| atgaagtggc atctgacctg gatctggag gaggagaaaa atgtcccaaa agagcagaga | 1260 |
| gcccacccta ggctctgcac caggaggcaa cttgctgggc ttatggaatt cagagggcaa | 1320 |
| gtgataagca gaaagtcctt gggggccaca attaggattt ctgtcttcta aagggcctct | 1380 |
| gccctctgct gtgtgacctt gggcaagtta cttcacctct agtgctttgg ttgcctcatc | 1440 |
| tgtaaagtgg tgaggataat gctatcacac tggttgagaa ttgaagtaat tattgctgca | 1500 |
| aagggcttat aagggtgtct aatactagta ctagtaggta cttcatgtgt cttgacaatt | 1560 |
| ttaatcatta ttattttgtc atcaccgtca ctcttccagg ggactaatgt ccctgctgtt | 1620 |
| ctgtccaaat taaacattgt ttatccctgt gggcatctgg cgaggtggct aggaaagcct | 1680 |
| ggagctgttt cctgttgacg tgccagacta gt | 1712 |

<210> SEQ ID NO 37
<211> LENGTH: 1321
<212> TYPE: DNA
<213> ORGANISM: Homo sapiens
<220> FEATURE:
<221> NAME/KEY: misc_feature
<223> OTHER INFORMATION: sequence of STAR37

<400> SEQUENCE: 37

| | | |
|---|---|---|
| aggatcacat ttaaggaagt gtgtggggtc cctggatgac accagcaccc agtgcggctc | 60 |
| tgtctggcaa ccgctcccaa ggtggcagga gtgggtgtcc cctgtgtgtc agtgggcagc | 120 |

```
tcctgctgag cctacagctc actggggagc ctgacagcgg ggccatgtgc ctgacactcc       180
tctctgcttg tggacctggc aaggcaggga gcagaaaaca gagccacttg aaggctttct       240
gtctgcgtct gtgtgcagtg tggatttagt tgtgcttttt tcttgctggg agagcacagc       300
caccatttac aagcagtgtc accctcatgg gtggcgagga cagaacagga gcctctgctc       360
tctgtaccta tctgggcccg gtgggctccc ttgtcctggc ttccatctct gtctcagcga       420
ccattcagcc ctgcgcagga acacatgttg cttagaaaag ccaaattcag cccttgtctc       480
tgcctcctct ggtctcatga tgtgcatctg ttaccttgaa actggaaacc agtctatcaa       540
tgtctgtgcc aattttttat tccctcccca acctccttcc ccatacgact ttttatttat       600
gtaggatgtg tgctgtctaa tgatgggatg accacatttt tccatgttct aaaagtgctc       660
ctctcccgca gggtcccagg gctggtggtt gctttgggtc tacagctacg tcttacccgc       720
ctcctgcctc aacagcctgt gtggtggcaa agccggtgtg gggctgggga acgcagcgtt       780
ctccaggagg gggacccggc tctccttctg cagtgcaggc gaaggcctag atgccagtgt       840
gacctcccac aaggcgtggc ttccagactc cccggctgga agtgatgctt ttttgcctcc       900
ggccctgggt ttgaagcagc ctggctttct cttggtaagt ggctggtgtc ttagcagctg       960
caatctgagc tcagccacct acacaccacc gtggccgaca ctttcattaa aaagttttcct      1020 gagacgactt gcgtgcatgt tgacttcatg atcagcgccg ctgggaagaa cccctgagcc      1080
ggtggggtgg ggctggaagc agcaggtgca gtgatggggc tgggtgccca ggaggcctca      1140
gtgctcaatc aggccaaggt ggccaagccc aggctgcagg gaaggccggc ctggggggttg     1200 tgggtgagca caggcaggca ccagctgggc agtgttagga tgctggagca gcatccgtaa      1260
ccccactgag tggggtagtc tggttggggc agggaccgct gttgctttgg cagagagaga     1320
t                                                                      1321

<210> SEQ ID NO 38
<211> LENGTH: 1445
<212> TYPE: DNA
<213> ORGANISM: Homo sapiens
<220> FEATURE:
<221> NAME/KEY: misc_feature
<223> OTHER INFORMATION: sequence of STAR38
<220> FEATURE:
<221> NAME/KEY: misc_feature
<222> LOCATION: (348)..(949)
<223> OTHER INFORMATION: n is a, c, g, or t on various positions

<400> SEQUENCE: 38
gatctatggg agtagcttcc ttagtgagct ttcccttcaa atactttgca accaggtaga        60
gaattttgga gtgaaggttt tgttcttcgt ttcttcacaa tatggatatg catcttcttt      120
tgaaaatgtt aaagtaaatt acctctcttt tcagatactg tcttcatgcg aacttggtat      180 cctgttttcca tcccagcctt ctataaccca gtaacatctt ttttgaaacc agtgggtgag     240
aaagacacct ggtcaggaac gcggaccaca ggacaactca ggctcaccca cggcatcaga      300
ctaaaggcaa acaaggactc tgtataaagt accggtggca tgtgtatnag tggagatgca      360
gcctgtgctc tgcagacagg gagtcacaca gacactttc tataatttct taagtgctttt     420 gaatgttcaa gtagaaagtc taacattaaa tttgattgaa caattgtata ttcatggaat      480
attttggaac ggaataccaa aaaatggcaa tagtggttct ttctggatgg aagacaaact      540
tttcttgttt aaaataaatt ttattttata tatttgaggt tgaccacatg accttaagga      600
tacatataga cagtaaactg gttactacag tgaagcaaat taacatatct accatcgtac      660
```

```
atagttacat ttttttgtgt gacaggaaca gctaaaatct acgtatttaa caaaaatcct    720
aaagacaata catttttatt aactatagcc ctcatgatgt acattagatc gtgtggttgt    780
ttcttccgtc cccgccacgc cttcctcctg ggatggggat tcattcccta gcaggtgtcg    840
gagaactggc gcccttgcag ggtaggtgcc ccggagcctg aggcgggnac tttaanatca    900
gacgcttggg ggccggctgg gaaaaactgg cggaaaatat tataactgna ctctcaatgc    960
cagctgttgt agaagctcct gggacaagcc gtggaagtcc cctcaggagg cttccgcgat   1020
gtcctaggtg gctgctccgc ccgccacggt catttccatt gactcacacg cgccgcctgg   1080
aggaggaggc tgcgctggac acgccggtgg cgcctttgcc tggggagcg cagcctggag    1140 ctctggcggc agcgctggga gcggggcctc ggaggctggg cctggggacc caaggttggg   1200
cggggcgcag gaggtgggct cagggttctc cagagaatcc ccatgagctg acccgcaggg   1260
cggccgggcc agtaggcacc gggcccccgc ggtgacctgc ggacccgaag ctggagcagc   1320
cactgcaaat gctgcgctga ccccaaatgc tgtgtccttt aaatgtttta attaagaata   1380
attaataggt ccgggtgtgg aggctcaagc cttaatcccc agcacctggc gaggccgagg   1440
aggga                                                              1445
```

<210> SEQ ID NO 39
<211> LENGTH: 2331
<212> TYPE: DNA
<213> ORGANISM: Homo sapiens
<220> FEATURE:
<221> NAME/KEY: misc_feature
<223> OTHER INFORMATION: sequence of STAR39

<400> SEQUENCE: 39

```
gtgaaataga tcactaaagc tgattcctct tgtctaaatg aaactttcta ccctttgatg     60
gacagctatg ctttccccat cctctcccgt cccccagccc ttggtaacca tcatcctact    120
ctctacttgt aggagttcaa cttgtttaga ttttgtgagt gagaacatgt ggtatttgcc    180
tttagagtcc tctaggttta tccatattgt gttaaatgac aggattccct gccttttaa    240 ggctgaatag tatttcattg taatatatat acatacacac acacatatac acacacatat    300
atatacatat atacatatat gtacatagat acatatatat gtacatatat acacacacat    360
atacacacat atacacacat atacacatat acatatatac acatatatgt acatatatat    420 aactttttt catttatcca ttcacttaat acatatgatg gagggcttta tatgtgccag    480
gctctgtgat gaatgctgga aattcaatag tgagaaagac tcagtctctg cctccaaaga    540
gcatcatggg ctaggtgctg caacgaggaa ttgccaactg ttgtcatgag agcacagaga    600
agggactcaa ccagccttga agaatcaggg gaggcttcta agctaatggt gtgtgcctgg    660
ggatcacatt gtttcaagca gcagtaacag gatgtgctca ggtccagatg tgagagagag    720
agagagcata tgtcttcaag aaactaacag tagctcccta tagctgaagc aggagtacaa    780
aatagtgagt ttaagtgatg aggcaagaga tatgaagaag cttgaccatg cagctacacc    840
gggcagcatg ccctctgaga catctcatgg aagccggaaa tgggagtgcc ttgataccaa    900
gccagagaaa ttataatact aagtagatag actgagcagc actcctcctg ggaagaatga    960
gacaagccct gaatttggag gtaagttgtg gattggtgat tagaggagag gtaacaggca   1020
ccaaagcaag aaatagtatt gatgcaaagc tgaggttaat tggatgacaa aatgaagagc   1080 ataagggget cagacacaga ctgagcagaa acgagtagc atctgaacct agattgagtt    1140
actaatggat gagaaagagt tcttaaagtt gatgaccacg ggatccatat ataagaatgt   1200
```

```
ccaatctccc caaattgatc cacgagttca gtgcaatgcc aatcaaaatc ccactaacaa    1260
gtttatttta aaatgtaaat gaaaatacaa aattttttaaa aagcaaagca atattgaaaa   1320
cccaggaaaa attaggagga cttacacaac ctgatctcaa aacttaccat tatcaagaca   1380
gagtgttatt gacacaagga gagacaaata gataaacgga atgtggtagt ctggagatgc   1440
acccacatgt atgtggtcaa ttgattttttg gccaaggcac caagtcaatt caaaggagca   1500
aggaaagtag tacagaaaca accaaatatt gttttggaaa ataatgacaa agggcttata   1560
accagaatat aagcatataa atataattct ttcaaatcaa taataagaag gcaaatatct   1620
aataaaaatg agcaaagact tgaaaagtca cttaaaaagg cttattaatt agaaatatgc   1680
aaatgttatt agtcttcagt ggaatttaca ttaaaccaca agggatacta ttatatctta   1740
tgcccactag aataaccaaa ggaaaaaaga cagacaaaac aaaatgctgg tgaggatgtg   1800
aagcaactgg aactctcata cattattggt ggtaatgtaa aatttataca accattatga   1860
ataaaggttt ggcagtttct tacaaagttg aatgcacttc tccacgatga ctaggctttt   1920
cactcatagg cgtctggctc cctagaactg aaaacatatg ttcacaagaa gacttgcaaa   1980
tatatattct cccacgtcag gagatatttg ctatgcattt aactgacata agattagtgc   2040
tagagtttat aatgaggttc ttcaaatcta aagaaaatg caaagcatat aatagtaagg   2100
ggtgcaggcc aggcgcagtg gctcactctg taatcccagc actttgggag gccgaggtgg   2160
gcggatcaca aggtcaggag ttcgagacca acctggccaa catagtgaaa ccctgtctct   2220
actaaaaata caaaaactag ccaggtgcgg tgtcatgcac ctgtagtccc agctactcgg   2280
gaggccgagg caggagaatc acttgaacct gggaggtgga ggttgcagtg a           2331
```

<210> SEQ ID NO 40
<211> LENGTH: 1071
<212> TYPE: DNA
<213> ORGANISM: Homo sapiens
<220> FEATURE:
<221> NAME/KEY: misc_feature
<223> OTHER INFORMATION: sequence of STAR40

<400> SEQUENCE: 40

```
gctgtgattc aaactgtcag cgagataagg cagcagatca agaaagcact ccgggctcca     60
gaaggagcct tccaggccag ctttgagcat aagctgctga tgagcagtga gtgtcttgag    120
tagtgttcag ggcagcatgt taccattcat gcttgacttc tagccagtgt gacgagaggc    180
tggagtcagt tctctagaga gttgagcagc tccagcctta gatctcccag tcttatgcgg    240
tgtgcccatt cgctttgtgt ctgcagtccc ctggccacac ccagtaacag ttctgggatc    300
tatgggagta gcttccttag tgagcttttcc cttcaaatac tttgcaacca ggtagagaat    360
tttggagtga aggttttgtt cttcgtttct tcacaatatg gatatgcatc ttcttttgaa    420
aatgttaaag taaattacct ctcttttcag atactgtctt catgcgaact tggtatcctg    480
tttccatccc agccttctat aacccagtaa catcttttttt gaaaccagtg ggtgagaaag    540
acacctggtc aggaacgcgg accacaggac aactcaggct cacccacggc atcagactaa    600
aggcaaacaa ggactctgta taaagtaccg gtggcatgtg tattagtgga gatgcagcct    660
gtgctctgca gacagggagt cacacagaca cttttctata atttcttaag tgctttgaat    720
gttcaagtag aaagtctaac attaaatttg attgaacaat tgtatattca tggaatatttt    780 tggaacggaa taccaaaaaa tggcaatagt ggttctttct ggatggaaga caaacttttc    840
ttgtttaaaa taaattttat tttatatatt tgaggttgac cacatgacct taaggataca    900
```

| | |
|---|---|
| tatagacagt aaactggtta ctacagtgaa gcaaattaac atatctacca tcgtacatag | 960 |
| ttacatttt ttgtgtgaca ggaacagcta aaatctacgt atttaacaaa aatcctaaag | 1020 |
| acaatacatt tttattaact atagccctca tgatgtacat tagatctcta a | 1071 |

<210> SEQ ID NO 41
<211> LENGTH: 1135
<212> TYPE: DNA
<213> ORGANISM: Homo sapiens
<220> FEATURE:
<221> NAME/KEY: misc_feature
<223> OTHER INFORMATION: sequence of STAR41

<400> SEQUENCE: 41

| | |
|---|---|
| cgtgtgcagt ccacggagag tgtgttctcc tcatcctcgt tccggtggtt gtggcgggaa | 60 |
| acgtggcgct gcaggacacc aacatcagtc acgtatttca ttctggaaaa aaaagtagca | 120 |
| caagcctcgg ctggttccct ccagctctta ccaggcagcc taagcctagg ctccattccc | 180 |
| gctcaaggcc ttcctcaggg gcctgctcac cacaggagct gttcccatgc agggactaag | 240 |
| gacatgcagc ctgcatagaa accaagcacc caggaaaaca tgattggatg gagcggggggg | 300 |
| gtgtggtctc tagccttgtc cacctccggt cctcatgggt ctcacacctc ctgagaatgg | 360 |
| gcaccgcaga ggccacagcc catacagcca agatgacaga ctccgtaagt gacagggatc | 420 |
| cacagcagag tgggtgaaat gttccctata aactttacaa aattaatgag ggcaggggga | 480 |
| ggggagaaat gaaatgaac ccagctcgca gcacatcagc atcagtcact aggtcggcgt | 540 |
| gctctctgac tgcttcctcg tagctgcttg gtgtctcatt gcctcagaag catgtagacc | 600 |
| ctgtcacaag attgtagttc ccctaactgc tccgtagatc acaacttgaa ccttaggaaa | 660 |
| tgctgttttc cctttgagat attcctttgg gtcctgtata ctgatggagc tactgactga | 720 |
| gctgctccga aggaccccac gaggagctga ctaaaccaag agtgcagttt gtacaccctg | 780 |
| atgattacat ccccccttgcc ccaccaatca actctcccaa ttttccagcc cctcacccctc | 840 |
| cagtccccctt aaaagcccca gcccaggccg ggcacagtgg ctcatgcctg taatcccagc | 900 |
| actttgggag gccaaggtgg gcagatcacc tgagggcagg aatttgagac cagcctgacc | 960 |
| aacatgaaga acccccgtct ctattacaaa tacaaaatta gccgggcgtg ttgctgcata | 1020 |
| ctggtaatcc cagctacttg ggagggtgag gcaggagaat cacttgaatc tgggaggcgg | 1080 |
| aggttgcgat gagccgagac agcgccattg cactgcagcc tgggcaacaa gagca | 1135 |

<210> SEQ ID NO 42
<211> LENGTH: 735
<212> TYPE: DNA
<213> ORGANISM: Homo sapiens
<220> FEATURE:
<221> NAME/KEY: misc_feature
<223> OTHER INFORMATION: sequence of STAR42

<400> SEQUENCE: 42

| | |
|---|---|
| aagggtgaga tcactaggga gggaggaagg agctataaaa gaaagaggtc actcatcaca | 60 |
| tcttacacac tttttaaaac cttggttttt taatgtccgt gttcctcatt agcagtaagc | 120 |
| cctgtggaag caggagtctt tctcattgac caccatgaca agaccctatt tatgaaacat | 180 |
| aatagacaca caaatgttta tcggatattt attgaaatat aggaatttt cccctcacac | 240 |
| ctcatgacca cattctggta cattgtatga atgaatatac cataattta cctatggctg | 300 |
| tatatttagg tcttttcgtg caggctataa aaatatgtat gggccggtca cagtgactta | 360 |

| | |
|---|---|
| cgcccgtagt cccagaactt tgggaggccg aggcgggtgg atcacctgag gtcgggagtt | 420 |
| caaaaccagc ctgaccaaca tggagaaacc ccgtctctgc taaaaataca aaaattaact | 480 |
| ggacacggtg gcgtatgcct gtaatcccag ctactcggga agctgaggca ggagaactgc | 540 |
| ttgaacccag gaggcggagg ttgtggtgag tcgagattgc gccattgcac tccagcctgg | 600 |
| gcaacaagag cgaaattcca tctcaaaaaa aagaaaaaag tatgactgta tttagagtag | 660 |
| tatgtggatt tgaaaaatta ataagtgttg ccaacttacc ttagggttta taccatttat | 720 |
| gagggtgtcg gtttc | 735 |

<210> SEQ ID NO 43
<211> LENGTH: 1227
<212> TYPE: DNA
<213> ORGANISM: Homo sapiens
<220> FEATURE:
<221> NAME/KEY: misc_feature
<223> OTHER INFORMATION: sequence of STAR43

<400> SEQUENCE: 43

| | |
|---|---|
| caaatagatc tacacaaaac aagataatgt ctgcccattt ttccaaagat aatgtggtga | 60 |
| agtgggtaga gagaaatgca tccattctcc ccacccaacc tctgctaaat tgtccatgtc | 120 |
| acagtactga gaccaggggg cttattccca gcgggcagaa tgtgcaccaa gcacctcttg | 180 |
| tctcaatttg cagtctaggc cctgctattt gatggtgtga aggcttgcac ctggcatgga | 240 |
| aggtccgttt tgtacttctt gctttagcag ttcaaagagc agggagagct gcgagggcct | 300 |
| ctgcagcttc agatggatgt ggtcagcttg ttggaggcgc cttctgtggt ccattatctc | 360 |
| cagcccccct gcggtgttgc tgtttgcttg gcttgtctgg ctctccatgc cttgttggct | 420 |
| ccaaaatgtc atcatgctgc accccaggaa gaatgtgcag gcccatctct tttatgtgct | 480 |
| ttgggctatt ttgattcccc gttgggtata ttccctaggt aagacccaga agacacagga | 540 |
| ggtagttgct ttgggagagt ttggacctat gggtatgagg taatagacac agtatcttct | 600 |
| cttcatttg gtgagactgt tagctctggc cgcggactga attccacaca gctcacttgg | 660 |
| gaaaacttta ttccaaaaca tagtcacatt gaacattgtg gagaatgagg gacagagaag | 720 |
| aggccctaga tttgtacatc tgggtgttat gtctataaat agaatgcttt ggtggtcaac | 780 |
| tagacttgtt catgttgaca tttagtcttg ccttttcggt ggtgatttaa aaattatgta | 840 |
| tatcttgttt ggaatatagt ggagctatgg tgtggcattt tcatctggct ttttgtttag | 900 |
| ctcagcccgt cctgttatgg gcagccttga agctcagtag ctaatgaaga ggtatcctca | 960 |
| ctccctccag agagcggtcc cctcacggct cattgagagt ttgtcagcac cttgaaatga | 1020 |
| gtttaaactt gtttattttt aaaacattct tggttatgaa tgtgcctata ttgaattact | 1080 |
| gaacaacctt atggttgtga agaattgatt tggtgctaag gtgtataaat ttcaggacca | 1140 |
| gtgtctctga agagttcatt tagcatgaag tcagcctgtg gcaggttggg tggagccagg | 1200 |
| gaacaatgga gaagctttca tgggtgg | 1227 |

<210> SEQ ID NO 44
<211> LENGTH: 1586
<212> TYPE: DNA
<213> ORGANISM: Homo sapiens
<220> FEATURE:
<221> NAME/KEY: misc_feature
<223> OTHER INFORMATION: sequence of STAR44

<400> SEQUENCE: 44

```
cacctgcctc agcctcccaa agtgctgaga ttcaaagaaa ttttcatgga gaggggacag      60
atggagtcaa ttcttgtggg gtgaacatga gtaccacagt tagactgagg ttgggaaaga     120
ttttccagac aattggaaga gcatgtgaaa gacacagatt ttgagaaatg ttaagtctag     180
ggaactgcaa ggcttttggc acaagaaagc cactgtagac tatagaggca ggatgcctag     240
attcaaatcc caactgctac acttctaagc tttgtaattt tggcaagttt ttaccctcta     300
ttttcttatc tataaaatat agattttata tatatagata tagatatata gatagataat     360
aattgtgcat gcctaataaa gttgtcaaag attaaatgtt atatgtgaag tattttgtac     420
ggtgatagga acccaggaag ggctctatga atattatgta ttattattat tctaaagtag     480
ctggaataca atgttcaaag gagatagtgg caggagataa gtttgaattg aaagattgag     540
gccagaacat aaagtgcctc ctatattata ttttacataa ttggaacatc attgaaaaat     600
ttaagtatta tttatgtgtg tatgtgtgtt ttatataatt aattctagtt catcatttta     660
aaatatcttt ctgatgtcac tgtgaacaac agatgagaag aagtgaatcc tgagttaagg     720
agaccagctc tctgattact gccataatcc agggagggta ccataaggat ttcaactgga     780
agtgaatcca tcatgatgga gaggaaggac agggctgaaa atacttagg aagtagtatc     840
agtaggactg gttaagagag agcagaggca ggctacaggg gttggaggtg tcaatcacag     900
agatagggaa aatgggagga gaagcaggct ttgaaaaagt ggcttgtctt gtaaaattat     960
gtgctgttaa aacagtacaa gaaattaata tattcaatcc caaaatacag ggacaattct    1020
ttttgaaaga gttacccaga tagtcttcct tgaagttttc agttaaagaa atttcttgtt    1080
aacaaataat gtagtcatag aagaaaacac ttaaaacttt attgaataaa gctaataaat    1140
catttaatat aatttatagg aaattgttac ataacacaca cattcaatac tttttgctaa    1200
agtataaatt aatggaagga gagcacgcac acagaggttg aattatgttt atgactttat    1260
tagtcaagaa tacaaaattg agtagctaca tcaagcagaa gcacatgctt tacaatccag    1320
cacagaatcc cttgacatcc aaactcccga aacagacatg taaatacaga tgacattgtc    1380
agaacaaaat agggtctcac ccgacctata atgttctttt cttgatataa atatgcacat    1440
gaattgcata cggtcatatg gttccaatta ccattatttc ctctgggctt agctatccat    1500
ctaaggggaa tttacaccaa cactgtactt ctacttgcaa gaatatatga aagcatagtt    1560
aacttctggc ttaggacccc aactca                                         1586
```

<210> SEQ ID NO 45
<211> LENGTH: 1981
<212> TYPE: DNA
<213> ORGANISM: Homo sapiens
<220> FEATURE:
<221> NAME/KEY: misc_feature
<223> OTHER INFORMATION: sequence of STAR45

<400> SEQUENCE: 45

```
atggatcata gggtaaataa atttataatt tcttgagaaa gcttcgtact gttttccaag      60
atggctgtac taatttccat tcctaccaac agtgtacagg gtttcttttt ctccacatcc     120
tcaccaacac ttatcttcca tctttttta taatagccct agtaaaatgt gtgaggtgat     180
atctcattgt ggcattgatt tgcacttctc tgataattag gaatgtttat gatttttca     240
tgtacctggt tggccttttg tatgatgtag gaaatgtcta ttctgattct ttgcttattt     300
tttaataagc atagtttttt tcttattttt gagtaggttg agttgcttat atattattat     360
```

```
atgagcccct tacctgatgt atggtttaaa aatattatcc catttgtggg ttctcttaat    420
tctatcattg cttcttttcc tgtggaaaag ttttaagttt tatgcagtct catttgtgtg    480
ttttgctttt gttgcctttt ggaataatct acagaaaatc atagctcagg ccaatgtcat    540
acagtctcct tctatatttc cttgtagtag ttttacattt aaactttaat tttgatttga    600
tgcttgtata aagagcaaaa taaaagtcaa attttattct tctgtatgtg gatagtcagt    660
tttgtctaca ccatttattg aaaataattt tctttcttca ctgtgtattt ttagttattt    720
tatcaaaaaa tcaattgacc acagacacac ggatttattt acaggttcta tatccctttg    780
tactgtttta catgtctgtt tttatgccat tgctatgctg ttttaattcc tatagctttg    840
taatagagtt tggagtcagg tagtctgatg cctccagctt tgttcttttt gttcaagatt    900
gctttggttg gtccaggtct tttgtggttc catacaaatt ttagcagtaa tttttctatt    960
tctgtgaaga atgacattgg aatttgatag tggttgcatt taatctgtag attgctttgg   1020
gtagcattga cacttttaca atactaattt ttgaatccat caatgaagga tgtttctcca   1080
tttatttatg ccattttaat tttttttcatc aatgtgctat agttttcagt atgtaaatct   1140
tttatggttt tgattaaatt tactcctgtc ttttatatat ttatatatct gttttgattc   1200
tattataaat tgaattgcct ttatttttca ggtaatagtt tgtcattagt taatagaaac   1260
aataatgata tttgtatgtt gattttgtaa ctattaactt tattgaattt cttcatcagc   1320
tataaccatt tattttggtg gaatctttaa gattttctct atcttaagat tatattttca   1380
aaaaacagaa acaatcttac ctcttccttc cctatgtgga tttcttttac gtctttgtct   1440
tgtgtaactg ttctggctag gcaattacac ataatgtttt catcatttat aatttacat    1500
cacatccatc tattgtggca cattgattgc tacttttcaa gttgtaaacc tggacattta   1560
tcactactct tcctccaata caggagtcca tggcgtggtg tgggccctac tgtgccacag   1620
tccagggcac ggctgggctg aggttctctt gtgcaagagt ccgtggctct gcggagcaag   1680
agttctccag tgccttagtc cagggttagg caggggtggg gctccttcag tagcttagtc   1740
cagtgcgccg ccctgcgagg gtcctcctga gcaggagtac acgatgaggc agggtcctac   1800
tgtgccttag cccaggaagc gggggggctgg gtcctctggt gccatagtcc aggctgccgg   1860
gagctgggtc ctctggtgcc atagctcagg ccggcgggag ctgggtcctc tggtgccgta   1920
gtccagggtg cagcagaaca ggagtcctgc ggagcagtag tccagggcac gctggggcgt   1980
g                                                                   1981
```

<210> SEQ ID NO 46
<211> LENGTH: 1859
<212> TYPE: DNA
<213> ORGANISM: Homo sapiens
<220> FEATURE:
<221> NAME/KEY: misc_feature
<223> OTHER INFORMATION: sequence of STAR46

<400> SEQUENCE: 46

```
attgtttttc tcgcccttct gcattttctg caaattctgt tgaatcattg cagttactta     60
ggtttgcttc gtctccccca ttacaaacta cttactgggt ttttcaaccc tagttccctc    120
attttatga tttatgctca tttctttgta cacttcgtct tgctccatct cccaactcat    180
ggcccctggc tttggattat tgttttggtc ttttattttt tgtcttcttc tacctcaaca    240
cttatcttcc tctcccagtc tccggtaccc tatcaccaag ttgtcatta accttttcata   300
ttattcctca ttatccatgt attcatttgc aaataagcgt atattaacaa aatcacaggt    360
```

```
ttatggagat ataattcaca taccttaaaa ttcaggctttt taaagtgtac ctttcatgtg    420
gtttttggta tattcacaaa gttatgcatt gatcaccacc atctgattcc ataacatgtt    480
caatacctca aaaagaagtc tgtactcatt agtagtcatt tcacattcac cactccctct    540
ggctctgggc agtcactgat ctttgtgtct ctatggattt gcctagtcta ggtattttta    600
tgtaaatggc atcatacaac atgtgacctt tgtttggct tttttcattt agcaaaatgt     660
tatcaaggtc tgtccctgtt gtagcatgta ttagcacttc atttcttata tgctgaatga    720
tatactttat ttgtccatca gttgttcatg ctttatttgt ccatcagttg atgaacattt    780 gcgttttgc cactttgggc tattaagaat aatgctactg tgaacaagtg tgtacaagtt     840
cctctacaaa tttttgtgtg gacatatcct ttcagttctc tcaggtgtat atctgggaat    900
tgaattgctg ggtcgtgtag tagctatgtt aaacactttg agaaactgct ataatgttct    960
ccagagctgt accattttaa attctgtgta tgaggattcc acgttctcca cttcctcacc   1020
agtgtatgga tttgggggta acttttttaa aaagtgggat taggctgggc acagtggctc   1080
acacctgtaa tcccaacact tcaggaagct gaggtgggag gatcacttga gcctagtagt   1140
ttgagaccag cctgggcaac ataggagac  cctgtctcta caaaaaataa tttaaaataa   1200
attagctggg cgttgtggca cacacctgta gtcccagcta catgggaggc tgaggtggaa   1260
ggattccctg agcccagaag tttgaggttg cagtgagcca tgatggcagc actatactgt   1320
agcctgggtg tcagagcaag actccgtttc agggaagaaa aaaaaagtg  ggatgatatt   1380 tttgacactt tcttcttgt ttcttaatt tcatacttct ggaaattcca ttaaattagc    1440
tggtaccact ctaactcatt gtgtttcatg gctgcatagt aatattgcat aatataaata   1500
taccattcat tcatcaaagt tagcagatat tgactgttag gtgccaggca ctgctctaag   1560
cgttaaagaa aaacacacaa aaacttttgc attcttagag tttattttcc aatggagggg   1620
gtggagggag gtaagaattt aggaaataaa ttaattacat atatagcata gggtttcacc   1680
agtgagtgca gcttgaatcg ttggcagctt tcttagtagt ataaatacag tactaaagat   1740
gaaattactc taaatggtgt tacttaaatt actggaatag gtattactat tagtcacttt   1800
gcaggtgaaa gtggaaacac catcgtaaaa tgtaaaatag gaaacagctg ttaatgtt    1859
```

<210> SEQ ID NO 47
<211> LENGTH: 1082
<212> TYPE: DNA
<213> ORGANISM: Homo sapiens
<220> FEATURE:
<221> NAME/KEY: misc_feature
<223> OTHER INFORMATION: sequence of STAR47

<400> SEQUENCE: 47

```
atcattagtc attagggaaa tgcaaatgaa aaacacaagc agccaccaat atacacctac     60
taggatgatt taaaggaaaa taagtgtgaa gaaggacgta aagaaattgt aaccctgata    120
cattgatggt agaaatggat aaagttgcag ccactgtgaa aaacagtctg cagtggctca    180
gaaggttaaa tatagaaccc ctgttggacc caggaactct actcttaggc accccaaaga    240
atagagaaca gaaatcaaac agatgttgt  atactaatgt ttgtagcatc acttttcaca    300
ggagccaaaa ggtggaaata atccaaccat cagtgaacaa atgaatgtaa taaaagcaag    360
gtggtctgca tgcaatgcta catcatccat ctgtaaaaaa cgaacatcat tttgatagat    420 gatacaaacat gggtggacat tgagaacatt atgcttagtg aaataagcca gacacaaaag    480
gaatatattg tataattgta attacatgaa gtgcctagaa tagtcaaatt catacaagag    540
```

```
aaagtgggat aggaatcacc atgggctgga aataggggga aggtgctata ctgcttattg      600
tggacaaggt ttcgtaagaa atcatcaaaa ttgtgggtgt agatagtggt gttggttatg      660
caaccctgtg aatatattga atgccatgga gtgcacactt tggttaaaag gttcaaatga      720
taaatattgt gttatatata tttccccacg atagaaaaca cgcacagcca agcccacatg      780
ccagtcttgt tagctgcctt cctttacctt caagagtggg ctgaagcttg tccaatcttt      840
caaggttgct gaagactgta tgatggaagt catctgcatt gggaagaaa ttaatggaga       900 gaggagaaaa cttgagaatc cacactactc accctgcagg gccaagaact ctgtctccca      960
tgctttgctg tcctgtctca gtatttcctg tgaccacctc cttttcaac tgaagactttg     1020 gtacctgaag gggttcccag ttttttcacc tcggcccttg tcaggactga tcctctcaac     1080
ta                                                                    1082
```

<210> SEQ ID NO 48
<211> LENGTH: 1242
<212> TYPE: DNA
<213> ORGANISM: Homo sapiens
<220> FEATURE:
<221> NAME/KEY: misc_feature
<223> OTHER INFORMATION: sequence of STAR48

<400> SEQUENCE: 48

```
atcatgtatt tgttttctga attaattctt agatacatta atgttttatg ttaccatgaa       60
tgtgatatta taatataata tttttaattg gttgctactg tttataagaa tttcattttc      120
tgtttacttt gccttcatat ctgaaaacct tgctgatttg attagtgcat ccacaaattt      180
tcttggattt tctatgggta attacaaatc tccacacaat gaggttgcag tgagccaaga      240
tcacaccact gtactccagc ctgggcgaca gagtgagaca ccatctcaca aaacacata      300 aacaaacaaa cagaaactcc acacaatgac aacgtatgtg ctttcttttt ttcttcctct      360
ttctataata tttctttgtc ctatcttaac tgaactggcc agaaacccca ggacaatgat      420
aaatacgagc agtgtcaaca gacatctcat tcccttttcct agcttttata aaataacga     480 ttatgcttca acattacata tggtggtgtc gatggttttg ttatagataa gcttatcagg      540
ttaagaaatt tgtctgcgtt tcctagtttg gtataaagat tttaatataa atgaatgttg      600 tatttatca tcttatttt ttcctacatc tgctaaggta atcctgtgtt ttcccccttt        660
caatctccta atgtggtgaa tgacattaaa ataccttcta ttgttaaaat attcttgcaa      720
cgctgtatag aaccaatgcc tttattctgt attgctgatg gattttttgaa aaatatgtag    780 gtggacttag ttttctaagg ggaatagaat ttctaatata tttaaaatat tttgcatgta      840
tgttctgaag acattggtg tgtcatttct ataccatctg gctactagag gagccgactg       900
aaagtcacac tgccggagga ggggagaggt gctcttccgt ttctggtgtc tgtagccatc      960
tccagtggta gctgcagtga taataatgct gcagtgccga cagttctgga aggagcaaca     1020
acagtgattt cagcagcagc agtattgcgg gatcccacg atggagcaag ggaaataatt     1080
ctggaagcaa tgacaatatc agctgtggct atagcagctg agatgtgagt tctcacggtg    1140
gcagcttcaa ggacagtagt gatggtccaa tggcgcccag acctagaaat gcacatttcc    1200
tcagcaccgg ctccagatgc tgagcttgga cagctgacgc ct                        1242
```

<210> SEQ ID NO 49
<211> LENGTH: 1015
<212> TYPE: DNA
<213> ORGANISM: Homo sapiens

```
<220> FEATURE:
<221> NAME/KEY: misc_feature
<223> OTHER INFORMATION: sequence of STAR49

<400> SEQUENCE: 49
aaaccagaaa cccaaaacaa tgggagtgac atgctaaaac cagaaaccca aaacaatggg     60
agggtcctgc taaaccagaa acccaaaaca tgggagtga agtgctaaaa ccagaaaccc    120
aaaacaatgg gagtgtcctg ctacaccaga acccaaaac gatgggagtg acgtgataaa    180
accagacacc caaaacaatg ggagtgacgt gctaaaccag aaacccaaaa caatgggagt    240
gacgtgctaa aacctggaaa cctaaaacaa tgcgagtgag gtgctaacac cagaatccat    300
aacaatgtga gtgacgtgct aaaccagaac ccaaaacaat gggagtgacg tgctaaaaca    360
ggaacccaaa acaatgagag tgacgtgcta accagaaacc ccaaaacaat gggaatgacg    420
tgctaaaacc ggaacccaaa acaatgggag tgatgtgcta accagaaac ccaaaacaat    480 gggaatgaca tgctaaaact ggaacccaaa acaatggtaa ctaagagtga tgctaaggcc    540
ctacattttg gtcacactct caactaagtg agaacttgac tgaaaaggag attttttttt    600
tctaagacag agttttggtc tgtcccccag agtggagtgc agtggcatga tctcggctca    660
ctgcaagctc tgcctcccgg gttcaggcca ttctcctgcc tcagcctcct gagtagctgg    720
gaatacaggc acccgccacc acacttggct aatttttttgt attttttagta gagatggggt    780 ttcaccatat tagcaaggat ggtctcaatc tcctgacctc gtgatctgcc cacctcaggc    840
tcccaaagtg ctgggattac aggtgtgagc caccaccc agcaaaaagg aggaatttt    900 aaagcaaaat tatgggaggc cattgttttg aactaagctc atgcaatagg tcccaacaga    960
ccaaaccaaa ccaaaccaaa atggagtcac tcatgctaaa tgtagcataa tcaaa         1015

<210> SEQ ID NO 50
<211> LENGTH: 2355
<212> TYPE: DNA
<213> ORGANISM: Homo sapiens
<220> FEATURE:
<221> NAME/KEY: misc_feature
<223> OTHER INFORMATION: sequence of STAR50

<400> SEQUENCE: 50
caaccatcgt tccgcaagag cggcttgttt attaaacatg aaatgaggga aaagcctagt     60
agctccattg gattgggaag aatggcaaag agagacaggc gtcattttct agaaagcaat    120
cttcacacct gttggtcctc acccattgaa tgtcctcacc caatctccaa cacagaaatg    180
agtgactgtg tgtgcacatg cgtgtgcatg tgtgaaagta tgagtgtgaa tgtgtctata    240
tgggaacata tatgtgattg tatgtgtgta actatgtgtg actggcagcg tggggagtgc    300
tggttggagt gtggtgtgat gtgagtatgc atgagtggct gtgtgtatga ctgtggcggg    360
aggcggaagg ggagaagcag caggctcagg tgtcgccaga gaggctggga ggaaactata    420
aacctgggca atttcctcct catcagcgag cctttcttgg gcaataggg cagagctcaa    480 agttcacaga gatagtgcct gggaggcatg aggcaaggcg gaagtactgc gaggaggggc    540
agagggtctg acacttgagg ggttctaatg ggaaaggaaa gacccacact gaattccact    600
tagccccaga ccctgggccc agcggtgccg gcttccaacc ataccaacca tttccaagtg    660
ttgccggcag aagttaacct ctcttagcct cagtttcccc acctgtaaaa tggcagaagt    720
aaccaagctt accttcccgg cagtgtgtga ggatgaaaaa agctatgtac gtgatgcact    780
tagaagaagg tctagggtgt gagtggtact cgtctggtgg gtgtggagaa gacattctag    840
```

```
gcaatgagga ctggggagag cctggcccat ggcttccact cagcaaggtc agtctcttgt        900
cctctgcact cccagccttc cagagaggac cttcccaacc agcactcccc acgctgccag        960
tcacacatag ttacacacat acaatcacat atatgttccc atatagacac attcacactc       1020
ataccttcac acatgcacac gcatgtgcac acacagtcac tcatttctgt gttggagatt       1080
gggtgaggac attcaatggg tgaggaccaa caggtgtgaa gattgctttc tagaaaatga       1140
ctcctgtctc tctttgccat tcttcccaat ccgatggagc tactaggctt ttccctcatt       1200
tcatgtttaa taaaccttcc caatggcgaa atgggctttc tcaagaagtg gtgagtgtcc       1260
catccctgcg gtggggacag gggtggcagc ggacaagcct gcctggaggg aactgtcagg       1320
ctgattccca gtccaactcc agcttccaac acctcatcct ccaggcagtc ttcattcttg       1380
gctctaattt cgctcttgtt ttctttttta tttttatcga gaactgggtg gagagctttt       1440
ggtgtcattg gggattgctt tgaaaccctt ctctgcctca cactgggagc tggcttgagt       1500
caactggtct ccatggaatt tctttttta gtgtgtaaac agctaagttt taggcagctg       1560
ttgtgccgtc cagggtggaa agcagcctgt tgatgtggaa ctgcttggct cagatttctt       1620
gggcaaacag atgccgtgtc tctcaactca ccaattaaga agcccagaaa atgtggcttg       1680
gagaccacat gtctggttat gtctagtaat tcagatggct tcacctggga agccctttct       1740
gaatgtcaaa gccatgagat aaaggacata tatatagtag ctagggtggt ccacttctta       1800
ggggccatct ccggaggtgg tgagcactaa gtgccaggaa gagaggaaac tctgttttgg       1860
agccaaagca taaaaaaacc ttagccacaa accactgaac atttgttttg tgcaggttct       1920
gagtccaggg agggcttctg aggagagggg cagctggagc tggtaggagt tatgtgagat       1980
ggagcaaggg cccctttaaga ggtgggagca gcatgagcaa aggcagagag gtggtaatgt       2040
ataaggtatg tcatgggaaa gagtttggct ggaacagagt ttacagaata gaaaaattca       2100
acactattaa ttgagcctct actacgtgct cgacattgtt ctagtcactg agataggttt       2160
ggtatacaaa acaaaatcca tcctctatgg acattttagt gactaacaac aatataaata       2220
ataaaagtga acaaaagctc aaaacatgcc aggcactatt atttatttat ttatttattt       2280
atttatttat tttttgaaac agagtctcgc tctgttgccc aggctggagt gtagtggtgc       2340
gatctcggct cactg                                                       2355
```

<210> SEQ ID NO 51
<211> LENGTH: 2289
<212> TYPE: DNA
<213> ORGANISM: Homo sapiens
<220> FEATURE:
<221> NAME/KEY: misc_feature
<223> OTHER INFORMATION: sequence of STAR51

<400> SEQUENCE: 51

```
tcacaggtga caccaatccc ctgaccacgc tttgagaagc actgtactag attgactttc         60
taatgtcagt cttcattttc tagctctgtt acagccatgg tctccatatt atctagtaca        120
acacacatac aaatatgtgt gatacagtat gaatataata taaaaatatg tgttataata        180
taaatataat attaaaatat gtctttatac tagataataa tacttaataa cgttgagtgt        240
ttaactgctc taagcacttt acctgcagga aacagttttt tttttatttt ggtgaaatac        300
aactaacata aatttatttta caattttaag cattttaag tgtatagttt agtggagtta        360
atatattcaa aatgttgtgc agccgtcacc atcatcagtc ttcataactc ttttcatatt        420
gtaaaattaa aagtttatgc tcatttaaaa atgactccca atttcccccc tcctcaacct        480
```

| | |
|---|---|
| ctggaaacta ccattctatt ttctgcctcc gtagttttgc ccactctaag tacctcacat | 540 |
| aagtggaatt tgtcttattt gcctgtttgt gaccggctga tttcatttag tataatgtcc | 600 |
| tcaagtttta ttcacgttat atagcatatg tcataatttt cttcacttt aagcttgagt | 660 |
| aatatttcat cgtatgtatc tcacattttg cttatccatt catctctcag tggacacttg | 720 |
| agttgcttct acatttagc tgttgtgaat actgctgcta tgaacatggg tgtataaata | 780 |
| tctcaagacc tttttatcag tttttaaaa tatatactca gtagtagttt agctggatta | 840 |
| tatggtaatt ttattttaa tttttgagga actgtcctac cctttattc aatagtagct | 900 |
| ataccaattg acaattggca ttcctaccaa cagggcataa gggttctcaa ttctccacat | 960 |
| attccctgat acttgttatt ttcaggtgtt tttttttt tttttttttt atgggagcca | 1020 |
| tgttaatggg tgtaaggtga tatttcatta tagttttgat ttgcatttcc ctaatgatta | 1080 |
| gtgatgttaa gcatctcttc atgtgcctat tggccatttg tatatcttct ttaaaaatat | 1140 |
| atatatactc attcctttgc ccattttga attatgttta tttttgtta ttgagtttca | 1200 |
| atacttttct atataaccta ggtattaatc ctttatcaga cttaagattt gcaaatattc | 1260 |
| tctttcattc cacaggttgc taattctctc tgttggtaat atcttttgat gctgttgtgt | 1320 |
| ccagaattga ttcattcctg tgggttcttg gtctcactga cttcaagaat aaagctgcgg | 1380 |
| accctagtgg tgagtgttac acttcttata gatggtgttt ccggagtttg ttccttcaga | 1440 |
| tgtgtccaga gtttcttcct tccaatgggt tcatggtctt gctgacttca ggaatgaagc | 1500 |
| cgcagacctt cgcagtgagg tttacagctc taaaggtgg cgtgtccaga gttgtttgtt | 1560 |
| cccctggtg ggttcgtggt cttgctgact tcaggaatga agccgcagac cctcgcagtg | 1620 |
| agtgttacag ctcataaagg tagtgcggac acagagtgag ctgcagcaag atttactgtg | 1680 |
| aagagcaaaa gaacaaagct tccacagcat agaaggacac cccagcgggt tcctgctgct | 1740 |
| ggctcaggtg gccagttatt attcccttat ttgccctgcc cacatcctgc tgattggtcc | 1800 |
| attttacaga gtactgattg gtccattta cagagtgctg attggtgcat ttacaatcct | 1860 |
| ttagctagac acagagtgct gattgctgca ttcttacaga gtgctgattg gtgcatttac | 1920 |
| agtcctttag ctagatacag aacgctgatt gctgcgtttt ttacagagtg ctgattggtg | 1980 |
| catttacaat cctttagcta gacacagtgc tgattggtgg gttttacag agtgctgatt | 2040 |
| ggtgcgtctt tacagagtgc tgattggtgc atttacaatc cttagctag acacagagtg | 2100 |
| ctgattggtg cgtttataat cctctagcta gacagaaaag ttttccaagt ccccacctga | 2160 |
| ccgagaagcc ccactggctt cacctctcac tgttatactt tggacatttg tcccccaaa | 2220 |
| atctcatgtt gaaatgtaac ccctaatgtt ggaactgagg ccagactgga tgtggctggg | 2280 |
| ccatgggga | 2289 |

<210> SEQ ID NO 52
<211> LENGTH: 1184
<212> TYPE: DNA
<213> ORGANISM: Homo sapiens
<220> FEATURE:
<221> NAME/KEY: misc_feature
<223> OTHER INFORMATION: sequence of STAR52

<400> SEQUENCE: 52

| | |
|---|---|
| ctcttctttg ttttttatt ttggggtgtg tgggtacgtg taagatgaga aatgtacaaa | 60 |
| cacaagtatt tcagaaactc caagtaatat tctgtctgtg agttcacggt aaataaataa | 120 |
| aaagggcaaa gtgacagaaa tacaggatta ttaaaagcaa aataatgttc tttgaaatcc | 180 |

-continued

```
ccccctlggt gtatttttta tcttaggatg cagcacttc agcatgccca agtattgaaa      240
gcagtgtttt tacgctacca cggtaatttt atttagaaac cccatgttca cttttagttt      300
taaaatggtc tttatgacat aaaattatca gcattcatat ttttgtgttt taatattcct      360
ttggctactt attgaaacag taaacattac gaaaattagt aaacaaatct ttgatagttg      420 cttattttg tttaattgaa tgtttatttt attaggtaaa tatacaatca aatttattta      480
aaaataatga ggaaaagaat acttttcttt cgctttgcga aagcaaagtg attttcatt      540 cttctccgtc cgattccttc tcttccagct gccacagccg actgacaggc tcccggcggc      600
ctgaggagta gtatgcaaat tttggatgat tgacacctac agtagaagcc aatcacgtca      660
aagtaggatg ctgattggtt gacaacaata ggcgtaaacc ttgacgtttt aaaaacctga      720
cacccaatcc aggcgattca tgcaaataaa ggaagggagt cacattacca ggggccagag      780
agacttgagt acgacctcac gtgttcagtg gtggatattg cacagacgtc tgcaaggtct      840
atataaacgc tacataatgt tcaactcaat tgcttgcctt ggccttcccc aaacttgtca      900
ctggaatata aattatccct ttttaaaaa taaaaaaata agaattatgt agtgcacata       960
tatgatggtt catgtagaaa tctaaatgga cttccaacgc atggaatttt cctatttccc     1020
cctttcttta aattaatcct cagtgaagga ggctgttttc ccctagattt caaaaggacg     1080
agatttacag agcctttcct tggagaaacc cgctctaggc acagatggtc agtaaattta     1140
gcttcttcag cgaagttcca catggcaccg ccagatggca taag                     1184
```

<210> SEQ ID NO 53
<211> LENGTH: 1431
<212> TYPE: DNA
<213> ORGANISM: Homo sapiens
<220> FEATURE:
<221> NAME/KEY: misc_feature
<223> OTHER INFORMATION: sequence of STAR53

<400> SEQUENCE: 53

```
ccctgaggaa gatgacgagt aactccgtaa gagaaccttc cactcatccc ccacatccct       60
gcagacgtgc tattctgtta tgatactggt atcccatctg tcacttgctc cccaaatcat      120
tcccttctta caattttcta ctgtacagca ttgaggctga acgatgagag atttcccatg      180
ctctttctac tccctgccct gtatatatcc ggggatcctc cctacccagg atgctgtggg      240
gtcccaaacc ccaagtaagc cctgatatgc gggccacacc tttctctagc ctaggaattg      300
ataacccagg cgaggaagtc actgtggcat gaacagatgg ttcacttcga ggaaccgtgg      360
aaggcgtgtg caggtcctga gatagggcag aatcggagtg tgcagggtct gcaggtcagg      420
aggagttgag attgcgttgc cacgtggtgg gaactcactg ccacttattt ccttctctct      480
tcttgcctca gcctcaggga tacgacacat gcccatgatg agaagcagaa cgtggtgacc      540
tttcacgaac atgggcatgg ctgcggaccc ctcgtcatca ggtgcatagc aagtgaaagc      600
aagtgttcac aacagtgaaa agttgagcgt cattttctt agtgtgccaa gagttcgatg      660
ttagcgttta cgttgtattt tcttacactg tgtcattctg ttagatacta acattttcat      720
tgatgagcaa gacatactta atgcatattt tggtttgtgt atccatgcac ctaccttaga      780
aaacaagtat tgtcggttac ctctgcatgg aacagcatta ccctcctctc tccccagatg      840
tgactactga gggcagttct gagtgtttaa tttcagattt tttcctctgc atttacacac      900
acacgcacac aaaccacacc acacacacac acacacacac acacacacac acacacacac      960
acacaccaag taccagtata agcatctgcc atctgctttt cccattgcca tgcgtcctgg     1020
```

| | |
|---|---|
| tcaagctccc ctcactctgt ttcctggtca gcatgtactc ccctcatccg attcccctgt | 1080 |
| agcagtcact gacagttaat aaacctttgc aaacgttccc cagttgtttg ctcgtgccat | 1140 |
| tattgtgcac acagctctgt gcacgtgtgt gcatatttct ttaggaaaga ttcttagaag | 1200 |
| tggaattgct gtgtcaaagg agtcatttat tcaacaaaac actaatgagt gcgtcctcgt | 1260 |
| gctgagcgct gttctaggtg ctggagcgac gtcaggaac aaggcagaca ggagttcctg | 1320 |
| accccgttc tagaggagga tgtttccagt tgttgggttt tgtttgtttg tttcttctag | 1380 |
| agatggtggt cttgctctgt ccaggctaga gtgcagtggc atgatcatag c | 1431 |

<210> SEQ ID NO 54
<211> LENGTH: 975
<212> TYPE: DNA
<213> ORGANISM: Homo sapiens
<220> FEATURE:
<221> NAME/KEY: misc_feature
<223> OTHER INFORMATION: sequence of STAR54

<400> SEQUENCE: 54

| | |
|---|---|
| ccataaaagt gtttctaaac tgcagaaaaa tcccectaca gtcttacagt tcaagaattt | 60 |
| tcagcatgaa atgcctggta gattacctga cttttttgc caaaaataag gcacagcagc | 120 |
| tctctcctga ctctgacttt ctatagtcct tactgaatta tagtccttac tgaattcatt | 180 |
| cttcagtgtt gcagtctgaa ggacacccac attttctctt tgtctttgtc aattctttgt | 240 |
| gttgtaaggg caggatgttt aaagttgaa gtcattgact tgcaaaatga gaaatttcag | 300 |
| agggcatttt gttctctaga ccatgtagct tagagcagtg ttcacactga ggttgctgct | 360 |
| aatgtttctg cagttcttac caatagtatc atttacccag caacaggata tgatagagga | 420 |
| cttcgaaaac cccagaaaat gttttgccat atatccaaag ccctttggga aatggaaagg | 480 |
| aattgcgggc tcccattttt atatatggat agatagagac caagaaagac caaggcaact | 540 |
| ccatgtgctt tacattaata aagtacaaaa tgttaacatg taggaagtct aggcgaagtt | 600 |
| tatgtgagaa ttcttacac taattttgca acatttaat gcaagtctga aattatgtca | 660 |
| aaataagtaa aaattttac aagttaagca gagaataaca atgattagtc agagaaataa | 720 |
| gtagcaaaat cttcttctca gtattgactt ggttgctttt caatctctga ggacacagca | 780 |
| gtcttcgctt ccaaatccac aagtcacatc agtgaggaga ctcagctgag actttggcta | 840 |
| atgttggggg gtccctcctg tgtctcccca ggcgcagtga gcctgcaggc cgacctcact | 900 |
| cgtggcacac aactaaatct ggggagaagc aacccgatgc cagcatgatg cagatatctc | 960 |
| agggtatgat cggcc | 975 |

<210> SEQ ID NO 55
<211> LENGTH: 501
<212> TYPE: DNA
<213> ORGANISM: Homo sapiens
<220> FEATURE:
<221> NAME/KEY: misc_feature
<223> OTHER INFORMATION: sequence of STAR55

<400> SEQUENCE: 55

| | |
|---|---|
| cctgaactca tgatccgccc acctcagcct cctgaagtgc tgggattaca ggtgtgagcc | 60 |
| accacaccca gccgcaacac actcttgagc aaccatgtg tcataaaaga ataaaaatgg | 120 |
| aaatcagaaa gtatcttgag acagacaaaa atggaaacac aacataccaa aatttatggg | 180 |
| acacagcaaa agcagttta ggagggaagt ttatagtgat gaataccta ctcaaaatca | 240 |
| ttagcctgat tggatgacac tacagtgtat aaatgaattg aaaaccacat tgtgcccat | 300 |

```
acatatatac aattttat tgttaattaa aaataaaata aaactttaaa aaagaagaaa    360
gagctcaaat aaacaaccta actttatacc tcaaggaaat agaagagcca gctaagccca    420
aagttgacag aaggaaaaaa atattggcag aaagaaatga acagagact agaaagacaa     480 ttgaagagat cagcaaaact a                                              501

<210> SEQ ID NO 56
<211> LENGTH: 741
<212> TYPE: DNA
<213> ORGANISM: Homo sapiens
<220> FEATURE:
<221> NAME/KEY: misc_feature
<223> OTHER INFORMATION: sequence of STAR56

<400> SEQUENCE: 56
acacaggaaa agatcgcaat tgttcagcag agctttgaac cggggatgac ggtctccctc     60
gttgcccggc aacatggtgt agcagccagc cagttatttc tctggcgtaa gcaataccag    120
gaaggaagtc ttactgctgt cgccgccgga aacaggttg ttcctgcctc tgaacttgct     180
gccgccatga agcagattaa agaactccag cgcctgctcg gcaagaaaac gatggaaaat    240
gaactcctca agaagccgt tgaatatgga cgggcaaaaa agtggatagc gcacgcgccc     300
ttattgcccg gggatgggga gtaagcttag tcagccgttg tctccgggtg tcgcgtgcgc    360
agttgcacgt cattctcaga cgaaccgatg actggatgga tggccgccgc agtcgtcaca    420
ctgatgatac ggatgtgctt ctccgtatac accatgttat cggagagctg ccaacgtatg    480
gttatcgtcg ggtatgggcg ctgcttcgca gacaggcaga acttgatggt atgcctgcga    540
tcaatgccaa acgtgtttac cggatcatgc gccagaatgc gctgttgctt gagcgaaaac    600
ctgctgtacc gccatcgaaa cgggcacata caggcagagt ggccgtgaaa gaaagcaatc    660
agcgatggtg ctctgacggg ttcgagttct gctgtgataa cggagagaga ctgcgtgtca    720
cgttcgcgct ggactgctgt g                                             741

<210> SEQ ID NO 57
<211> LENGTH: 1365
<212> TYPE: DNA
<213> ORGANISM: Homo sapiens
<220> FEATURE:
<221> NAME/KEY: misc_feature
<223> OTHER INFORMATION: sequence of STAR57

<400> SEQUENCE: 57
tccttctgta aataggcaaa atgtatttta gtttccacca cacatgttct tttctgtagg     60
gcttgtatgt tggaaatttt atccaattat tcaattaaca ctataccaac aatctgctaa    120
ttctggagat gtggcagtga ataaaaaagt tatagtttct gattttgtgg agcttggact    180
ttaatgatgg acaaaacaac acattcttaa atatatattt catcaaaatt atagtgggtg    240
aattatttat atgtgcattt acatgtgtat gtatacataa atgggcggtt actggctgca    300
ctgagaatgt acacgtggcg cgaacgaggc tgggcggtca gagaaggcct cccaaggagg    360 tggcttgaa gctgagtggt gcttccacgt gaaaaggctg gaaagggcat tccaagaaaa     420
ggctgaggcc agcgggaaag aggttccagt gcgctctggg aacggaaagc gcacctgcct    480
gaaacgaaaa tgagtgtgct gaaataggac gctagaaagg gaggcagagg ctggcaaaag    540
cgaccgagga ggagctcaaa ggagcgagcg gggaaggccg ctgtggagcc tggaggaagc    600
acttcggaag cgcttctgag cgggtaaggc cgctgggagc atgaactgct gagcaggtgt    660
gtccagaatt cgtgggttct tggtctcact gacttcaaga atgaagaggg accgcggacc    720
```

```
ctcgcggtga gtgttacagc tcttaaggtg gcgcgtctgg agtttgttcc ttctgatgtt    780
cggatgtgtt cagagtttct tccttctggt gggttcgtgg tctcgctggc tcaggagtga    840
agctgcagac cttcgcggtg agtgttacag ctcataaaag cagggtggac tcaaagagtg    900
agcagcagca agatttattg caaagaatga agaacaaag cttccacact gtggaagggg     960
accccagcgg gttgccactg ctggctccgc agcctgcttt tattctctta tctggcccca   1020
cccacatcct gctgattggt agagccgaat ggtctgtttt gacggcgctg attggtgcgt   1080
ttacaatccc tgcgctagat acaaaggttc tccacgtccc caccagatta gctagataga   1140
gtctccacac aaaggttctc caaggcccca ccagagtagc tagatacaga gtgttgattg   1200
gtgcattcac aaaccctgag ctagacacag ggtgatgact ggtgtgttta caaaccttgc   1260
ggtagataca gagtatcaat tggcgtattt acaatcactg agctaggcat aaaggttctc   1320
caggtcccca ccagactcag gagcccagct ggcttcaccc agtgg               1365
```

<210> SEQ ID NO 58
<211> LENGTH: 1401
<212> TYPE: DNA
<213> ORGANISM: Homo sapiens
<220> FEATURE:
<221> NAME/KEY: misc_feature
<223> OTHER INFORMATION: sequence of STAR58

<400> SEQUENCE: 58

```
aagtttacct tagccctaaa ttatttcatt gtgattggca ttttaggaaa tatgtattaa     60
ggaatgtctc ttaggagata aggataacat atgtctaaga aaattatatt gaaatattat    120
tacatgaact aaaatgttag aactgaaaaa aaattattgt aactccttcc agcgtaggca    180
ggagtatcta gataccaact ttaacaactc aactttaaca acttcgaacc aaccagatgg    240
ctaggagatt cacctattta gcatgatatc ttttattgat aaaaaaatat aaaacttcca    300
ttaaattttt aagctactac aatcctatta aattttaact taccagtgtt ctcaatgcta    360
cataatttaa aatcattgaa atcttctgat tttaactcct cagtcttgaa atctacttat    420
ttttagttac atatatatcc aatctactgc cgctagtaga agaagcttgg aatttgagaa    480
aaaaatcaga cgttttgtat attctcatat tcactaattt attttttaaa tgagtttctg    540
caatgcatca agcagtggca aaacaggaga aaaattaaaa ttggttgaaa agatatgtgt    600
gccaaacaat cccttgaaat ttgatgaagt gactaatcct gagttattgt ttcaaatgtg    660 tacctgtttta tacaagggta tcacctttga aatctcaaca ttaaatgaaa ttttataagc    720
aatttgttgt aacatgatta ttataaaatt ctgatataac attttttatt acctgtttag    780
agtttaaaga gagaaaagga gttaagaata attacatttt cattagcatt gtccgggtgc    840
aaaaacttct aacactatct tcaaatcttt ttctccattg ccttctgaac atacccactt    900
gggtatctca ttagcactgc aaattcaaca ttttcgattg ctaatttttc tccctaaata    960
tttatttgtt ttctcagctt tagccaatgt ttcactattg accatttgct caagtatagt   1020
gacgcttcaa tgaccttcag agagctgttt cagtccttcc tggactactt gcatgcttcc   1080
aacaaaatga agcactcttg atgtcagtca ctcaaataaa tggaaatggg cccatttact   1140
aggaatgtta acagaataaa aagatagacg tgacaccagt tgcttcagtc catctccatt   1200
tacttgctta aggcctggcc atatttctca cagttgatat ggcgcagggc acatgtttaa   1260
atggctgttc ttgtaggatg gtttgactgt tggattcctc atcttccctc tccttaggaa   1320
```

-continued

| | |
|---|---|
| ggaaggttac agtagtactg ttggctcctg aatatagat tcataaagaa ctaatggagt | 1380 |
| atcatctccc actgctcttg t | 1401 |

<210> SEQ ID NO 59
<211> LENGTH: 866
<212> TYPE: DNA
<213> ORGANISM: Homo sapiens
<220> FEATURE:
<221> NAME/KEY: misc_feature
<223> OTHER INFORMATION: sequence of STAR59

<400> SEQUENCE: 59

| | |
|---|---|
| gagatcacgc cactgcactc cagcctgggg gacagagcaa gactccatct cagaaacaaa | 60 |
| caaacacaca aagccagtca aggtgtttaa ttcgacggtg tcaggctcag gtctcttgac | 120 |
| aggatacatc cagcacccgg gggaaacgtc gatgggtggg gtggaatcta ttttgtggcc | 180 |
| tcaagggagg gtttgagagg tagtcccgca agcggtgatg gcctaaggaa gcccctccgc | 240 |
| ccaagaagcg atattcattt ctagcctgta gccacccaag agggagaatc gggctcgcca | 300 |
| cagaccccac aaccccaac ccaccccacc cccaccctc ccacctcgtg aaatgggctc | 360 |
| tcgctccgtc aggctctagt cacaccgtgt ggttttggaa cctccagcgt gtgtgcgtgg | 420 |
| gttgcgtggt ggggtggggc cggctgtgga cagaggaggg gataaagcgg cggtgtcccg | 480 |
| cgggtgcccg ggacgtgggg cgtggggcgt gggtggggtg gccagagcct tgggaactcg | 540 |
| tcgcctgtcg ggacgtctcc cctcctggtc ccctctctga cctacgctcc acatcttcgc | 600 |
| cgttcagtgg ggaccttgtg ggtggaagtc accatcccct tggactttag ccgacgaagg | 660 |
| ccgggctccc aagagtctcc ccggaggcgg ggccttgggc aggctcacaa ggatgctgac | 720 |
| ggtgacggtt ggtgacggtg atgtacttcg gaggcctcgg gccaatgcag aggtatccat | 780 |
| ttgacctcgg tgggacaggt cagctttgcg gagtcccgtg cgtccttcca gagactcatc | 840 |
| cagcgctagc aagcatggtc ccgagg | 866 |

<210> SEQ ID NO 60
<211> LENGTH: 2067
<212> TYPE: DNA
<213> ORGANISM: Homo sapiens
<220> FEATURE:
<221> NAME/KEY: misc_feature
<223> OTHER INFORMATION: sequence of STAR60
<220> FEATURE:
<221> NAME/KEY: misc_feature
<222> LOCATION: (92)..(1777)
<223> OTHER INFORMATION: n is a, c, g, or t on various positions

<400> SEQUENCE: 60

| | |
|---|---|
| agcagtgcag aactggggaa gaagaagagt ccctacacca cttaatactc aaaagtactc | 60 |
| gcaaaaaata acacccctca ccaggtggca tnattactct ccttcattga gaaaattagg | 120 |
| aaactggact tcgtagaagc taattgcttt atccagagcc acctgcatac aaacctgcag | 180 |
| cgccacctgc atacaaacct gtcagccgac cccaaagccc tcagtcgcac caagcctctg | 240 |
| ctgcacaccc tcgtgccttc acactggccg ttccccaagc tgggggcata ctncccagct | 300 |
| ctgagaaatg tattcatcct tcaaagccct gctcatgtgt cctnntcaac aggaaaatct | 360 |
| cccatgagat gctctgctat ccccatctct cctgccccat agcttaggca nacttctgtg | 420 |
| gtggtgagtc ctgggctgtg ctgtgatgtg ttcgcctgcn atgtntgttc ttccccacaa | 480 |
| tgatgggccc ctgaattctc tatctctagc acctgtgctc agtaaaggct tgggaaacca | 540 |
| ggctcaaagc ctgcccaga tgccaccttt tccagggtgc ttccggggc caccaaccag | 600 |

```
agtgcagcct tctcctccac caggaactct tgcagcccca cccctgagca cctgcacccc    660
attacccatc tttgtttctc cgtgtgatcg tattattaca gaattatata ctgtattctt    720
aatacagtat ataattgtat aattattctt aatacagtat ataattatac aaatacaaaa    780
tatgtgttaa tggaccgttt atgttactgg taaagcttta agtcaacagt gggacattag    840
ttaggttttt ggcgaagtca aaagttatat gtgcattttc aacttcttga ggggtcggta    900
cntctnaccc ccatgttgtt caanggtcaa ctgtctacac atatcatagc taattcacta    960
cagaaatgtt agcttgtgtc actagtatct ccccttctca taagcttaat acacatacct   1020
tgagagagct cttggccatc tctactaatg actgaagttt ttatttatta tagatgtcat   1080
aataggcata aaactacatt acatcattcg agtgccaatt tgccaccttt gaccctcttt   1140
tgcaaaacac caacgtcagt acacatatga agaggaaact gcccgagaac tgaagttcct   1200
gagaccagga gctgcaggcg ttagatagaa tatggtgacg agagttacga ggatgacgag   1260
agtaaatact tcatactcag tacgtgccaa gcactgctat aagcgctctg tatgtgtgaa   1320
gtcatttaat cctcacagca tcccacggtg taattatttt cattatcccc atgagggaac   1380
agaaactcag aacggttcaa cacatatgcg agaagtcgca gccggtcagt gagagagcag   1440
gttcccgtcc aagcagtcag accccgagtg cacactctcg accctgtcc agcagactca    1500 ctcgtcataa ggcggggagt gntctgtttc agccagatgc tttatgcatc tcagagtacc   1560
caaaccatga agaatgagg cagtattcan gagcagatgg ngctgggcag taaggctggg   1620
cttcagaata gctggaaagc tcaagtnatg ggacctgcaa gaaaaatcca ttgtttngat    1680
aaatagccaa agtccctagg ctgtaagggg aaggtgtgcc aggtgcaagt ggagctctaa   1740
tgtaaaatcg cacctgagtc tcctggtctt atgagtnctg ggtgtacccc agtgaaaggt   1800
cctgctgcca ccaagtgggc catggttcag ctgtgtaagt gctgagcggc agccggaccg   1860
cttcctctaa cttcacctcc aaaggcacag tgcacctggt tcctccagca tcagctgcg    1920 aggcccctag ccagggtccc ggccccggc cccggcagc tgctccagct tccttccca     1980 cagcattcag gatggtctgc gttcatgtag acctttgttt tcagtctgtg ctccgaggtc   2040
actggcagca ctagccccgg ctcctgt                                       2067

<210> SEQ ID NO 61
<211> LENGTH: 1470
<212> TYPE: DNA
<213> ORGANISM: Homo sapiens
<220> FEATURE:
<221> NAME/KEY: misc_feature
<223> OTHER INFORMATION: sequence of STAR61
<220> FEATURE:
<221> NAME/KEY: misc_feature
<222> LOCATION: (130)..(976)
<223> OTHER INFORMATION: n is a, c, g, or t on various positions

<400> SEQUENCE: 61
cagcccccac atgcccagcc ctgtgctcag ctctgcagcg gggcatggtg ggcagagaca     60
cagaggccaa ggccctgctt cggggacggt gggcctggga tgagcatggc cttggccttc    120
gccgagagtn ctcttgtgaa ggaggggtca ggaggggctg ctgcagctgg ggaggagggc    180
gatggcactg tggcangaag tgaantagtg tgggtgcctn gcaccccagg cacggccagc    240
ctggggtatg gacccggggc cntctgttct agagcaggaa ggtatggtga ggacctcaaa    300
aggacagcca ctggagagct ccaggcagag gnacttgaga ggccctgggg ccatcctgtc    360
tcttttctgg gtctgtgtgc tctgggcctg ggcccttcct ctgctccccc gggcttggag    420
```

```
agggctggcc ttgcctcgtg caaaggacca ctctagactg gtaccaagtc tggcccatgg      480
cctcctgtgg gtgcaggcct gtgcgggtga cctgagagcc agggctggca ggtcagagtc      540
aggagaggga tggcagtgga tgccctgtgc aggatctgcc taatcatggt gaggctggag      600
gaatccaaag tgggcatgca ctctgcactc atttctttat tcatgtgtgc ccatcccaac      660
aagcagggag cctggccagg agggcccctg ggagaaggca ctgatgggct gtgttccatt      720
taggaaggat ggacggttgt gagacgggta agtcagaacg gctgccac ctcggccgag         780 agggccccgt ggtgggttgg caccatctgg gcctggagag ctgctcagga ggctctctag      840
ggctgggtga ccaggnctgg ggtacagtag ccatgggagc aggtgcttac ctggggctgt      900
ccctgagcag gggctgcatt gggtgctctg tgagcacaca cttctctatt cacctgagtc      960
ccnctgagtg atgagnacac ccttgttttg cagatgaatc tgagcatgga gatgttaagt     1020
ggcttgcctg agccacacag cagatggatg gtgtagctgg gacctgaggg caggcagtcc     1080
cagcccgagg acttcccaag gttgtggcaa actctgacag catgaccca gggaacaccc      1140 atctcagctc tggtcagaca ctgcggagtt gtgttgtaac ccacacagct ggagacagcc     1200
accctagccc cacccttatc ctctcccaaa ggaacctgcc cttccttc attttcctct       1260 tactgcattg agggaccaca cagtgtggca gaaggaacat gggttcagga cccagatgga     1320
cttgcttcac agtgcagccc tcctgtcctc ttgcagagtg cgtcttccac tgtgaagttg     1380
ggacagtcac accaactcaa tactgctggg cccgtcacac ggtgggcagg caacggatgg     1440
cagtcactgg ctgtgggtct gcagaggtgg                                       1470
```

<210> SEQ ID NO 62
<211> LENGTH: 1011
<212> TYPE: DNA
<213> ORGANISM: Homo sapiens
<220> FEATURE:
<221> NAME/KEY: misc_feature
<223> OTHER INFORMATION: sequence of STAR62

<400> SEQUENCE: 62

```
agtgtcaaat agatctacac aaaacaagat aatgtctgcc catttttcca aagataatgt       60
ggtgaagtgg gtagagagaa atgcatccat tctccccacc caacctctgc taaattgtcc      120
atgtcacagt actgagacca gggggcttat tcccagcggg cagaatgtgc accaagcacc      180
tcttgtctca atttgcagtc taggccctgc tatttgatgg tgtgaaggct tgcacctggc      240
atggaaggtc cgttttgtac ttcttgcttt agcagttcaa agagcaggga gagctgcgag      300
ggcctctgca gcttcagatg gatgtggtca gcttgttgga ggcgccttct gtggtccatt      360
atctccagcc cccctgcggt gttgctgttt gcttggcttg tctggctctc catgccttgt      420
tggctccaaa atgtcatcat gctgcacccc aggaagaatg tgcaggccca tctctttat    480 gtgctttggg ctattttgat tccccgttgg gtatattccc taggtaagac ccagaagaca      540
caggaggtag ttgctttggg agagtttgga cctatgggta tgaggtaata gacacagtat      600
cttctctttc atttggtgag actgttagct ctggccgcgg actgaattcc acacagctca      660
cttgggaaaa ctttattcca aaacatagtc acattgaaca ttgtggagaa tgagggacag      720
agaagaggcc ctagatttgt acatctgggt gttatgtcta taaatagaat gctttggtgg      780
tcaactagac ttgttcatgt tgacatttag tcttgccttt tcgtggtga tttaaaaatt       840 atgtatatct tgtttggaat atagtggagc tatggtgtgg cattttcatc tggctttttg      900
```

```
tttagctcag cccgtcctgt tatgggcagc cttgaagctc agtagctaat gaagaggtat    960
cctcactccc tccagagagc ggtcccctca cggctcattg agagtttgtc a            1011
```

<210> SEQ ID NO 63
<211> LENGTH: 1410
<212> TYPE: DNA
<213> ORGANISM: Homo sapiens
<220> FEATURE:
<221> NAME/KEY: misc_feature
<223> OTHER INFORMATION: sequence of STAR63

<400> SEQUENCE: 63

```
ccacagcctg atcgtgctgt cgatgagagg aatctgctct aagggtctga gcggagggag     60
atgccgaagc tttgagcttt ttgtttctgg cttaaccttg gtggattttc accctctggg    120
cattacctct tgtccagggg aggggctggg ggagtgcctg gagctgtagg gacagagggc    180
tgagtggggg ggactgcttg ggctgaccac ataatattct gctgcgtatt aattttttt    240
tgagacagtc tttctctgtt gcccaggctg gagtgtaatg gcttgatagc tcactgccac    300
ctccgcctcc tgggttcaag tgattctcct gcttcagctt ccggagtagc tgggactgca    360
ggtgcccgcc accatggctg gctaattttt gtattttat tagcaatggg gttttgctat     420
gttgcccagg ccgtcccga actcctgccc tcaagtgata cacctgcctc ggcctcccaa    480
agtgctggga ttagaggctt gagccactgc gcctggccag ctgcatattg ttaattagac    540
ataaaatgca aaataagatg atataaacac aaaggtgtga ataagatgg acacctgctg     600
agcgcgcctg tcctgaagca tcgccctct gcaaaagcag gggtcagcat gtgttctccg     660
gtccttgctc ttacagagga gtgagctgcc tatgcgtctt ccagccactt cctgggctgc    720
tcagaggcct ctcacggggtg ttctgggttg ctgccacttg caggggtgct gaggcggggc   780
tcctcccgtg cggggcatgt ccaggccgcc ctctctgaag gcttggcagg tacaggtggg    840
agtggggtc tctgggctgc tgtggggact gggcaggctc ctggaagacc tccctgtgtt    900
tgggctgaaa gcgcagcccg aggggaggtc cccaggagg ccgctgtcgg gggtggggggc   960
ttggaggagg gaggggccga ggagccggcg acactccgtg acggcccagg aacgtcccta   1020
aacaaggcgc cgcgttctcg atggggtggg gtccgctttc ttttctcaaa agctgcagtt   1080
actccatgct cggaggactg gcgtccgcgc cctgttccaa tgctgccccg gggccctggc   1140
cttgggggaat cggggccttg gactggaccc tggggggcttc gcggagccgg gcctggcggg   1200
gcgagcggag cagaggctgg gcagcccggg ggaagcgctc gccaaagccg ggcgctgctc   1260
ccagagcgcg aggtgcagaa ccagaggctg gtcccgcggc gctaacgaga gaagaggaag   1320
cgcgctgtgt agagggcgcc caccccgtgg ggcgaacccc cttcctcaac tccatggacg   1380
gggctcatgg gttcccagcg gctcagacgc                                    1410
```

<210> SEQ ID NO 64
<211> LENGTH: 1414
<212> TYPE: DNA
<213> ORGANISM: Homo sapiens
<220> FEATURE:
<221> NAME/KEY: misc_feature
<223> OTHER INFORMATION: sequence of STAR64

<400> SEQUENCE: 64

```
tggatcagat ttgttttata ccctcccttc tactgctctg agagttgtac atcacagtct     60
actgtatctg tttcccatta ttataatttt tttgcactgt gcttgcctga agggagcctc    120
aagttcatga gtctccctac cctcctccca aatgagacat ggacctttga atgctttcct    180
```

```
gggaccacca ccccaccttt catgctgctg ttatccagga ttttagttca acagtgtttt      240
aaccccccaa atgagtcatt tttattgttt cgtatagtga atgtgtattt gggtttgctt      300
atatggtgac ctgtttattt gctcctcatt gtacctcatg ctctgctctt tccttctaga      360
ttcagtctct ttcctaatga ggtgtctcgc agcaattctt tacaagacag ccaagatagg      420
ccagctctca gagcacttgt tgtctgaaaa agtcttgtct tatttaattt ctttttctta      480
gagatggggt ctcattatgt tacccacact ggtctcaaac ttctggctta aagcggtcct      540
cccaccttgg cctcccaaag tgctaggatt acaggcgtga gcgacctcgt ccagcctgtc      600
tgagaaagcg tttgttttgc ccttgctctc agatgacagt ttggggatag aattctaggt      660
ggacggtttt tttccttcag cccttttgaag agtctgtatt ttcattatct ccctgcatta     720
gatgttcttt tgcaagtaac gtgtcttttc tctctgggta ttcttaaggt tttctctttg      780
cctttggtga gctgcagtgg atttgctttt ttcaagaggt caagagaaag gaaagtgtga      840
ggtttctgtt ttttactgac aatttgtttg ttgatttgtt ttcccaccca gaggttcctt      900
gccactttgc caggctggaa ggcagacttc ttctggtgtc ctgttcacag acggggcagc      960
ctgcggaagg ccctgccaca tgcagggcct cggtcctcat tcccttgcat gtggacccgg     1020
gcgtgactcc tgttcaggct ggcacttccc agagctgagc cccagcctga ccttcctccc     1080
atactgtctt cacaccccct cctttcttct gatacctgga ggttttcctt tcttcctgt      1140 cacctccact tggattttaa atcctctgtc tgtggaattg tattcggcac aggaagatgc     1200
ttgcaagggc caggctcatc agccctgtcc ctgctgctgg aagcagcaca gcagagcctc     1260
atgctcaggc tgagatggag cagaggcctg cagacgagca cccagctcag ctggggttgg     1320
cgccgatggt ggagggtcct cgaaagctct ggggacgatg gcagagctat tggcagggga     1380
gccgcagggt cttttgagcc cttaaaagat ctct                                 1414
```

<210> SEQ ID NO 65
<211> LENGTH: 1310
<212> TYPE: DNA
<213> ORGANISM: Homo sapiens
<220> FEATURE:
<221> NAME/KEY: misc_feature
<223> OTHER INFORMATION: sequence of STAR65

<400> SEQUENCE: 65

```
gtgaatgttg atggatcaaa tatctttctg tgttgtttat caaagttaaa ataaatgtgg       60
tcatttaaag gacaaaagat gaggggttgg agtctgttca agcaagggt atattaggag       120 aaaagcagaa ttctctccct gtgaagggac agtgactcct attttccacc tcattttttac     180 taactctcct aactatctgc ttaggtagag atatatccat gtacatttat aaaccacagt      240
gaatcatttg attttggaat aaagatagta taaaatgtgt cccagtgttg atatacatca      300
tacattaaat atgtctggca gtgttctaat tttacagttg tccaaagata atgttagggc      360
atactggcta tggatgaagc tccaatgttc agattgcaaa gaaacttaga attttactaa      420
tgaaaccaaa tacatcccaa gaaattttc agaagaaaaa aagagaaact agtagcaaag       480 taagaatca ccacaatatc atcagatttt ttttatatgt agaatattta ttcagttctt       540
ttttcaagta caccttgtct tcattcattg tactttattt tttgtgaagg tttaaattta      600
tttcttctat gtgttagtg atattaaaaa ttttatttta atcaagttta tcagaaagtt      660
ctgttagaaa atatgacgag gctttaattc cgccatctat attttccgct attatataaa     720
gataattgtt ttctcttttt aaaacaactt gaattgggat tttatatcat aattttttaa    780
```

-continued

| | |
|---|---|
| tgtcttttt tattatactt taagttctgg gatacatgtg cagaacgtgc aggtgtgtta | 840 |
| catagatata cacgtgccat ggtggtttgc tgcacccact aacctgttat cgacattagg | 900 |
| tatttctcct aatgctatca cccctatttt cccaccccc cgagaggccc cagtgtgtga | 960 |
| tgttctcctc cctgtgtcca tgtgttctca ttgttcatct cccacttatg gtatctacca | 1020 |
| taaccttgaa attgtcttat gcattcactt gtttggttgt tatatagcct ccatcaggac | 1080 |
| agggatattt gctgctgctt ctttttttt tcttttttgag acagtcttgc tccgtcatcc | 1140 |
| aggctggagt gcttctcggc tcaatgcaac ctccacctcc caggtttaag cgattctcca | 1200 |
| acttcagcct cccaaatggc tgggactgca ggcatgcacc actacacctg gctaattttt | 1260 |
| gtatttgtaa tagagacaat gtttcaccat gttggccagg ctggtctcga | 1310 |

<210> SEQ ID NO 66
<211> LENGTH: 1917
<212> TYPE: DNA
<213> ORGANISM: Homo sapiens
<220> FEATURE:
<221> NAME/KEY: misc_feature
<223> OTHER INFORMATION: sequence of STAR67

<400> SEQUENCE: 66

| | |
|---|---|
| aggatcctaa aattttgtga ccctagagca agtactaact atgaaagtga aatagagaat | 60 |
| gaaggaatta tttaattaag tccagcaaaa cccaaccaaa tcatctgtaa aatatatttg | 120 |
| ttttcaacat ccaggtattt tctgtgtaaa aggttgagtt gtatgctgac ttattgggaa | 180 |
| aaataattga gttttcccct tcactttgcc agtgagagga aatcagtact gtaattgtta | 240 |
| aaggttaccc ataccctacct ctactaccgt ctagcatagg taaagtaatg tacactgtga | 300 |
| agtttcctgc ttgactgtaa tgttttcagt ttcatcccat tgattcaaca gctatttatt | 360 |
| cagcacttac tacaaccatg ctggaaaccc aagagtaaat aggctgtgtt actcaacagg | 420 |
| actgaggtac agccgaactg tcaggcaagg ttgctgtcct ttggacttgc ctgctttctc | 480 |
| tctatgtagg aagaagaaat ggacataccg tccaggaaat agatatatgt tacatttcct | 540 |
| tattccataa ttaatattaa taaccctgga cagaaactac caagtttcta gacccttata | 600 |
| gtaccacctt acccttctg gatgaatcct tcacatgttg atacatttta tccaaatgaa | 660 |
| aattttggta ctgtaggtat aacagacaaa gagagaacag aaaactagag atgaagtttg | 720 |
| ggaaaaggtc aagaaagtaa ataatgcttc tagaagacac aaaagaaaa atgaaatggt | 780 |
| aatgttggga aagttttaat acatttgcc ctaaggaaaa aaactacttg ttgaaattct | 840 |
| acttaagact ggacctttc tctaaaaatt gtgcttgatg tgaattaaag caacacaggg | 900 |
| aaatttatgg gctccttcta agttctaccc aactcaccgc aaaactgttc ctagtaggtg | 960 |
| tggtatactc tttcagattc tttgtgtgta tgtatatgtg tgtgtgtgtg tgtgtttgta | 1020 |
| tgtgtacagt ctatatacat atgtgtacct acatgtgtgt atatataaat atatatttac | 1080 |
| ctggatgaaa tagcatatta tagaatattc tttttctt aaatatatat gtgcatacat | 1140 |
| atgtatatgc acatatatac ataaatgtag atatagctag gtaggcattc atgtgaaaca | 1200 |
| aagaagccta ttactttta atggttgcat gatattccat cataggagta tagtacaact | 1260 |
| tatgtaacac acatttggct tgttgtaaaa ttttggtatt aataaaatag cacatatcat | 1320 |
| gcaaagacac ccttgcatag gtctattcat tctttgattt ttaccttagg acaaaattta | 1380 |
| aaagtagaat ttctgggtca agcagatagc tcatttaaaa tgtcattgca tatttccaaa | 1440 |
| ttgtcctcca gaaaagtagt aacagtaaca attgatggac tgcgtgtttt ctaaaacttg | 1500 |

-continued

```
cattttttc cttattggtg aggtttggca ttttccatat gtttattggc attttaattt      1560
tttttggttc atgtctttta ttcccttcct gcaaatttgt ggtgtgtctc aactttattt      1620
atactctcat tttcataatt ttctaaagga atttgacttt aaaaaaataa gacagccaat     1680
gctttggttt aatttcattg ctgcttttg aagtgactgc tgtgttttta tactttta       1740 tattttgttg ttttagcaaa ttcttctata ttataattgt gtatgctgga acaaaaagtt    1800
atatttctta atctagataa aatatttcaa gatgttgtaa ttacagtccc ctctaaaatc    1860
atataaatag acgcatagct gtgtgatttg taattagtta tgtccattga tagatcc       1917
```

```
<210> SEQ ID NO 67
<211> LENGTH: 26
<212> TYPE: DNA
<213> ORGANISM: Artificial
<220> FEATURE:
<223> OTHER INFORMATION: oligo for making linker containing MCSII of
      pd2EGFP-link

<400> SEQUENCE: 67
gtacggatat cagatcttta attaag                                          26
```

```
<210> SEQ ID NO 68
<211> LENGTH: 24
<212> TYPE: DNA
<213> ORGANISM: Artificial
<220> FEATURE:
<223> OTHER INFORMATION: oligo for making linker containing MCSII of
      pd2EGFP-link

<400> SEQUENCE: 68
gtaccttaat taaagatctg atat                                            24
```

```
<210> SEQ ID NO 69
<211> LENGTH: 52
<212> TYPE: DNA
<213> ORGANISM: Artificial
<220> FEATURE:
<223> OTHER INFORMATION: primer for amplification of 0.37 kb from
      pd2EGFP

<400> SEQUENCE: 69
gatcagatct ggcgcgccat ttaaatcgtc tcgcgcgttt cggtgatgac gg             52
```

```
<210> SEQ ID NO 70
<211> LENGTH: 41
<212> TYPE: DNA
<213> ORGANISM: Artificial
<220> FEATURE:
<223> OTHER INFORMATION: primer for amplification of 0.37 kb from
      pd2EGFP

<400> SEQUENCE: 70
aggcggatcc gaatgtattt agaaaaataa acaaataggg g                         41
```

```
<210> SEQ ID NO 71
<211> LENGTH: 36
<212> TYPE: DNA
<213> ORGANISM: Artificial
<220> FEATURE:
<223> OTHER INFORMATION: primer for amplifying zeocin resistance gene
      ORF

<400> SEQUENCE: 71
gatcggatcc ttcgaaatgg ccaagttgac cagtgc                               36
```

```
<210> SEQ ID NO 72
<211> LENGTH: 32
<212> TYPE: DNA
<213> ORGANISM: Artificial
<220> FEATURE:
<223> OTHER INFORMATION: primer for amplifying zeocin resistance gene
      ORF

<400> SEQUENCE: 72
aggcgcggcc gcaattctca gtcctgctcc tc                                   32

<210> SEQ ID NO 73
<211> LENGTH: 40
<212> TYPE: DNA
<213> ORGANISM: Artificial
<220> FEATURE:
<223> OTHER INFORMATION: primer for amplifying d2EGFP ORF

<400> SEQUENCE: 73
gatcgaattc tcgcgaatgg tgagcaagca gatcctgaag                           40

<210> SEQ ID NO 74
<211> LENGTH: 52
<212> TYPE: DNA
<213> ORGANISM: Artificial
<220> FEATURE:
<223> OTHER INFORMATION: primer for amplifying d2EGFP ORF

<400> SEQUENCE: 74
aggcgaattc accggtgttt aaacttacac ccactcgtgc aggctgccca gg             52

<210> SEQ ID NO 75
<211> LENGTH: 41
<212> TYPE: DNA
<213> ORGANISM: Artificial
<220> FEATURE:
<223> OTHER INFORMATION: primer for amplifying d2EGFP gene

<400> SEQUENCE: 75
ttggttggtc atgaatggtg agcaagggcg aggagctgtt c                         41

<210> SEQ ID NO 76
<211> LENGTH: 36
<212> TYPE: DNA
<213> ORGANISM: Artificial
<220> FEATURE:
<223> OTHER INFORMATION: primer for amplifying d2EGFP gene

<400> SEQUENCE: 76
attctctaga ctacacattg atcctagcag aagcac                               36

<210> SEQ ID NO 77
<211> LENGTH: 42
<212> TYPE: DNA
<213> ORGANISM: Artificial
<220> FEATURE:
<223> OTHER INFORMATION: oligo for preparing linker for creating MCS in
      pGL3-promoter-GFP

<400> SEQUENCE: 77
cgatatcttg gagatctact agtggcgcgc cttgggctag ct                        42

<210> SEQ ID NO 78
<211> LENGTH: 50
<212> TYPE: DNA
<213> ORGANISM: Artificial
```

-continued

```
<220> FEATURE:
<223> OTHER INFORMATION: oligo for preparing linker for creating MCS in
      pGL3-promoter-GFP

<400> SEQUENCE: 78
gatcagctag cccaaggcgc gccactagta gatctccaag atatcgagct              50

<210> SEQ ID NO 79
<211> LENGTH: 40
<212> TYPE: DNA
<213> ORGANISM: Artificial
<220> FEATURE:
<223> OTHER INFORMATION: primer for amplification of EF-1alfa promoter

<400> SEQUENCE: 79
gatcggcgcg ccatttaaat ccgaaaagtg ccacctgacg                         40

<210> SEQ ID NO 80
<211> LENGTH: 34
<212> TYPE: DNA
<213> ORGANISM: Artificial
<220> FEATURE:
<223> OTHER INFORMATION: primer for amplification of EF-1alfa promoter

<400> SEQUENCE: 80
aggcgggacc ccctcacgac acctgaaatg gaag                               34

<210> SEQ ID NO 81
<211> LENGTH: 51
<212> TYPE: DNA
<213> ORGANISM: Artificial
<220> FEATURE:
<223> OTHER INFORMATION: primer for amplification of SV40 promoter

<400> SEQUENCE: 81
ttggttgggg cgcgccgcag caccatggcc tgaaataacc tctgaaagag g            51

<210> SEQ ID NO 82
<211> LENGTH: 55
<212> TYPE: DNA
<213> ORGANISM: Artificial
<220> FEATURE:
<223> OTHER INFORMATION: primer for amplification of SV40 promoter

<400> SEQUENCE: 82
ttggttggga gctcaagctt tttgcaaaag cctaggcctc caaaaaagcc tcctc        55
```